(12) United States Patent
Aszodi et al.

(10) Patent No.: US 7,612,087 B2
(45) Date of Patent: Nov. 3, 2009

(54) HETEROCYCLIC COMPOUNDS AS INHIBITORS OF BETA-LACTAMASES

(75) Inventors: Jozsef Aszodi, Tucson, AZ (US); Claude Fromentin, Paris (FR); Maxime Lampilas, Saint Cloud (FR); David Alan Rowlands, Poissy (FR)

(73) Assignee: Novexel, Romainville (FR)

( * ) Notice: Subject to any disclaimer, the term of this patent is extended or adjusted under 35 U.S.C. 154(b) by 717 days.

(21) Appl. No.: 10/898,754

(22) Filed: Jul. 26, 2004

(65) Prior Publication Data

US 2005/0020572 A1 Jan. 27, 2005

Related U.S. Application Data

(63) Continuation of application No. PCT/FR03/00243, filed on Jan. 27, 2003.

(30) Foreign Application Priority Data

Jan. 28, 2002 (FR) .................. 02 00951

(51) Int. Cl.
*A61K 31/44* (2006.01)
*A61K 31/545* (2006.01)

(52) U.S. Cl. .................. 514/300; 514/299; 514/295; 514/203

(58) Field of Classification Search .................. 514/295, 514/299, 300, 203
See application file for complete search history.

(56) References Cited

U.S. PATENT DOCUMENTS

| | | | |
|---|---|---|---|
| 5,719,141 A | 2/1998 | Rasetti et al. | |
| 5,932,587 A | 8/1999 | Schmeck et al. | |
| 5,994,340 A * | 11/1999 | Maiti et al. .................. | 514/192 |
| 7,288,549 B2 | 10/2007 | Aszodi et al. | |
| 2003/0199541 A1 | 10/2003 | Lampilas et al. | |
| 2004/0157826 A1 | 8/2004 | Lampilas et al. | |
| 2006/0046995 A1 | 3/2006 | Lampilas et al. | |
| 2006/0189652 A1 | 8/2006 | Lampilas et al. | |
| 2007/0299108 A1 | 12/2007 | Aszodi et al. | |

FOREIGN PATENT DOCUMENTS

| | | |
|---|---|---|
| EP | 0260057 A2 | 3/1988 |
| EP | 0702004 A2 | 3/1996 |
| EP | 0818197 A1 | 1/1998 |
| FR | 2676230 A1 | 11/1992 |
| JP | 5339263 | 12/1993 |
| WO | 90/15058 A1 | 12/1990 |
| WO | 95/09175 A1 | 4/1995 |
| WO | WO 95/18129 | 7/1995 |
| WO | 96/29327 A1 | 9/1996 |
| WO | 97/23484 A1 | 7/1997 |
| WO | WO 97/25309 | 7/1997 |
| WO | WO 98/05659 | 2/1998 |
| WO | 99/01434 A1 | 1/1999 |
| WO | 99/16442 A2 | 4/1999 |
| WO | WO 99/21855 | 5/1999 |
| WO | 99/52875 A1 | 10/1999 |
| WO | 00/00479 A1 | 1/2000 |
| WO | 00/12507 A2 | 3/2000 |
| WO | 00/37458 A1 | 6/2000 |
| WO | 00/63187 A1 | 10/2000 |
| WO | 01/25228 A1 | 4/2001 |
| WO | 01/79206 A1 | 10/2001 |
| WO | WO0210172 | 2/2002 |
| WO | 02/067937 A1 | 9/2002 |
| WO | 02/100860 A2 | 12/2002 |
| WO | 03/063864 A2 | 8/2003 |

OTHER PUBLICATIONS

Hall, H. K. Jr., Polymerization and ring strain in bridged bicyclic compounds, Journal of the American Chemical Society, vol. 80, 1958, pp. 6412-6420.
Hall, H. K., Jr. et al, Anti-Bredt molecules. 3. 3-Oxa-1-azabicyclo[3.3.1]nonan-2-one and 6-oxa-1-azabicyclo[3.2.1]octan-7-one, two atom-bridged bicyclic urethanes possessing bridgehead nitrogen, Journal of Organic Chemistry, vol. 45(26), 1980, pp. 5325-5328.
Bonnefoy, Alain et al., "In Vitro activity of AVE1330A, an innovative broad-spectrum non-β-lactam β-lactamase inhibitor," Journal of Antimicrobial Chemotherapy, vol. 54, No. 2, 2004, pp. 410-417.
Booker-Milburn, K.I. et al., "Azabenzocycloheptenones. Part 20. Synthesis and utilisation of 4-amino-1,2,3,4-tetrahydro-1(1H)-benzazepines," J. Chem. Soc., Perkin Trans. 1: Organic and Bio-Organic Chemistry, pp. 3261-3273 (1997).
Chen, et al, Synthesis of N-substituted 1,6-Dihydro-3(2H)-Pyridinones and 1-Acyl-3-Piperidones, Heterocycles, vol. 22, No. 12, pp. 2769-2773 (1984).

(Continued)

*Primary Examiner*—Shengjun Wang
(74) *Attorney, Agent, or Firm*—Harness, Dickey & Pierce, P.L.C.

(57) ABSTRACT

This invention discloses and claims methods for inhibiting bacterial β-lactamases and treating bacterial infections by inhibiting bacterial β-lactamases in man or an animal comprising administering a therapeutically effective amount to said man or said animal of a compound, or pharmaceutically acceptable salt thereof, of formula (I) either alone or in combination with a β-lactamine antibiotic wherein said combination can be administered separately, together or spaced out over time. Pharmaceutical compositions comprising a compound of formula (I), or a combination of a compound of formula (I) and a therapeutically effective amount of a β-lactamine antibiotic, and a pharmaceutically acceptable carrier are also disclosed and claimed.

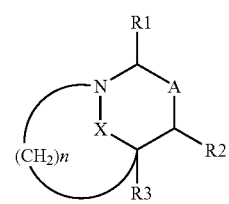

16 Claims, No Drawings

OTHER PUBLICATIONS

Elliott, R. et al., "Syntheses and stereochemistry of 4-hydroxy tetrahydroisoquinolines in the 1-benzyl and 1-phenethyl series. Efficient routes to isopavines and homoisopavines," Tetrahedron Letters, vol. 21, pp. 4633-4636 (1980).

Hall, Jr. et al., "3-Isopropyl-1,3-diazabicyclo[3,3,1]nonan-2-one, a Simple Bicyclic Urea with a Bridgehead Nitrogen Atom", J. Org. Chem., vol. 37, Issue 5, pp. 697-699 (1972).

Hall, Jr. et al, "Anti-Bredt Bridgehead Nitrogen Compounds in Ring-Opening Polymerization", Chemical Reviews, vol. 83, Issue 5, pp. 549-555 (1983).

Heier, R.F. et al., "An asymmetric synthesis of (R)-5,6-dihydro-5-(methylamino)-4H-imidazo-[4,5,1-ij]quinolin-2(1H)-one and its [2-14C]- and [6,7-3H2]-labeled forms," CAPLUS Database, Chemical Abstracts Service, Columbus, Ohio (1997).

Heier, R.F. et al., "Synthesis and Biological Activities of (R)-5,6-Dihydro-N,N-dimethyl-4H-imidazo[4,5,1-ij]quinolin-5-amine and Its Metabolites," J. Med. Chem., vol. 40, pp. 639-646 (1997).

Itoh, "Synthesis and Structure of 4-Substituted Decahydroisoquinoline Derivatives", Chem. Pharm. Bull., vol. 16, Issue 3, pp. 455-470 (1968).

Levasseur, P. et al., "Efficacy of NXL104 (Previously AVE1330A), a Novel Broad Spectrum β-Lactamase Inhibitor, in Combination with Ceftazidime (CAZ) in Murine Septicaemia and Pneumonia", Presentation No. F-1164, 46th ICAAC, San Francisco, CA, Dec. 17, 2005, 1 page (Abstract only).

Levasseur, P. et al., "NXL104, a Novel β-Lactamase Inhibitor, Restores the Bactericidal Activity of Ceftazidime against ESBL and AmpC Producing Strains of Enterobacteriaceae", Presentation No. F-127, 46th ICAAC, San Francisco, CA, Dec. 17, 2005, 2 pages (Abstract and Poster Presentation).

Masumoto, S. et al., "Preparation of tricyclic quinazolinediones as poly (ADP-ribose) polymerase inhibitors," CAPLUS Database, Chemical Abstracts Service, Columbus, Ohio (2001).

Moon, M.W. et al., "Dopaminergic and Serotonergic Activities of Imidazoquinolinones and Related Compounds," J. Med. Chem., vol. 35, pp. 1076-1092 (1992).

Moon, M.W. et al., "Medicinal chemistry of imidazoquinolinone dopamine receptor agonists," CAPLUS Database, Chemical Abstracts Service, Columbus, Ohio (1994).

Moon, M.W. et al., "Synthesis of tritium-labeled (R)-5-(di[2,3-3H2]propylamino)-5,6-dihydro-4H-imidazo-[4,5,1-ij]quinolin-2(1H)-one([3H]U-86170) and (R)-5-([2,3-3H2]propylamino)-5,6-dihydro-4H-imidazo-[4,5,1-ij]quinolin-2(1H)-one([3H]U-91356)," CAPLUS Database, Chemical Abstracts Service, Columbus, Ohio (1993).

Nagagsaka, T. et al., "Preparation of 1,4-dihydro-4-phenyl-3,5-pyridinedicarboxylic acids as calcium antagonists," CAPLUS Database, Chemical Abstracts Service, Columbus, Ohio (1994).

Nicolaou, et al., "New Synthetic Technology for the Rapid Construction of Novel Heterocycles—Part 2. The Reaction of IBX with Anilides and Related Compounds", Chem. Int. Ed., vol. 39, Issue 3, pp. 625-628 (2000).

Novexel Press Release, Novexel Announces Phase I Clinical Trial of NXL104, A Novel Broad-Spectrum Beta-Lactamase Inhibitor, Dec. 18, 2006, Paris, France, 2 pages, Downloaded Jul. 2, 2008, (www.novexel.com/IMG/pdf/CM_NXL104_Phase_1_PR_FINAL.pdf).

* cited by examiner

HETEROCYCLIC COMPOUNDS AS INHIBITORS OF BETA-LACTAMASES

This application is a continuation of International Application No. PCT/FR03/00243 filed Jan. 27, 2003, which claims the benefit of priority of French Application No. 02 00951, filed Jan. 28, 2002.

BACKGROUND OF THE INVENTION

1. Field of the Invention

The invention relates to heterocyclic compounds, endowed with beta-lactamase inhibitory properties, and therefore are of interest in combating infectious diseases or in the prevention of them, in the form of a combination with various antibiotic compounds of β-lactamine type, in order to reinforce their effectiveness in combating the pathogenic bacteria which produce β-lactamases.

2. Description of the Art

It is well known that the enzymatic inactivation of antibiotics of β-lactamine type, whether compounds of penicillin or cephalosporin type, in the treatment of bacterial infections is a obstacle for this type of compound. This inactivation consists of a degradation process of the β-lactamines and constitutes one of the mechanisms by which the bacteria can become resistant to treatments. It is therefore desirable to act against this enzymatic process by combining an agent capable of inhibiting the enzyme with the antibacterial agent of β-lactamine type. When an inhibitor of β-lactamase is used in combination with an antibiotic of β-lactamine type, it can thus reinforce its effectiveness against certain microorganisms.

SUMMARY OF THE INVENTION

The invention therefore relates to the compounds corresponding to the formula (I):

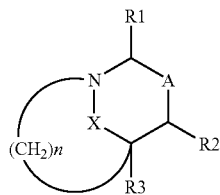

in which:

$R_1$ represents a hydrogen atom, a COOH, CN, COOR, CONR$_6$,R$_7$, (CH$_2$)$_n$·R$_5$ or

radical R is chosen from group constituted by an alkyl radical containing 1 to 6 carbon atoms, optionally substituted by a pyridyl or carbamoyl radical, a —CH$_2$-alkenyl radical containing a total of 3 to 9 carbon atoms, aryl containing 6 to 10 carbon atoms or aralkyl containing 7 to 11 carbon atoms, the nucleus of aryl or aralkyl radical being optionally substituted by an OH, NH$_2$, NO$_2$, alkyl radical containing 1 to 6 carbon atoms, alkoxy containing 1 to 6 carbon atoms or by one or more halogen atoms, $R_6$ and $R_7$, identical or different, are chosen from the group constituted by a hydrogen atom, an alkyl radical containing 1 to 6 carbon atoms, aryl containing 6 to 10 carbon atoms and aralkyl containing 7 to 11 carbon atoms, optionally substituted by a carbamoyl, ureido or dimethylamino radical, and an alkyl radical containing 1 to 6 carbon atoms substituted by a pyridyl radical, n' is equal to 1 or 2 and $R_5$ is chosen from the group constituted by a COOH, CN, OH, NH$_2$, CO—NR$_6$R$_7$, COOR, OR, OCHO, OCOR, OCOOR, OCONHR, OCONH$_2$, NHR, NHCOH, NHCOR, NHSO$_2$R, NH—COOR, NH—CO—NHR or NHCONH$_2$ radical, R, R$_6$ and R$_7$ being as defined above;

$R_2$ represents a hydrogen atom or a (CH$_2$)$_{n'_1}$R$_5$ group, n'$_1$ being equal to 0, 1 or 2, and R$_5$ being as defined above;

$R_3$ represents a hydrogen atom or an alkyl radical containing 1 to 6 carbon atoms;

A represents a bond between the two carbons which carry $R_1$ and $R_2$ or a

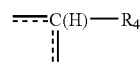

group, $R_4$ representing a hydrogen atom or a (CH$_2$)$_{n'_1}$R$_5$ group, n'$_1$ and $R_5$ being as defined above, the dotted line representing an optional additional bond with one or other of the carbons which carry the substituents $R_1$ and $R_2$, n is equal to 1 or 2, X represents a divalent —C(O)—B— group linked to the nitrogen atom by the carbon atom, B represents a divalent —O—(CH$_2$)$_{n''}$— group linked to the carbonyl by the oxygen atom, an —NR$_8$—(CH$_2$)$_{n''}$— or —NR$_8$—O— group linked to the carbonyl by the nitrogen atom, n'' is equal to 0 or 1 and R$_8$, in the case of —NR$_8$—(CH$_2$)$_{n''}$— is chosen from the group constituted by a hydrogen, an OH, R, OR, Y, OY, Y$_1$, OY$_1$, Y$_2$, OY$_2$, Y$_3$, OCH$_2$CH$_2$SO$_m$R, OSiR$_a$R$_b$R$_c$ and SiR$_a$R$_b$R$_c$ radical, and in the case of —NR$_8$—O— is chosen from the group constituted by a hydrogen, an R, Y, Y$_1$, Y$_2$, Y$_3$ and SiR$_a$R$_b$R$_c$ radical, R$_a$, R$_b$ and R$_c$ representing individually a linear or branched alkyl radical containing 1 to 6 carbon atoms or an aryl radical containing 6 to 10 carbon atoms, R being as defined previously and m being equal to 0, 1 or 2, Y is chosen from the group constituted by the COH, COR, COOR, CONH$_2$, CONHR, CONHOH, CONHSO$_2$R, CH$_2$COOH, CH$_2$COOR, CH$_2$CONHOH, CH$_2$CONHCN, CH$_2$tetrazole, protected CH$_2$tetrazole, CH$_2$SO$_3$H, CH$_2$SO$_2$R, CH$_2$PO(OR)$_2$, CH$_2$PO(OR)(OH), CH$_2$PO(R)(OH) and CH$_2$PO(OH)$_2$ radicals, Y$_1$ is chosen from the group constituted by the SO$_2$R, SO$_2$NHCOH, SO$_2$NHCOR, SO$_2$NHCOOR, SO$_2$NHCONHR SO$_2$NHCONH$_2$ and SO$_3$H radicals, Y$_2$ is chosen from the group constituted by the PO(OH)$_2$, PO(OR)$_2$, PO(OH)(OR) and PO(OH)(R) radicals, Y$_3$ is chosen from the group constituted by the following radicals: tetrazole, tetrazole substituted by the R, squarate, NH or NR tetrazole, NH or NR tetrazole substituted by the R radical, NHSO$_2$R and NRSO$_2$R, R being as defined above;

$R_1$, $R_2$ and $R_3$ not representing all three at the same time a hydrogen atom when n is equal to 1 and A represents a

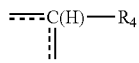

group in which $R_4$ is a hydrogen atom and
either X represents the —C(O)—O—$(CH_2)_{n''}$ group in which n" is 0 or 1,
or X represents the —CO—$NR_8$—$(CH_2)_{n''}$ group in which n" is 1 and $R_8$ is the isopropyl group,
or X represents the —CO—$NR_8$—$(CH_2)_{n''}$ group in which n" is 0 and $R_8$ is hydrogen or phenyl, as well as the salts of these compounds with mineral or organic bases or acids, as well as the internal salts in the form in which they can, if appropriate, be presented.

The compounds of formula (I) and their salts are described and claimed in the International Patent Application No. PCT/FR01/02418 filed on the 24th Jul. 2001, claiming priority from the French Application No. °0010121 filed on the 1st Aug. 2000.

The compounds of formula (I) are presented in the form of pure enantiomers or pure diastereoisomers or in the form of a mixture of enantiomers in particular of racemates, or mixtures of diastereoisomers. Moreover, the substituents $R_1$, $R_2$, $R_4$ taken individually on the one hand and X on the other can be in cis and/or trans position with respect to the ring on which they are fixed, and the compounds of formula (I) are therefore presented in the form of cis isomers or trans isomers or mixtures.

By alkyl radical containing 1 to 6 carbon atoms, is meant the methyl, ethyl radical, as well as propyl, butyl, pentyl or hexyl linear, branched or cyclic.

By —$CH_2$-alkenyl radical containing 3 to 9 carbon atoms, is meant for example the allyl radical, or a butenyl, pentenyl or hexenyl radical.

By aryl radical containing 6 to 10 carbon atoms, is meant a phenyl or naphthyl radical.

By aralkyl radical containing 7 to 11 carbon atoms, is meant a benzyl, phenethyl or methylnaphthyl radical.

By alkyloxy radical containing 1 to 6 carbon atoms, is meant in particular the methoxy, ethoxy, propoxy, isopropoxy radical, as well as butoxy, isobutoxy, dry-butoxy or tert-butoxy radical.

By halogen atom, is meant a fluorine, chlorine, bromine or iodine atom.

By squarate radical, is meant the radical of formula:

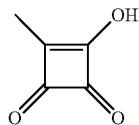

Among the salts with acids of the products of formula (I), there can be mentioned, amongst others, those formed with mineral acids, such as hydrochloric, hydrobromic, hydroiodic, sulphuric or phosphoric acids or with organic acids such as formic, acetic, trifluoroacetic, propionic, benzoic, maleic, fumaric, succinic, tartaric, citric, oxalic, glyoxylic, aspartic acid, alkanesulphonics, such methane and ethane sulphonic acids, arylsulphonics such as benzene and paratoluenesulphonic acids.

Among the salts with bases of the products of formula (I), there can be mentioned, amongst others, those formed with mineral bases such as, for example, sodium, potassium, lithium, calcium, magnesium or ammonium hydroxide or with organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine, or also phosphonium salts, such as alkyl-phosphoniums, aryl-phosphoniums, alkyl-aryl-phosphoniums, the alkenyl-aryl-phosphoniums or quaternary ammonium salts such the salt of tetra-n-butyl-ammonium.

A subject of the invention is the use of the compounds of formula (I), as well as their pharmaceutically acceptable salts, for the preparation of a medicament intended to inhibit the production of β-lactamases by pathogenic bacteria.

A subject of the invention is also the use of the compounds of formula (I), as well as their pharmaceutically acceptable salts, which inhibit the production of β-lactamases by pathogenic bacteria, for the preparation of a medicament intended for the treatment of bacterial infections in man or animals.

A particular subject of the invention is a use according to what has gone before, characterized in that the compounds correspond to formula (I) in which n is equal to 1 and A and $R_2$ are as defined above, $R_3$ represents a hydrogen atom, $R_1$ represents a hydrogen atom, a COOR or $CONR_6R_7$ radical, $R_6$ and $R_7$ being as defined above and X represents a —C(O)—B— group in which B represents an —O—$(CH_2)_{n''}$— or —$NR_8$—$(CH_2)_{n''}$— group, n" being equal to O and $R_8$ having the values as defined above and, more particularly the values Y, $Y_1$ and $OY_1$, and more particularly, from among these, those corresponding to formula (I) in which A represents a

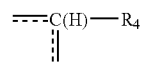

group in which $R_4$ represents a hydrogen atom, $R_2$ represents a hydrogen atom and B represents an $NR_8$—$(CH_2)_{n''}$— group in which n" is equal to O and $R_8$ represents an $OY_1$ radical.

A quite particular subject of the invention is a use as defined above, characterized in that the compounds are chosen from the list constituted by:

cis-7-oxo-6-oxa-1-azabicyclo[3.2.1]octane-4--propanoic acid, trans diphenylmethyl 7-oxo-6-oxa-1-azabicyclo[3.2.1]octan-4-acetate, cis diphenylmethyl 7-oxo-6-oxa-1-azabicyclo[3.2.1]octan-4-acetate, trans phenylmethyl 3-benzoyl-2-oxo-1,3-diazabicyclo[2.2.1]heptane-6-carboxylate, trans phenylmethyl 2-oxo-3-(sulphooxy)-1,3-diazabicyclo[2.2.1]heptane-6-carboxylate, 6-[[(4-methylphenyl)sulphonyl]oxy]-1,6-diazabicyclo[3.2.1]octan-7-one, 6-[(methylsulphonyl)oxy]-1,6-diazabicyclo[3.2.1]octan-7-one, 6-[(4-nitrophenyl)sulphonyl]oxy]-1,6-diazabicyclo[3.2.1]octan-7-one, trans diphenylmethyl 7-oxo-6-oxa-1-azabicyclo[3.2.1]octane-2-carboxylate, trans (4-nitrophenyl)methyl 7-oxo-6-oxa-1-azabicyclo[3.2.1]octane-2-carboxylate, trans-7-oxo-6-oxa-1-azabicyclo[3.2.1.]octane-2 carboxylic acid, trans phenylmethyl 7-oxo-6-(sulphooxy)-1,6-diazabicyclo[3.2.1]octane-2-carboxylate, trans phenylmethyl 7-oxo-6-(sulphooxy)-1,6-diazabicyclo[3.2.1]octane-2-carboxylate, trans phenylmethyl 7-oxo-6-[(phenylsulphonyl)oxy]-1,6-diazabicyclo[3.2.1]octane-2-carboxylate, trans phenylmethyl 7-oxo-6-[(2-thienylsulphonyl)oxy]-1,6-diazabicyclo[3.2.1]octane-2-carboxylate, trans-6-benzoyl-7-oxo-1,6-diazabicyclo[3.2.1]octane-2-carboxylic acid, trans methyl 6-benzoyl-7-oxo-1,6-diazabicyclo[3.2.1]octane-2-carboxylate, trans-7-oxo-6-(sulphooxy)-1,6-diazabicyclo[3.2.1]octane-2-carboxamide, trans-7-oxo-N-(phenylmethyl)-6-(sulphooxy)-1,6-diazabicyclo[3.2.1]octane-2-carboxamide, trans-7-oxo-N-(2-pyridinylmethyl)-6-(sulphooxy)-1,6-diazabicyclo[3.2.1]octane-2-carboxamide, trans-7-oxo-N-[2-(3-pyridinyl)ethyl]-6-(sulphooxy)-1,6-diazabicyclo[3.2.1]octane-2-carboxamide, trans-7-oxo-N-[2-(4-pyridinyl)ethyl]-6-(sulphooxy)-1,6-diazabicyclo[3.2.1]octane-2-carboxamide, trans-7-oxo-N-[2-(2-pyridinyl)ethyl]-6-(sulphooxy)-1,6-diazabicyclo[3.2.1]octane-2-carboxamide, trans-N-[3-(aminocarbonyl)phenyl]-7-oxo-6-(sulphooxy)-1,6-diazabicyclo[3.2.1]octane-2-carboxamide, trans-N-[4-(dimethylamino)phenyl]-7-oxo-6-(sulphooxy)-1,6-diazabicyclo[3.2.1]octane-2-carboxamide, trans-N-[3-(dimethylamino)phenyl]-7-oxo-6-(sulphooxy)-1,6-diazabicyclo[3.2.1]octane-2-carboxamide, trans-7-oxo-N-[(4-pyridinyl)methyl]-6-(sulphooxy)-1,6-diazabicyclo[3.2.1]octane-2-carboxamide, trans-7-oxo-N-(3-pyridinylmethyl)-6-(sulphooxy)-1,6-diazabicyclo[3.2.1]octane-2-carboxamide, trans-N-(1-amino-1-oxo-3-phenyl-2-propyl)-7-oxo-6-(sulphooxy)-1,6-diazabicyclo[3.2.1]octane-2-carboxamide, trans-N-(2-amino-2-oxoethyl)-7-oxo-6-(sulphooxy)-1,6-diazabicyclo[3.2.1]octane-2-carboxamide, trans-N-[3-[(aminocarbonyl)amino]phenyl]-7-oxo-6-(sulphooxy)-1,6-diazabicyclo[3.2.1]octane-2-carboxamide, trans-N-(2-amino-2-oxo-1-phenylethyl)-7-oxo-6-(sulphooxy)-1,6-diazabicyclo[3.2.1]octane-2-carboxamide, trans 2-amino-2-oxoethyl 7-oxo-6-(sulphooxy)-1,6-diazabicyclo[3.2.1]octane-2-carboxylate, trans 2-(4-pyridinyl)ethyl 7-oxo-6-(sulphooxy)-1,6-diazabicyclo[3.2.1]octane-2-carboxylate, trans 2-(2-pyridinyl)ethyl 7-oxo-6-(sulphooxy)-1,6-diazabicyclo[3.2.1]octane-2-carboxylate, 6-(sulphooxy)-1,6-diazabicyclo[3.2.1]oct-3-in-7-one, 3-methoxy-6-(sulphooxy)-1,6-diazabicyclo[3.2.1]oct-3-in-7-one, as well as their salts.

A subject of the invention is also a use as defined above, characterized in that within a medicament, the compound of formula (I) is combined with an antibiotic of β-lactamine type chosen from the group constituted by the penams, the penems, the carbapenems, the cephems, the carbacephems, the oxacephems, the cephamycins and the monobactams.

By β-lactamines, is meant for example the penicillins such as amoxicillin, ampicillin, azlocillin, mezlocillin, apalcillin, hetacillin, bacampicillin, carbenicillin, sulbenicillin, ticarcillin, piperacillin, azlocillin, mecillinam, pivmecillinam, methicillin, ciclacillin, talampicillin, aspoxicillin, oxacillin, cloxacillin, dicloxacillin, flucloxacillin, nafcillin or pivampicillin, the cephalosporins such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, latamoxef, the carbapenems such as imipenem, meropenem, biapenem or panipenem and the monobactams such as aztreonam and carumonam, as well as their salts.

The compounds of formula (I) or their pharmaceutically acceptable salts, can be administered at the same time as the dose of an antibiotic of the β-lactamine type, or separately, preferably after it. This can be carried out in the form of a mixture of the two active ingredients or in the form of a pharmaceutical combination of the two separate active ingredients.

The dose of the compounds of formula (I) and of their pharmaceutically acceptable salts can of course vary within wide limits and must naturally be adapted, in each particular case, to the individual conditions and to the pathogenic agent, which produces β-lactamase, to be combated. In general, a daily dose can range from 0.1 to approximately 10 g as may be convenient.

Moreover, the ratio of the β-lactamase inhibitor of formula (I) or of the pharmaceutically acceptable salt of the latter to the antibiotic of β-lactamine type can also varies vary within wide limits and must be adapted, in each particular case, to the individual conditions. In general, a ratio ranging from approximately 1:20 to approximately 1:1 must be indicated.

The medicaments as defined above are employed in the form of pharmaceutical compositions in a mixture with an organic or mineral, inert pharmaceutical excipient, adapted to the sought administration method, and a subject of the invention is also said pharmaceutical compositions.

These compositions can be solid or liquid and be presented in the pharmaceutical forms commonly used in human medicine, such as for example, plain or sugar-coated tablets, gelatin capsules, granules, suppositories, injectable preparations, ointments, creams, gels, they are prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a lyophilisate intended to be dissolved extemporaneously in an appropriate vehicle for example apyrogenic sterile water.

The compounds of formula (I) can be prepared by a process comprising:
a) a stage during which a carbonylation agent, if appropriate in the presence of a base, is reacted with a compound of formula (II):

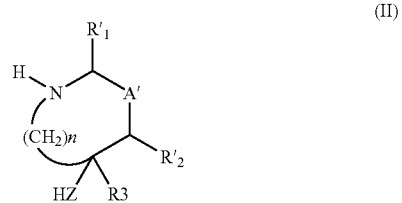

in which:
R'$_1$ represents a hydrogen atom or a CN, protected COOH, COOR', (CH$_2$)$_{n'}$R'$_5$, CONR$_6$R$_7$ or protected

radical;
n', R$_6$ and R$_7$ having the above definitions and
R' and R'$_5$ having the above definitions of R and R$_5$ respectively, in which the reactive functions which are optionally present are protected;
R'$_2$ represents a hydrogen atom or a (CH$_2$)n'$_1$R'$_5$ group, n'$_1$ and R'$_5$ being as defined above;
R$_3$ is as defined previously;
A' represents a bond between the two carbons which carry R'$_1$ and R'$_2$ or a

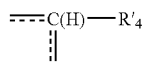

group, R'$_4$ representing a hydrogen atom or a (CH$_2$)n'$_1$R'$_5$ group, n'$_1$ and R'$_5$ being as defined above, the dotted line representing an optional bond with one or other of the carbons which carry substituents R'$_1$ and R'$_2$;
n is as defined previously;
HZ represents a HO—(CH$_2$)n"-, HNR'$_8$—(CH$_2$)$_{n''}$— or HNR'$_8$—O— group, n" being as defined previously and R'$_8$ representing a hydrogen atom, a protected OH, R', OR' radical, a Y' or OY' radical, Y' being chosen from the COH, COR', COOR', CONH$_2$, CONHR', protected CONHOH, CONHSO$_2$R', protected CH$_2$COOH, CH$_2$COOR', protected CH$_2$CONHOH, CH$_2$CONHCN, CH$_2$tetrazole substituted by R', CH$_2$SO$_2$R', CH$_2$PO (OR')$_2$, protected CH$_2$SO$_3$, protected CH$_2$PO(OR')OH, protected CH$_2$PO (R')OH, protected CH$_2$PO(OH)$_2$ groups, a Y'$_1$ or OY'$_1$ radical, Y'$_1$ being chosen from the SO$_2$R', SO$_2$NHCOH, SO$_2$NHCOR', SO$_2$NHCOOR', SO$_2$NHCONH$_2$, SO$_2$NHCONHR' and protected SO$_3$H groups, a Y'$_2$ or OY'$_2$ radical, Y'$_2$ representing a protected PO(OH)$_2$, protected PO(OH)(OR'), protected PO(OH)R' or PO(OR')$_2$ group, or a Y'$_3$ radical, Y'$_3$ being chosen from the protected tetrazole, tetrazole substituted by the R' radical, protected NH or NR' tetrazole, NH or NR' tetrazole substituted by the R' radical, NHSO$_2$R' and NR'SO$_2$R' groups, R' being as defined above;

with a view to obtaining an intermediate compound of formula:

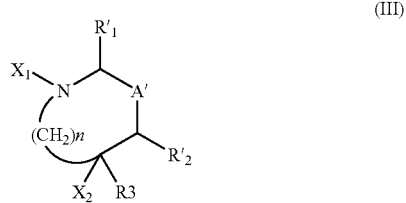

in which:
R'$_1$, R'$_2$, R$_3$, A' and n have the same meanings as above and either X$_1$ is a hydrogen atom and X$_2$ represents a -Z-CO—X$_3$ group, X$_3$ representing the remainder of the carbonylation agent, or X$_2$ is a -ZH group and X$_1$ represents a CO—X$_3$ group, X$_3$ being as defined previously;
b) a stage during which the intermediate obtained previously is cyclized, in the presence of a base; and in that:
c) if appropriate, Stage a) is preceded and/or Stage b) is followed by one or more of the following reactions, in an appropriate order:
protection of the reaction functions,
deprotection of the reaction functions,
esterification,
saponification,
sulphation,
phosphation
amidification,
acylation,
sulphonylation;
alkylation;
introduction of a double bond;
formation of a urea group;
introduction of a tetrazole group;
reduction of the carboxylic acids;
dehydration of amide to nitrile;
salification;
ion exchange;
resolution or separation of diastereoisomers;
oxidation of sulphide to sulphoxide and/or sulphone.

As a carbonylation agent, a reagent can be employed such as phosgene, diphosgene, triphosgene, an aryl chloroformate such as phenyl or p-nitrophenyl chloroformate, an aralkyl chloroformate such as benzyl chloroformate, an alkyl or alkenyl chloroformate such as methyl or allyl chloroformate, an alkyl dicarbonate such as tert-butyl dicarbonate, carbonyldiimidazole and their mixtures.

The reaction preferably takes place in the presence of a base or a mixture of bases which neutralize the acid formed. It can in particular be an amine such as triethylamine, diisopropylethylamine, pyridine, dimethylaminopyridine. However, the operation can also be carried out using the starting product of formula II as base. It is then used in excess. An illustration is given in the experimental part.

If appropriate, the product of formula II is employed in the form of an acid salt, for example a hydrochloride or a trifluoroacetate.

As base in Stage b), amines, or also hydrides, alcoholates, amides or carbonates of alkali or alkaline-earth metals can also be used.

The amines can be chosen for example from the above list.

As hydride, sodium or potassium hydride can in particular be used.

As alkali metal alcoholate, potassium t-butylate is preferably used.

As alkali metal amide lithium bis(trimethylsilyl) amide can in particular be used.

As a carbonate, sodium or potassium carbonate or bicarbonate can in particular be used.

If appropriate, the intermediate of formula III can be obtained in the form of an acid salt generated during the carbonylation reaction and in particular a hydrochloride. It is then employed in the cyclization reaction in this form.

If appropriate, the cyclization can be carried out without isolation of the intermediate of formula III.

The reactions mentioned in Stage c) are generally standard reactions, which are well-known to a person skilled in the art.

The reactive functions which it is convenient and appropriate to protect are carboxylic acid, amine, amide, hydroxy and hydroxylamine functions.

The protection of the acid function is in particular carried out in the form of alkyl esters, allyl, benzyl, benzhydryl or p-nitrobenzyl esters.

Deprotection is carried out by saponification, acid hydrolysis, hydrogenolysis, or also cleavage using soluble complexes of palladium 0.

Examples of these protections and deprotections are provided hereafter in the experimental part.

Protection of the amines and amides is in particular carried out in the form of benzylated derivatives, in the form of carbamates, in particular of allyl, benzyl, phenyl or tertbutyl, or also in the form of silylated derivatives such as tertbutyl dimethyl, trimethyl, triphenyl or also diphenyl tertbutyl-silyl derivatives.

Deprotection is carried out, according to the nature of the protective group, by sodium or lithium in liquid ammonia, by hydrogenolysis or using soluble complexes of palladium 0, by the action of an acid, or by the action of tetrabutylammonium fluoride.

Examples are provided hereafter in the experimental part.

The protection of hydroxylamines is carried out in particular in the form of benzyl or allyl ethers.

Cleavage of the ethers is carried out by hydrogenolysis or by using soluble complexes of palladium 0.

A illustration is provided below in the experimental part.

Protection of the alcohols is carried out in a standard fashion, in the form of ethers, esters or carbonates. The ethers can be alkyl or alkoxyalkyl ethers, preferably methyl or methoxyethoxymethyl ethers, aryl or preferably aralkyl ethers, for example benzyl, or silylated ethers, for example the silylated derivatives mentioned above. The esters can be any cleavable ester known to a person skilled in the art and preferably the acetate, propionate or benzoate or p-nitrobenzoate. The carbonates can be, for example, methyl, tertbutyl, allyl, benzyl or p-nitrobenzyl carbonates.

Deprotection is carried out by means known to a person skilled in the art, in particular, saponification, hydrogenolysis, cleavage by soluble complexes of palladium 0, hydrolysis in acid medium or also, for the silylated derivatives, treatment with tetrabutylammmonium fluoride.

Examples are provided in the experimental part.

The sulphation reaction is carried out by the action of $SO_3$-amine complexes such as $SO_3$-pyridine or $SO_3$-dimethylformamide, operating in pyridine, the salt formed, for example the pyridine salt, can then be exchanged for example by a salt of another amine, of a quaternary ammonium or of an alkali metal. Examples are provided in the experimental part.

The phosphation reaction is carried out for example by the action of a chlorophosphate such as dimethyl, dibenzyl or diphenyl chlorophosphate.

The amidification reaction is carried out starting from the carboxylic acid using an activation agent such as an alkyl chloroformate or EDCI, by the action of ammonium hydroxide or of an appropriate amine or their acid salts. Examples are provided hereafter in the experimental part.

The acylation and sulphonylation reactions are carried out on the hydroxyureas by the action respectively of a halide or an anhydride of an appropriate carboxylic acid or a halide of an appropriate sulphonic acid. Several examples are provided hereafter in the experimental part.

The alkylation reaction is carried out by the action on the hydroxylated derivatives of an alkyl halide or an alkyl halide substituted, in particular, by a free or esterified carboxy radical. Illustrations are provided hereafter in the experimental part.

The final optional introduction of a double bond, which is then preferably situated between the carbon atoms which carry $R_4$ and $R_1$, is carried out by the action of a halogenated derivative of selenium then oxidation, according to the methods known to a person skilled in the art. An example is shown hereafter in the experimental part.

Formation of a urea group, which relates to the substituent $R_8$ is preferably carried out by the action of an appropriate isocyanate on the free NH. An example is shown hereafter in the experimental part.

Introduction of a tetrazole group is carried out by the action of a halogenated derivative, preferably fluorinated, of the protected or substituted tetrazole. Deprotection can be carried out by hydrogenolysis.

Reduction of the acids to alcohols can be carried out by the action of a borane or via a mixed anhydride intermediate, by the action of an alkaline borohydide. The mixed anhydride is prepared for example using an alkyl chloroformate. An illustration of this is provided in the experimental part.

Dehydration of the amide to a nitrile can occur under the carbonylation and cyclization reaction conditions .

Oxidation of the sulphide to sulphoxide and/or sulphone can be carried out by the action of a peracid such as metachloroperbenzoic or perphthalic acid or any other reagent known to a person skilled in he art.

Salification by acids is, if appropriate, carried out by adding an acid in soluble phase to the compound. Salification by bases can concern either the compounds comprising an acid function, in particular carboxy, or those comprising a sulphooxy function or a phosphoric acid derivative or those comprising a heterocycle with an acid character. In the first case, the operation is carried out by adding an appropriate base such as those mentioned previously. In the second case, the pyridinium salt is obtained directly during the action of the $SO_3$-pyridine complex and the other salts are obtained from this pyridinium salt. In one or other case, the operation can also be carried out by ion exchange on resin. Examples of salifications are shown hereafter in the experimental part.

Separation of the enantiomers and diastereoisomers can be carried out according to the techniques known to a person skilled in the art, in particular chromatography.

In addition to the processes described previously, the compounds of formula (I) can of course be obtained by methods which use at the start a compound of formula (II) in which $R'_1$, A', $R'_2$, $R_3$ and HZ have the values which lead directly (without conversion) to those of the compounds that one wishes to prepare. If appropriate, those of these values which would contain reaction functions as mentioned above are then protected, deprotection occurring at the end of the cyclization stage b or at any other opportune moment in the synthesis. The protections and deprotections are then carried out as described above.

Such methods are provided hereafter in the experimental part.

The products of formula (II) are known or can be prepared according to methods known to a person skilled in the art. References from the literature as well as the preparations are provided hereafter in the experimental part.

EXAMPLES

The following examples illustrate the invention, without however limiting the scope.

In the examples which follow the following abbreviations have been used:
DEAD: diethyl azo-dicarboxylate
TEA: triethylamine
DMAP: 4-dimethylamino-pyridine
EDCI: 1-(3-dimethylamino-propyl)-3-ethylcarbo-diimide hydrochloride
THF: tetrahydrofuran
AIBN: 2.2'-azo-bis-isobutyronitrile
M: molar molecular mass
MS: mass spectrometry
EI: electron impact
SIMS: secondary ion mass spectrometry
FAB: fast atom bombardment Example 1 cis diphenylmethyl 7-oxo-6-oxa-1-azabicyclo[3.2.1]octane-4-propanoate 3.16 g (10.6 mmoles) of the hydrochloride of 3-oxo-1-(phenylmethyl)-4-piperidinepropanoic acid (M=297.7 g) (described in the Japanese Patent Application J54098-772) is mixed with 100 ml of ethanol and the reaction medium is cooled down to 10° C. 1.84 g of $NaBH_4$ is added over 15 minutes, under a stream of nitrogen, whilst maintaining the temperature between 8 and 13° C. The temperature is allowed to rise to ambient temperature and left in contact for 1 hour 30 minutes. Another 380 mg of $NaBH_4$ is added and the reaction medium is left overnight at ambient temperature.

The solvent is evaporated off under reduced pressure, followed by taking up in 50 ml of water and adjusting the pH from 10 to 2 using concentrated hydrochloric acid. Evaporation is again carried out under reduced pressure. The solid residue (approximately 10.8 g) is washed twice with 100 ml of ethanol then the solvent is evaporated off under reduced pressure.

In this way 3.10 g of the hydrochloride of 3-hydroxy-1-(phenylmethyl)-4-piperidinepropanoic acid (M=299.7 g) is obtained, which corresponds to a yield of 97%.

3.10 g (10.3 mmoles) of the compound obtained previously is diluted in 100 ml of ethanol then 900 mg of 10% Pd/C by prehydrogenated weight and in 30 ml of ethanol is added to it.

The reaction medium is left under a hydrogen atmosphere at normal pressure overnight, then the catalyst is eliminated by filtration and the ethanol by evaporation under reduced pressure.

1.90 g of the hydrochloride of trans-3-hydroxy-4-piperidinepropanoic acid (M=209.6 g), is obtained i.e. a yield of 88%.

1.79 g (8.54 mmoles) of the compound obtained previously is mixed with 20 ml of ethanol and 20 ml of water.

Then concentrated soda is added until the pH is approximately 8.5.

Then, 1 ml of allyl chloroformate and concentrated soda are added so as to maintain the pH between 8 and 9.

The reaction mixture is extracted with ethyl acetate then the aqueous phase is acidified to pH 2 by adding concentrated hydrochloric acid and reextracting with ethyl acetate. After drying and evaporating the solvent under reduced pressure, 1.69 g of crude product is obtained which is taken up in a mixture of dichloromethane and ethanol, followed by filtering and again evaporating the solvent under reduced pressure.

In this way 1.40 g of trans-3-hydroxy-1-[(2-propenyloxy) carbonyl]-4-piperidinepropanoic acid (M=257 g) is obtained, i.e. a yield of 60%.

3.24 g (12.6 mmoles) of the above hydroxy-acid and 6.4 g of triphenylphosphine are dissolved in 60 ml of THF at 0° C. under a nitrogen atmosphere. Then 2.5 ml of DEAD is added and after 15 minutes the reaction mixture is evaporated under reduced pressure in order to obtain 12 g of crude product. Purification is carried out by chromatography on silica eluting progressively with a mixture of dichloromethane and ethyl acetate 9/1, 8/2, 7/3 in order to separate the cis and trans lactones.

In this way 2.72 g of cis lactone is obtained in a mixture with reduced DEAD and phosphine oxide.

This product is resolubilized in 10 ml of DME and 8 ml of a 1N solution of NaOH is added. After contact for 1 hour, the reaction mixture is extracted twice with ethyl acetate, then acidified to pH 2 with 2N HCl, and reextracted with ethyl acetate. After drying and evaporating the solvent under reduced pressure, 1.07 g of hydroxy-acid is obtained.

1.0 g of crude hydroxy-acid is dissolved in a mixture of 5 ml of dichloromethane and 2 ml of methanol, then treated with an excess of diphenyldiazomethane in dichloromethane, until the starting product disappears. The solvent is evaporated off under reduced pressure and the product is purified by chromatography in order to produce 1.39 g of cis diphenylmethyl 3-hydroxy-1-[(2-propenyloxy)carbonyl]-4-piperidinepropanoate (M=423 g), i.e. an overall yield of 26%.

Then 1.2 g (2.83 mmoles) of the product obtained previously is dissolved under a nitrogen atmosphere in 23 ml of dichloromethane. Then 390 µl of acetic acid then 860 µl of $Bu_3SnH$ and 70 mg of $Pd(PPh_3)_4$ are added.

The solvent is evaporated off under reduced pressure in order to obtain 3.82 g of crude product which is washed with petroleum ether. 1.27 g of product is obtained which is filtered on silica with dichloromethane, then with a mixture of dichloromethane and methanol 95/5 then 90/10. In this way 0.87 g of cis diphenylmethyl 3-hydroxy-4-piperidinepropanoate (M=339 g) is obtained, i.e. a yield of 77%.

400 mg (1.00 mmole) of the compound obtained previously is dissolved in 25 ml of dichloromethane, 80 µl of diphosgene ($Cl_3COCOCl$), 336 µl of TEA, 144 mg of DMAP are added.

The reaction medium is left to react at ambient temperature for 5 hours 30 minutes, then diluted in dichloromethane, followed by washing with a 10% aqueous solution of tartaric acid, then with a buffer solution of sodium phosphate at pH 7. The organic phase is dried over sodium sulphate, then the solvent is evaporated off under reduced pressure. In this way 380 mg of crude product is obtained.

Purification is carried out by chromatography on silica, eluting with a dichloromethane/ethyl acetate mixture 95/5 with 0.1% water.

184 mg of the title compound is obtained (M=365.43 g), i.e. a yield of 50%.

1H NMR

In CDCl3, at 300 MHz, chemical shifts of the peaks in ppm and multiplicity: 1.60 to 1.88 (m): NC$\underline{H}_2$—C$\underline{H}_2$—C$\underline{H}$; 2.48 (m): CH$_2$—C$\underline{H}_2$—CO; 2.78 (d) –2.90 (m) –3.33 to 3.47 (m): C$\underline{H}_2$—N—C$\underline{H}_2$; 4.50 (d): C$\underline{H}$O—CH$_2$; 6.89 (s): CO$_2$C$\underline{H}$(C$_6$H$_5$)2; 7.33 (m): (C$_6$H$_5$)$_2$.

IR (CHCl$_3$): 1784, 1734, 1600, 1585, 1496 cm$^{-1}$

MS(positive electrospray) m/z: [M]$^+$=365

Example 1a cis-7-oxo-6-oxa-1-azabicyclo[3.2.1]octane-4-propanoic acid 176 mg (0.482 mmoles) of the product obtained previously is dissolved in 10 ml of acetone. 90 mg of Pd/C at 10% by weight is added.

The reaction medium is left to react under a hydrogen atmosphere at normal pressure for 3 hours. Another 25 mg of catalyst is added and the reaction is left to continue for 1 hour 15 minutes.

The catalyst is filtered then the solvent is evaporated off under reduced pressure in order to obtain 146 mg of product.

The medium is reacted in 10 ml of acetone with 35 mg of Pd/C at 10% by weight under a hydrogen atmosphere and the reaction is left for 1 hour to complete.

The catalyst is then separated by filtration and the filtrate is evaporated under reduced pressure. 137 mg of crude product is obtained which is crystallized from a mixture of ethyl ether and petroleum ether. In this way 75 mg of the sought product (M=199 g) is obtained, i.e. a yield of 78%.

1H NMR

In CDCl3, at 250 MHz, chemical shifts of the peaks in ppm and multiplicity: 1.30 to 1.63 (m) and 1.88 (m): NC$\underline{H}_2$—C$\underline{H}_2$—C$\underline{H}$; 2.25 (t): CH$_2$—C$\underline{H}_2$—CO; 3.06 (m) and 3.38 (m): C$\underline{H}_2$—N—C$\underline{H}_2$; 4.65 (d): C—C$\underline{H}$O—CH$_2$; 12.08 (s): mobile H.

IR (Nujol): 1785, 1717 cm$^{-1}$

MS (FAB) m/z: [M+H]$^+$=200; 159

Example 2

Trans diphenylmethyl 7-oxo-6-oxa-1-azabicyclo[3.2.1]octan-4-acetate 94 mg (0.259 mmoles) of the compound trans diphenylmethyl 3-hydroxy-4-piperidine-acetate hydrochloride (M=361.87 g) (described in Eur. J. Med. Chem—Chim. Ther—1982—17(6)531-5) and 7 ml of dichloromethane are mixed under an inert atmosphere.

The reaction medium is cooled down using an ice bath and 19 µl of diphosgene is injected. Agitation is carried out for 25 minutes, then 72 µl of TEA is injected. Agitation is carried out at ambient temperature for 30 minutes and the solvent is evaporated off under reduced pressure, followed by taking up in 7 ml of toluene.

36 µl of TEA then 31 mg of DMAP are added.

Heating is carried out for 15 minutes at 100° C., then the reaction medium is left to return to ambient temperature, followed by washing twice with 4 ml of 10% tartaric acid in water, then with 4 ml of water saturated with sodium chloride.

After drying over magnesium sulphate, filtration is carried out and the solvent is evaporated off under reduced pressure.

78 mg of an oil is obtained which is chromatographed on silica, eluting with a 95/5 mixture of dichloromethane and ethyl acetate.

In this way 35.7 mg of expected compound (M=351.405 g) is obtained, in the form of white crystals, i.e. a yield of 39%.

Example 2a trans-7-oxo-6-oxa-1-azabicyclo[3.2.1]octan-4-acetic acid 38.7 mg (0.110 mmoles) of the product obtained in Example 2 as well as 2 ml of acetone and 38 mg of Pd/C catalyst at 10% by weight are mixed together under an inert atmosphere.

The reaction medium is placed under a hydrogen atmosphere at normal pressure.

The reaction medium is left to react for 45 minutes, then the catalyst is eliminated by filtration and the solvent is evaporated off under reduced pressure.

In this way 32.6 mg of crude product is obtained.

Recrystallization is carried out from ethyl ether in order to obtain 14.2 mg of white crystals of expected compound (C$_8$H$_{10}$NO$_4$—M=185.181 g), i.e. a yield of 69%.

Example 3 cis diphenylmethyl 7-oxo-6-oxa-1-azabicyclo[3.2.1]octan-4-acetate 1.5 g (5.78 mmoles) of trans-1-[(1,1-dimethylethoxy)carbonyl]-3-hydroxy-4-piperidineacetic acid (described in Eur. J. Med. Chem—Chim. Ther—1982—17(6)531-5), 7 ml of dichloromethane, 3.03 g of triphenylphosphine and 22 ml of tetrahydrofuran are mixed together.

A solution of 0.91 ml of DEAD in 2.5 ml of tetrahydrofuran is added. The reaction medium is left to react for 3 hours 20 minutes, then 8.7 ml of 1N soda is added and agitation is carried out for 1 hour 15 minutes.

The reaction mixture is extracted twice with ethyl acetate, then the pH is adjusted to 2 with 2N hydrochloric acid, followed by extracting three times with ethyl acetate.

The organic phases are combined and washed with water saturated in sodium chloride, then dried over magnesium sulphate, filtered and the solvent is evaporated off under reduced pressure.

In this way 1.37 g of white crystals of 1,1-dimethylethyl (3a.alpha.,7a.alpha.)-hexahydro-2-oxo-furo[2,3-c]pyridine-6(2H)-carboxylate (C$_{12}$H$_{21}$NO$_5$—M=259.304 g) is obtained, i.e. a yield of 91%.

1.37 g (5.28 mmoles) of the compound obtained previously and 32 ml of dichloromethane are mixed together under an inert atmosphere.

An excess of a solution of diphenyldiazomethane in dichloromethane is introduced, until the starting product disappears.

Then the solvent is evaporated off under reduced pressure and in this way 2.81 g of crude product is obtained which is purified by chromatography on silica, using dichloromethane, then a 95/5 mixture of dichloromethane/ethyl acetate as eluent.

2.00 g of white crystals of cis diphenylmethyl 1-[(1,1-dimethylethoxy)carbonyl]-3-hydroxy-4-piperidineacetate is obtained, (M=425.528 g), i.e. a yield of 89%.

0.6 g (1.41 mmoles) of the compound obtained previously and 1.93 ml of a solution of hydrogen chloride in methanol at 7.3 mol/l is introduced, Agitation is carried out at ambient temperature and after 15 minutes, 1 ml of dichloromethane is added.

After another 15 minutes, the reaction medium is evaporated under reduced pressure.

Dichloromethane is again added then, evaporation is carried out. This operation is repeated several times.

Then the product is crystallized from ethyl ether.

In this way 0.44 g of the hydrochloride of cis diphenylmethyl 3-hydroxy-4-piperidineacetate is obtained of molecular formula, $C_{20}H_{23}NO_3$,HCl (M=361.871 g), i.e. a yield of 86%.

This reaction also leads to the formation of variable quantities of the lactone hydrochloride of (3a.alpha.,7a.alpha.)-hexahydro-furo[2,3-c]pyridin-2(3H)-one, (M=177.6 g).

0.28 g (0.77 mmoles) of compound $C_{20}H_{23}NO_3$, HCl obtained previously and 19 ml of dichloromethane are mixed together under an inert atmosphere.

60 μl of diphosgene is added at 0° C. and agitation is carried out. After 25 minutes 0.32 ml of TEA is introduced. Then 94 mg of DMAP is added and the reaction medium is left to return to ambient temperature.

Agitation is carried out for 4 hours 15 minutes, followed by washing successively with a 10% aqueous solution of tartaric acid then with water saturated with sodium chloride, followed by drying over magnesium sulphate, filtering and the solvent is evaporated off under reduced pressure.

In this way 0.265 g of expected compound of molecular formula $C_{21}H_{21}NO_4$ (M=351.405 g) is obtained, i.e. a yield of 98%.

1H NMR

In CDCl3, at 250 MHz, chemical shifts of the peaks in ppm and multiplicity: 1.82 (m): $NCH_2$—$C\underline{H}_2$; 2.30 to 2.70 (m): CO—$CH_2$—CH; 2.93 (d) -2.99 (dt) and 3.45 (m): $C\underline{H}_2$—N—$CH_2$; 4.60 (d): CH—$C\underline{H}O$—$CH_2$; 6.87 (S): $CO_2C\underline{H}(C_6H_5)_2$; 7.10 to 7.35 (m): $(C_6\underline{H}_5)_2$.

IR (CHCl3)=1786, 1734; 1600, 1587, 1496 cm$^{-1}$.

MS (SIMS) m/z: $[M+Na]^+$=374$^+$.

Example 3a cis-7-oxo-6-oxa-1-azabicyclo[3.2.1]octan-4-acetic acid 55 mg (0.156 mmoles) of the product obtained in Example 3, 3 ml of ethyl acetate and 55 mg of Pd/C catalyst at 10% by weight are mixed together.

The reaction medium is placed under a hydrogen atmosphere at normal pressure.

The reaction medium is left to react for 1 hour 30 minutes, then the catalyst is filtered out and the solvent is evaporated off under reduced pressure.

In this way 38 mg of crude product is obtained which is crystallized from a mixture of pentane and ethyl ether.

In this way 16 mg of white crystals of expected compound (M=185.181 g) is collected, i.e. a yield of 55%.

1H NMR

In CDCl3, at 250 MHz, chemical shifts of the peaks in ppm and multiplicity: 1.63 to 1.86 (m) and 1.91 (m): $NCH_2$—$C\underline{H}_2$; 2.27 to 2.49 (m) and 2.54 (dd): CO—$C\underline{H}_2$—CH; 2.98 (d) and 3.54 (d): $C\underline{H}_2$—N—$CH_2$—$CH_2$; 3.04 (dt) and 3.41 (dd): $CH_2$—N—$C\underline{H}_2$—$CH_2$; 4.71 (d): CH—$C\underline{H}O$—$CH_2$.

IR (Nujol): 1784, 1734, 1686 cm$^{-1}$.

MS (SIMS) m/z: $[M+H]^+$=186$^+$, 167$^+$.

Example 3b cis methyl 7-oxo-6-oxa-1-azabicyclo[3.2.1]octan-4-acetate 78 mg (0.421 mmoles) of the compound obtained in Example 3a is then dissolved in 1 ml of dichloromethane.

An excess of diazomethane is added dropwise until a yellow colouration subsists, then the solvent is evaporated off under reduced pressure.

In this way 80 mg of crude product is obtained which is purified by chromatography on silica, eluting with a dichloromethane/ethyl acetate mixture 95/5.

In this way 8.2 mg of expected compound (M=199.208 g) is obtained i.e. a yield of 10%.

Example 4 cis-7-oxo-6-oxa-1-azabicyclo[3.2.1]octan-4-acetonitrile 67 mg (0.38 mmoles) of the hydrochloride of (3a.alpha., 7a.alpha.)-hexahydro-furo[2,3-c]pyridin-2(3H)-one, (M=177.6 g) prepared in Example 3 is dissolved in 1 ml of a solution of ammonia at 4.17 mol/l in methanol.

Agitation is carried out for 5 hours, the solvent is evaporated off under reduced pressure, then another 1 ml of the solution of ammonia in methanol is added and the reaction is left to continue for 18 hours.

The solvent is evaporated off under reduced pressure and in this way 79 mg of cis-3-hydroxy-4-piperidineacetamide of molecular formula C7H14O2N2 (M=158 g) is obtained.

75 mg of the compound obtained above is mixed under an inert atmosphere in solution in 9 ml of dichloromethane.

The reaction medium is cooled down with an ice bath and 30 μl of diphosgene is introduced.

The reaction medium is maintained at 0-5° C. for 40 minutes, then 0.16 ml of TEA is introduced and after 5 minutes, 46 mg of DMAP is introduced.

Agitation is carried out for 4 hours at ambient temperature, followed by washing twice with 2 ml of 10% tartaric acid in water, then with 2 ml of a saturated aqueous solution of sodium chloride .

After drying over MgSO4 and filtering, the solvent is evaporated off under reduced pressure. In this way 35 mg of crude product is obtained which is taken up in an ethyl acetate and dichloromethane mixture 30/70. The impurities are filtered out and the filtrate is evaporated under reduced pressure.

In this way 23 mg of expected compound (M=166.18 g) is obtained in the form of an oil, i.e. a yield of approximately 26%.

IR (Nujol): 2241, 1777 cm$^{-1}$.

MS (EI) m/z: $[M]^+$=166, 137, 82, 55, 42.

Example 5

3-benzoyl-1,3-diazabicyclo[2.2.1]heptan-2-one 1.01 g (5.43 mmoles) of 1,1-dimethylethyl 3-amino-1-pyrrolidinecarboxylate (M=186.25 g) (described in the Patent Application WO 9801426) and 10 ml of dichloromethane are mixed under an inert atmosphere, the solution is cooled down to 0° C., then 0.76 ml of TEA. is added dropwise.

Agitation is carried out for 15 minutes whilst maintaining the temperature at 0° C., then 0.63 ml of benzoyl chloride is added.

The reaction medium is left to return to ambient temperature, then diluted by adding 10 ml of dichloromethane, followed by washing with a 10% aqueous solution of tartaric acid, then with 10 ml of water, drying over magnesium sulphate, filtering and the dichloromethane is eliminated by evaporation under reduced pressure.

In this way 1.30 g of 1,1-dimethylethyl 3-(benzoylamino)-1-pyrrolidinecarboxylate (M=292.36 g) is obtained in the form of a yellow oil. The corresponding yield is 82%.

1.30 g (4.46 mmoles) of this compound is mixed with 10 ml of methanol.

The solution is cooled down to 0° C., then 6.12 ml of a solution of hydrogen chloride at 7.3 moles/l in methanol is introduced progressively.

Then the solvent is evaporated off under reduced pressure.

In this way 1.01 g of N-(3-pyrrolidinyl)-benzamide hydrochloride (M=226.707 g) is obtained in the form of oil brown, i.e. a yield close to 100%.

1.01 g (4.46 mmoles) of the compound obtained previously, as well as 10 ml of dichloromethane are mixed under an inert atmosphere.

The reaction medium is cooled down to 0° C., then 1.36 ml of TEA is added dropwise.

Agitation is carried out for 15 minutes, then 1.44 ml of diphosgene is added dropwise.

The reaction medium is maintained at 0° C. for 30 minutes, then left to return to ambient temperature, followed by diluting with dichloromethane, washing with a 10% aqueous solution of tartaric acid, then with water, drying over magnesium sulphate, filtering and concentrating the solvent by evaporating under reduced pressure in order to obtain 0.615 g of crude product.

Purification is carried out by chromatography on silica eluting with a dichloromethane/acetone mixture 90/10.

In this way 0.320 g of the chloride of 3-(benzoylamino)-1-pyrrolidinecarboxylic acid is recovered which crystallizes. The corresponding yield is 28%.

Then 0.585 g (2.31 mmoles) of the preceding compound is dissolved under an inert atmosphere in 18 ml of tetrahydrofuran.

The solution is cooled down to −78° C., then 2.55 ml of a 1 M solution of lithium bis(trimethyl-silyl) amide in tetrahydrofuran is added dropwise.

A yellow solution is obtained which is maintained at −78° C. for 20 minutes, then agitation is continued for 1 hour whilst allowing the temperature to rise. 350 µl of acetic acid, then 5 ml of a 10% solution of tartaric acid in water are added at 0° C., followed by diluting with ethyl acetate then washing with a 10% solution of tartaric acid then with a solution of phosphate buffer at pH=7, then with water.

The organic phase is dried over magnesium sulphate, followed by filtering and concentrating the solvent by evaporating under reduced pressure.

In this way 0.315 g of crude product is obtained in the form of a yellow solid.

This crude product is purified by chromatography on silica eluting with a dichloromethane and ethyl acetate mixture 90/10.

In this way 0.140 g of expected compound $C_{12}H_{12}N_2O_2$, (M=216.24 g) is recovered in the form of a white solid, i.e. a yield of 28%.

IR (CHCl$_3$): 1801, 1775, 1675; 1620, 1603, 1582 cm$^{-1}$.

MS (positive electrospray) m/z: [M]$^+$=216, 105, 77.

Example 6

Potassium salt of trans-6-[(phenylmethoxy)carbonyl]-2-oxo-1,3-diazabicyclo[2.2.1]heptan-3-acetic acid 1 g (3.12 mmoles—M=186.25 g) of trans 1-(1,1-dimethylethyl) and 2-(phenylmethyl) 4-amino-1,2-pyrrolidinedicarboxylate (described in J. Org. Chem. 1991, 56, 3009-3016), 10 ml of tetrahydrofuran, 560 µl of allyl bromoacetate and 660 µl of TEA are mixed together.

The reaction medium is left to react under agitation at ambient temperature for 14 hours, then for 3 hours at 50° C., followed by diluting with ethyl acetate and washing with a 10% aqueous solution of tartaric acid, then with a saturated aqueous solution of sodium chloride.

The organic phase is dried over magnesium sulphate, filtered then the solvent is evaporated off under reduced pressure.

In this way 1.21 g of crude product is obtained which is purified by chromatography on silica, eluting with a 80/20 mixture of dichloromethane and ethyl acetate.

0.99 mg of trans 1-(1,1-dimethylethyl) and 2-(phenylmethyl) 4-[[[(2-propenyloxy)carbonyl]methyl]amino]-1,2-pyrrolidine dicarboxylate of molecular formula $C_{12}H_{30}N_2O_6$ (M=418 g) is obtained.

6 ml of a 4 M solution of hydrogen chloride in ethyl acetate is added under a nitrogen atmosphere and at 0° C. to 0.99 g (2.36 mmoles) of the compound obtained previously. The reaction medium is left to react at ambient temperature for 15 minutes.

The solvent is evaporated off under reduced pressure. A crude product is obtained which is crystallized from ethyl ether in order to obtain 0.95 g of the dihydrochloride of trans phenylmethyl 4-[[[(2-propenyloxy)carbonyl]methyl]amino]-2-pyrrolidinecarboxylate,of molecular formula $C_{17}H_{23}N_2O_4$, 2HCl (M=394 g).

0.5 g of this product is dissolved in 20 ml of dichloromethane and 1.3 ml of 2N soda and 3 ml of water are added. The reaction medium is left to settle, followed by extracting with dichloromethane, drying over magnesium sulphate, then filtering and the solvent is evaporated off under reduced pressure.

In this way 339 mg of free diamine is obtained. The corresponding yield is 83%.

100 mg (0.314 mmoles) of the diamine obtained previously is dissolved in 5 ml of acetonitrile at 0° C. and under a nitrogen atmosphere.

21 µl of diphosgene is added. After 15 minutes of contact, this solution is added, under a nitrogen atmosphere and over 4 hours, to a mixture containing 38 mg of DMAP, 88 µl of TEA in 10 ml of acetonitrile heated to 70° C.

After the addition has ended, the reaction mixture is heated again for one hour, then cooled down, diluted with ethyl acetate and washed successively with a 10% aqueous solution of tartaric acid, then with a saturated aqueous solution of sodium chloride. After drying over sodium sulphate, filtering and evaporating the solvents under reduced pressure, 58 mg of crude product is obtained. This product is purified by chromatography on silica eluting with a dichloramethane/ethyl acetate mixture 8/2 in order to produce 19 mg of trans 2-propenyl 6-[(phenylmethoxy)carbonyl]-2-oxo-1,3-diazabicyclo[2.2.1]heptan-3-acetate of molecular formula $C_{18}H_{20}N_2O_5$ (M=344.57 g), i.e. a yield of 17%.

Then 24 mg (0.069 mmoles) of the preceding compound is dissolved in 250 µl of dichloromethane. 3 mg of Pd(PPh$_3$)$_4$ is introduced under a nitrogen atmosphere, then 150 µl of a 0.5

M solution of potassium ethyl-2-hexanoate in ethyl acetate is added. After a few minutes, a precipitate forms which is centrifuged and washed twice with 500 µl of ethyl acetate.

24 mg of expected compound $C_{15}H_{15}KN_2O_5$ (M=342 g) is obtained, i.e. a quantitative yield.

1H NMR

In DMSO, at 300 MHz, chemical shifts of the peaks in ppm and multiplicity: 1.83 (ddd) and 2.56: N—$CH_2$—CHN—C$H_2$; 2.50 and 2.79 (d): N—$CH_2$—CHN—$CH_2$; 3.23 (d) and 3.41 (d): =C—N—$CH_2$—C=O; 3.62 (ddd): O=C—C$HN$—$CH_2$; 4.13 (s): N—$CH_2$—C$HN$—$CH_2$; 5.16 (s): =C—O—$CH_2$—$C_6H_5$; 7.38 (m): $C_6H_5$—$CH_2$.

MS (positive electrospray) m/z: $[2MK+H]^+$=723, $[2MK+Na]^+$=707, $[MK+K]^+$=381, $[MK+Na]^+$=365; $[MK+H]^+$=343.

Example 7 trans methyl 3-benzoyl-2-oxo-1,3-diazabicyclo[2.2.1]heptane-6-carboxylate 0.471 g (1.93 mmole) of trans 1-(1,1-dimethylethyl) and 2-methyl 4-amino-1,2-pyrrolidinedicarboxylate (described in J. Org. Chem. 1991, 56, 3009-3016) and 3.5 ml of dry dichloromethane to dissolve it are mixed under a nitrogen atmosphere.

The solution is cooled down to 0° C., then 269 µl of TEA is added dropwise.

Agitation is carried out for 15 minutes whilst maintaining at 0° C., then 224 µl of benzoyl chloride is added dropwise.

The reaction medium is left and the temperature returns to 20° C. over one hour, followed by diluting with 30 ml of dichloromethane, washing with a 10% aqueous solution of tartaric acid, then with a saturated solution of sodium bicarbonate, then with water, drying over magnesium sulphate, filtering, concentrating by evaporating the dichloromethane under reduced pressure.

In this way 0.6 g of a yellow oil is obtained which is purified by chromatography on silica using a dichloromethane/methanol mixture 99/1 as eluent.

In this way 0.499 g of trans 1-(1,1-dimethylethyl) and 2-methyl 4-(benzoylamino)-1,2-pyrrolidine dicarboxylate of molecular formula $C_{18}H_{24}N_2O_5$ (M=348 g) is recovered, i.e. a yield of 74%.

0.400 g (1.15 mmole) of the compound obtained previously with 3 ml of ethyl acetate to dissolve the compound are mixed under a nitrogen atmosphere, then the solution is cooled down to 0° C., 2.89 ml of a solution of 4 mole/l of HCl in ethyl acetate is added.

At the end of 15 minutes, agitation is continued at ambient temperature for 1 hour.

Then the solvent is eliminated by evaporation under reduced pressure.

In this way 0.350 g of the hydrochloride of trans methyl 4-(benzoylamino)-2-pyrrolidinecarboxylate of molecular formula $C_{13}H_{15}N_2O_3$, HCl (M=284.744 g) is obtained in the form of a beige solid.

0.327 g (1.15 mmole) of the compound obtained previously, placed under a nitrogen atmosphere, is mixed with 4 ml of dichloromethane.

The suspension is cooled down to 0° C., then 352 µl of TEA is added. Agitation is carried out for 15 minutes at 0° C., then 138 µl of diphosgene is added. Agitation is continued for 5 minutes at 0° C., then the reaction mixture is left to return to ambient temperature and left to react for 30 minutes, followed by diluting with dichloromethane and washing with a 10% aqueous solution of tartaric acid, then with water and drying over magnesium sulphate.

After filtering, the solvent is eliminated by evaporation under reduced pressure. In this way 0.360 g of crude product is obtained which is purified by chromatography on silica eluting with a dichloromethane/acetone mixture 95/5.

In this way 93.7 mg of the hydrochloride of trans methyl 4-(benzoylamino)-1-(chlorocarbonyl)-2-pyrrolidine carboxylate ($C_{14}H_{14}N_2O_4$, HCl (M=310.74 g) is recovered, i.e. a yield of 26%.

93.7 mg (0.301 mmole) of the compound obtained previously, is mixed under a nitrogen atmosphere, with 3 ml of tetrahydrofuran. The temperature of the solution is lowered to −78° C., then 332 µl of lithium bis(trimethylsilyl)amide in a 1M solution in tetrahydrofuran is added dropwise and the reaction medium is maintained at −78° C. for another 5 minutes.

Agitation is carried out for 30 minutes at ambient temperature.

Then the solution is cooled down to 0° C., and 55 µl of acetic acid is added. 20 ml of ethyl acetate and 3 ml of a phosphate buffer at pH=7.0 are added. The reaction medium is left to settle, followed by washing with water, drying over magnesium sulphate, filtering and concentrating by evaporation. In this way 76 mg of a foam is obtained which is purified by chromatography on silica eluting with a dichloromethane/acetone mixture 97/3.

5 mg of pure expected compound, of molecular formula ($C_{14}H_{14}N_2O_4$, HCl (M=274.279 g), is recovered i.e. a yield of 6%.

IR (CHCl$_3$): 1805, 1779, 1743, 1669; 1603, 1589, 1486 cm$^{-1}$.

MS (EI) m/z: $[M]^+$=274, 215, 169, 105, 77.

Example 7a trans phenylmethyl 3-benzoyl-2-oxo-1,3-diazabicyclo[2.2.1]heptane-6-carboxylate The operation is carried out in a similar fashion to that indicated in Example 7, starting from 0.92 g of trans 1-(1,1-dimethylethyl) and 2-phenylmethyl 4-amino-1,2--pyrrolidinedicarboxylate (described in J. Org. Chem. 1991, 56, 3009-3016) in order to obtain the expected compound with an overall yield of 5.4% over 4 stages.

Example 8 trans phenylmethyl 2-oxo-3-(phenylsulphonyl)-1,3-diazabicyclo[2.2.1]heptane-6-carboxylate 2.97 g (9.26 mmoles) of trans 1-(1,1-dimethylethyl) and 2-(phenylmethyl) 4-amino-1,2-pyrrolidinedicarboxylate (described in J. Org. Chem. 1991, 56, 3009-3016) of molecular formula $C_{17}H_{24}N_2O_4$ (M=320.392 g) is mixed under a nitrogen atmosphere and 25 ml of dichloromethane is added. The reaction medium is cooled down to 5° C. and 1.3 ml of TEA is added. Agitation is carried out for 10 minutes and then 1.63 g of benzenesulphonyl chloride is added.

The reaction medium is left under agitation at 5° C. for 15 minutes, then the temperature of the reaction medium is allowed to rise to 20° C. for a duration of 45 minutes, followed by diluting with dichloromethane, washing with a 10% aqueous solution of tartaric acid, then with phosphate buffer at pH=7.0, then with a saturated aqueous solution of sodium chloride, drying over magnesium sulphate and the solvent is evaporated off under reduced pressure.

In this way 4.5 g of crude product is obtained which is chromatographed on silica eluting with a 90/10 mixture of dichloromethane and ethyl acetate.

In this way 4.06 g of trans 1-(1,1-dimethylethyl) and 2-(phenylmethyl) 4-[(phenylsulphonyl)amino]-1,2-pyrrolidinedicarboxylate of molecular formula $C_{23}H_{28}N_2O_6S$ (M=460, 552 g) is recovered, which corresponds to a yield of 95%.

3.83 g (8.31 mmoles) of the sulphonamide obtained previously is mixed with 10 ml of anhydrous methanol.

The solution is cooled down to 0° C. and 8.2 ml of a solution of 10 mol/l of hydrochloric acid in methanol is added at this temperature.

Agitation is maintained at 0° C. for 5 minutes, then the temperature is allowed to rise until at ambient temperature.

After 30 minutes, the methanol is evaporated off under reduced pressure, followed by taking up several times in methanol then in dichloromethane. Then the hydrochloride is crystallized from ethyl ether.

In this way 3.2 g of the hydrochloride of trans phenylmethyl 4-[phenylsulphonyl)amino]-2-pyrrolidinecarboxylate, of molecular formula $C_{18}H_{20}N_2O_4S$, HCl (M=396.896 g) is obtained, which corresponds to a yield of 96%.

2.78 g (7 mmoles) of the hydrochloride obtained previously under an inert atmosphere is mixed with 28 ml of dichloromethane.

The reaction medium is cooled down to about 0-5° C., then 2.15 ml of TEA is added.

Agitation is continued for 15 minutes at a temperature comprised between 0 and 5° C., then 0.46 ml of diphosgene is added.

The reaction medium is maintained at this temperature for 4 minutes, then a 10% aqueous solution of tartaric acid is added, followed by diluting with dichloromethane, decanting, washing with a saturated aqueous solution of sodium chloride, drying over magnesium sulphate, and concentrating under reduced pressure.

In this way 3.1 g of a yellow oil is obtained which is purified by chromatography on silica, eluting with a dichloromethane/ethyl acetate mixture 9/1.

1.82 g of trans phenylmethyl 1-(chlorocarbonyl)-4-[(phenylsulphonyl)amino]-2-pyrrolidinecarboxylate of molecular formula $C_{19}H_{19}ClN_2O_5S$ (M=422.89 g) is recovered, which corresponds to a yield of 61%.

1.81 g (4.28 mmoles) of the carbamoyl chloride obtained previously is mixed under an inert atmosphere with 31 ml of tetrahydrofuran.

The solution obtained is cooled down to −70° C., then 4.7 ml of a 1M solution of lithium bis(trimethylsilyl)amide in tetrahydrofuran is added at this temperature over 10 minutes.

Agitation is carried out for 45 minutes at −70° C., then the temperature of the reaction medium is allowed to rise to about 0° C. The reaction medium is maintained at this temperature for 2 hours 30 minutes.

Then 295 μl of acetic acid is added, followed by diluting with dichloromethane, washing with a 10% aqueous solution of tartaric acid, with a solution of phosphate buffer at pH=7 and with a saturated aqueous solution of sodium chloride, drying over magnesium sulphate and concentrating to dryness under reduced pressure.

The crude product is purified by chromatography on silica, eluting with a dichloromethane/ethyl acetate mixture 95/5.

In this way 244 mg of expected compound of molecular formula $C_{19}H_{18}N_2O_5S$ (M=386.429 g) is obtained, which corresponds to a yield of 14%.

1H NMR

In CDCl3, at 400 MHz, chemical shifts of the peaks in ppm and multiplicity: 2.15 (m): O=C—CH—C$\underline{H}_2$; 2.85 (d) and 3.08 (d): O=C—N—C$\underline{H}_2$; 3.62 (m): O=C—C$\underline{H}$—N—CH$_2$; 4.94 (s): O$_2$S—N—C$\underline{H}$—CH$_2$; 5.16: CO$_2$C$\underline{H}_2$C$_6$H$_5$; 7.34 (m): C$_6\underline{H}_5$; 7.57 (m) −7.68 (m) and 8.03(m): SO$_2$C$_6\underline{H}_5$.

IR (CHCl$_3$): 1780, 1743; 1586, 1499 cm$^{-1}$.

MS (positive electrospray) m/z: [2M+Na]$^+$=795; [M+Na+CH$_3$CN]$^+$=450; [M+Na]$^+$=409; [M+H]$^+$=387.

Example 9 trans phenylmethyl 3-benzoyl-4-methyl-2-oxo-1,3-diazabicyclo[2.2.1]heptane-6-carboxylate 18.69 g (58.52 mmoles) of 1-(1,1-dimethyl-ethyl) and 2-(phenylmethyl) 4-oxo-1,2 pyrrolidinedicarboxylate (described in Chem. Pharm. Bull. 43(8)1302-1306 (1995)) of molecular formula $C_{17}H_{21}NO_5$ (M=319.361 g) and 500 ml of anhydrous ethyl ether are mixed together under an inert atmosphere.

A suspension of 10 g of CeCl3 in 50 ml of anhydrous ethyl ether is added to the solution obtained.

The suspension is agitated for 30 minutes to 20° C., then is cooled down to −60° C.

Then 20 ml of 3 M solution of MeMgBr in ethyl ether is added.

The reaction medium is left to react for 1 hour at −60° C., then the temperature is allowed to rise to 0° C. over 30 minutes, followed by neutralizing with a 10% aqueous solution of NH$_4$Cl, extracting with dichloromethane, filtering, washing the organic phase with water, drying over magnesium sulphate, and concentrating to dryness under reduced pressure.

In this way 19.33 g of an oil is obtained which is purified by chromatography on silica eluting with a dichloromethane/tbutylmethyl-ether mixture 90/10.

7.21 g of cis 1-(1,1-dimethylethyl) and 2-(phenylmethyl) 4-hydroxy-4-methyl-1,2-pyrrolidine dicarboxylate of molecular formula $C_{18}H_{25}NO_5$ (M=335.404 g) is obtained, i.e. a yield of 36%, as well as 2.5 g of the alcohol epimer.

3.17 g (9.45 mmoles) of the compound obtained previously and 70 ml of dichloromethane are mixed together under an inert atmosphere. The reaction medium is cooled down to 5° C. and 2.3 ml of TEA, then 1.28 ml of methane sulphonyl chloride are added dropwise.

Agitation is carried out for 45 minutes at 5° C., followed by washing with a 10% aqueous solution of tartaric acid, then with a solution of phosphate buffer at pH 7, then with water.

The organic phase is dried over magnesium sulphate and concentrated to dryness under reduced pressure.

In this way 3.9 g of an oil is obtained which is purified by chromatography on silica eluting with a dichloromethane/ethyl acetate mixture 90/10.

2.75 g of cis 1-(1,1-dimethylethyl) and 2-(phenylmethyl) 4-methyl-4-[(methylsulphonyl)oxy]-1,2-pyrrolidine dicarboxylate of molecular formula $C_{19}H_{27}NO_7S$ (M=413.494 g) is recovered which corresponds to a yield of 70%.

A solution of 2.54 g (6.14 mmoles) of the mesylate obtained previously in 40 ml of dimethylformamide is prepared.

Then, 519 mg (7.98 mmoles) of NaN$_3$ is added at 20° C. followed by heating at 50° C. for 2 hours. After cooling down, the reaction medium is poured into 250 ml of water and extracted with 250 ml of dichloromethane. The organic phase is washed with water, dried over magnesium sulphate and evaporated to dryness under reduced pressure.

2.4 g of crude product is obtained which is purified by chromatography on silica, eluting with a dichloromethane/ethyl acetate mixture 95/5.

In this way 1.66 g of trans 1-(1,1-dimethylethyl) and 2-(phenylmethyl) 4-azido-4-methyl-1,2-pyrrolidine dicarboxylate of molecular formula $C_{18}H_{24}N_4O_4$ (M=360.42 g) is recovered (titring approximately 30% by weight), which corresponds to a yield of approximately 25%.

1.85 g of the azide obtained previously (i.e. approximately 1.7 mmole) is dissolved in 18 ml of toluene.

Then, 1.38 ml of Bu3SnH and 84 mg of AIBN are added at 20° C.

The reaction medium is taken to 75° C. and maintained at this temperature for 2 hours.

The toluene is evaporated off and redissolving is carried out in ethyl acetate. A saturated aqueous solution of potassium fluoride is added and agitation is carried out for 30 minutes at ambient temperature, followed by filtering on clarcel, leaving to settle and drying the organic phase over magnesium sulphate.

After evaporation of the solvent under reduced pressure, 3 g of an oil is obtained which is chromatographed on silica, eluting with a dichloromethane/methanol mixture 9/1.

560 mg of trans 1-(1,1-dimethylethyl) and 2-(phenylmethyl)-4-amino-4-methyl-1,2-pyrrolidine dicarboxylate of molecular formula $C_{18}H_{26}N_2O_4$ (M=334.419 g) is recovered. The yield is therefore quantitative.

578 mg (1.72 mmoles) of the amine obtained previously is mixed under an inert atmosphere in 30 ml of dichloromethane.

The reaction medium is cooled down to 5° C. and 290 µl of TEA, then 240 µl of benzoyl chloride are added dropwise.

Agitation is continued at 5° C. for 30 minutes, followed by diluting with dichloromethane, washing with a 10% aqueous solution of tartaric acid, with a saturated aqueous solution of sodium carbonate, then with water, drying the organic phase over magnesium sulphate, and evaporating the solvent under reduced pressure.

In this way 950 mg of an oil is obtained which is purified by chromatography eluting with a dichloromethane/ethyl acetate mixture 90/10.

In this way 732 mg of trans 1-(1,1-dimethylethyl) and 2-(phenylmethyl) 4-(benzoylamino)-4-methyl-1,2-pyrrolidinedicarboxylate of molecular formula $C_{25}H_{30}N_2O_5$. (M=438.528 g) is recovered, which corresponds to a yield of 97%.

636 mg (1.45 mmoles) of the amide obtained previously is dissolved in 1.9 ml of ethyl acetate, the reaction medium is cooled to about 0-5° C. with an ice bath, then 3.2 ml of a solution of hydrogen chloride at 4.6 mol/l in ethyl acetate is added.

The temperature of the reaction medium is left to rise to 20° C., then after 1 hour, the solvent is evaporated off under reduced pressure.

Then the hydrochloride crystallizes from ethyl ether.

In this way 570 mg of the hydrochloride of trans phenylmethyl 4-(benzoylamino)-4-methyl-2-pyrrolidine carboxylate of molecular formula $C_{20}H_{22}N_2O_3$,HCl (M=374.87 g) is recovered, in the form of a white powder. The yield is therefore quantitive.

100 mg (0.267 mmole) of the hydrochloride obtained previously is dissolved under an inert atmosphere in 1.5 ml of dichloromethane.

The reaction medium is cooled down to about 0-5° C., then 90 µl of TEA is added.

Agitation is carried out for 15 minutes at 5° C., then 20 µl of diphosgene is added.

Agitation is continued for 30 minutes at 5° C.

Then, the reaction medium is treated with a 10% aqueous solution of tartaric acid, followed by extracting with dichloromethane, washing the organic phase with a saturated aqueous solution of sodium chloride, drying over magnesium sulphate, and evaporating the solvent under reduced pressure.

In this way 130 mg of an oil is obtained which is purified by chromatography on silica eluting with a dichloromethane/ethyl acetate mixture 9/1.

Then 72 mg of trans phenylmethyl 4-(benzoylamino)-1-(chlorocarbonyl)-4-methyl-2-pyrrolidine carboxylate of molecular formula $C_{21}H_{21}N_2O_4Cl$ (M=400.865 g) is recovered, which corresponds to a yield of 67%.

373 mg (0.930 mmole) of the compound obtained previously is dissolved in 9 ml of tetrahydrofuran.

The solution is then cooled down to −70° C. and 1 ml of a 1 M solution of lithium bis(trimethylsilyl)amide in the tetrahydrofuran is added over 5 minutes.

The reaction medium is left to heat up to 0° C. over 45 minutes, then 69 µl of acetic acid is added, followed by diluting with dichloromethane, washing with a 10% aqueous solution of tartaric acid, then with a solution of phosphate buffer at pH=7.0 and with a saturated aqueous solution of sodium chloride.

The organic phase is dried over magnesium sulphate, followed by concentrating to dryness under reduced pressure, in order to obtain 330 mg of a crude product which is purified by chromatography on silica, eluting with a dichloromethane/ethyl acetate mixture 98/2 containing 0.1% by volume of TEA.

In this way 123 mg of expected compound of molecular formula C21H20N2O4 (M=364.404 g) is recovered, which corresponds to a yield of 36%.

1H NMR

In CDCl3, at 300 MHz, chemical shifts of the peaks in ppm and multiplicity:

1.76 (s): C$\underline{H}$3; 2.11 (dd) and 2.73 (ddd): N—CH—C$\underline{H}_2$; 2.93 (dt) and 3.00 (d): N—C$\underline{H}_2$; 3.96 (ddd): N—C$\underline{H}$—CH$_2$; 5.21: CO$_2$C$\underline{H}_2$C$_6$H$_5$; 7.36 (m): CH$_2$C$_6\underline{H}_5$; 7.43 (t) and 7.57 (tt) and 7.72 (d): COC$_6\underline{H}_5$.

IR (CHCl$_3$): 1776, 1745, 1682; 1601, 1580, 1498 cm$^{-1}$.

MS (positive electrospray) m/z: [2M+Na]$^+$=751; [2M+H]$^+$=729; [M+Na]$^+$=387; [M+H]$^+$=365

Example 10

1-propenyltriphenylphosphonium salt of trans phenylmethyl 2-oxo-3-(sulphooxy)-1,3-diazabicyclo [2.2.1]heptane-6-carboxylate 15 g (46.71 mmoles) of cis 1-(1,1-dimethylethyl) and 2-(phenylmethyl) 4-hydroxy-1,2-pyrrolidinedicarboxylate (commercial product) of molecular formula $C_{17}H_{23}NO_5$ (M=321.377 g) is dissolved under an inert atmosphere in 225 ml of anhydrous dichloromethane.

5.42 ml of 2,6-lutidine is added to the solution. The reaction medium is cooled down to −70° C., then, 8.25 ml of trifluoromethanesulphonic anhydride is introduced over 5 minutes.

Agitation is carried out for 10 minutes at −70° C. then 4.43 g of O-allyl-hydroxyl-amine is introduced at −70° C.

Then the reaction mixture is left at ambient temperature for 27 hours, followed by diluting with dichloromethane, then washing with a 10% aqueous solution of tartaric acid, with a saturated aqueous solution of NaHCO$_3$, and with water.

The organic phase is dried over sodium sulphate, and the solvent is evaporated off under reduced pressure.

In this way 23 g of a crude oil is obtained which is purified by chromatography on silica, the eluent being successively a dichloromethane/ethyl acetate mixture 95/5, 90/10, then 80/20.

7.18 g of trans 1-(1,1-dimethylethyl) and 2-(phenylmethyl) 4-[(2-propenyloxy)amino]-1,2-pyrrolidine dicarboxylate of molecular formula C$_{20}$H$_{28}$N$_2$O$_5$ (M=376.456 g) is recovered, which corresponds to a yield of 40%.

3.25 g (8.63 mmoles) of the compound obtained previously is dissolved in 3.5 ml of ethyl acetate.

The reaction medium is cooled down to about 0-5° C., then 19 ml of a solution of 4.6 mol/l of hydrogen chloride in ethyl acetate is added.

The reaction medium is left to react whilst agitating at about 0-5° C. for 40 minutes.

The solvent is evaporated off under reduced pressure, followed by taking up several times in diethyl ether, whilst drawing off the liquid supernatant.

In this way 2.54 g of a hydrochloride is obtained in the form of a white precipitate, which is dissolved in 55 ml of dichloromethane under agitation. 7.3 ml of 2N soda is added. After decanting, the organic phase is dried over sodium sulphate.

The dichloromethane is evaporated off under reduced pressure.

In this way 2.12 g of trans phenylmethyl 4-[(2-propenyloxy)amino]-2-pyrrolidinecarboxylate of molecular formula C$_{15}$H$_{20}$N$_2$O$_3$ (M=276.337 g) is obtained in the form of an oil i.e. a yield of 89%.

4.14 g (15 mmoles) of the compound obtained previously is dissolved under an inert atmosphere in 1.5 l of acetonitrile.

The reaction medium is cooled down to about 0-5° C. and 1.14 ml of diphosgene is added. Agitation is carried out for 15 minutes whilst maintaining at 0-5° C., then 4.6 ml of TEA, and 1.83 g of DMAP in 80 ml of acetonitrile are added successively.

The temperature is allowed to rise to ambient temperature and the reaction medium is left to react for 26 hours, then half the solvent is evaporated off under reduced pressure, followed by treating with a 10% aqueous solution of tartaric acid, then extracting with dichloromethane. The organic phase is washed with a saturated aqueous solution of sodium chloride, dried over magnesium sulphate and the solvent is evaporated off under reduced pressure.

In this way 43 g of crude product is obtained which is purified by chromatography on silica eluting with a dichloromethane/ethyl acetate mixture 90/10 containing 0.1% of TEA.

312 mg of trans phenylmethyl 2-oxo-3-(2-propenyloxy)-1,3-diazabicyclo[2.2.1]heptane-6-carboxylate of molecular formula C$_{16}$H$_{18}$N$_2$O$_4$ (M=302.33 g) is recovered which corresponds to a yield of 7%.

70.2 mg (0.232 mmole) of the compound obtained previously is dissolved under an inert atmosphere in 2.3 ml of dichloromethane. Then 26.5 µl of acetic acid and 134 mg of Pd(P(Ph)$_3$)$_4$ are introduced.

The reaction medium is left to react for 40 minutes at ambient temperature, then the temperature is lowered to −20° C. and 2.96 ml of a solution of SO3-pyridine complex at 0.314 mol/l is added. The reaction medium is left to react for 2 hours and 30 minutes then dichloromethane is added followed by evaporating under reduced pressure, taking up in 40 ml of dichloromethane and washing with 5 ml of water. The organic phase is separated and dried over sodium sulphate, then the solvent is evaporated off under reduced pressure.

In this way 280 mg of crude product is obtained which is purified by chromatography on silica, eluting successively with a dichloromethane/acetone mixture 80/20 containing 0.1% TEA, then a dichloromethane/acetone mixture 50/50 containing 0.1% TEA.

34.0 mg of expected compound, of molecular formula C$_{34}$H$_{33}$N$_2$O$_7$SP (M=644.689 g) is recovered in the form of a yellow oil, i.e. a yield of 23%.

1H NMR

In CDCl3, at 400 MHz, chemical shifts of the peaks in ppm and multiplicity: 2.00(m) and 2.48(m): C$\underline{H}_2$—CH—C=O; 2.72(d) and 3.12(s): CH—C$\underline{H}_2$—N; 3.75(m): CH$_2$—C$\underline{H}$—C=O$_2$; 4.71(s) C$\underline{H}$—CH$_2$—N; 5.18 [AB] C$\underline{H}_2$—C$_6$H$_5$; 7.35(m): CH$_2$—C$_6$$\underline{H}_5$ and 2.29(m): C$\underline{H}_3$—CH=CH; 6.62 and 7.21 CH$_3$—C$\underline{H}$=C$\underline{H}$; 7,60-7.85 P(C$_6$H$_5$)$_3$ MS (negative and positive electrospray) m/z:

[Manion]$^-$=341

[Mcation]$^+$=303

Example 11

1-propenyltriphenylphosphonium salt of trans methyl 2-oxo-3-(sulphooxy)-1,3-diazabicyclo[2.2.1]heptane-6-carboxylate The operation is carried out as in Example 10, but starting from 207 mg of cis 1-(1,1-dimethylethyl) and 2-methyl 4-hydroxy-1,2-pyrrolidinedicarboxylate.

In this way 12 mg of desired product of formula C$_7$H$_{10}$N$_2$O$_7$S (M=266.231 g) is obtained.

MS (negative and positive electrospray) m/z:

[Manion]$^-$=265

[Mcation]$^+$=303

Example 12a trans diphenylmethyl 7-oxo-6-oxa-1-azabicyclo[3.2.1]octane-3-carboxylate 8 ml of dichloromethane and 347 mg (1 mmole) of the hydrochloride of cis diphenylmethyl 5-hydroxy-3-piperidinecarboxylate (described in Acta Chem. Scand. Ser. B 35(4) 289-294) are mixed under an inert atmosphere.

The reaction medium is cooled down to 0° C., then 346 µl of TEA and 72 µl of diphosgene are added.

The reaction medium is left to react for 15 minutes whilst maintaining the temperature at 0° C., then the solvent is evaporated off under reduced pressure, followed by taking up in 25 ml of dry toluene and filtering to eliminate the hydrochloride from the TEA.

553 µl of TEA is added to the filtrate and heating is carried out under reflux for 4 hours, followed by diluting with ethyl acetate, washing with an aqueous solution containing 10% tartaric acid, then with a saturated aqueous solution of sodium chloride and drying the organic phase over magnesium sulphate.

The reaction medium is then evaporated under reduced pressure and 339 mg of crude product is recovered which is purified by chromatography on silica, eluting with a toluene/ethyl acetate mixture 70/30.

In this way 146 mg of expected compound (M=337.378 g) is recovered, which corresponds to a yield of 43%.

1H NMR

In CDCl3, at 250 MHz, chemical shifts of the peaks in ppm and multiplicity:

2.15 (ddd) and 2.73 (dq): N—C$\underline{H}_2$—CHO—C$\underline{H}_2$; 2.92 (tt): O$_2$C—C$\underline{H}$—; 3.00 (d) and 3.45 (d): N—C$\underline{H}_2$—CHO; 3.48 (dd) and 4.07 (dd): N—C$\underline{H}_2$—CH—CO$_2$; 4.79 (dt): N—CH$_2$—C$\underline{H}$O; 6.90 (s): CO$_2$—C$\underline{H}$—(C$_6$H$_5$)$_2$; 7.33 (m): (C$_6$$\underline{H}$$_5$)$_2$.

IR (CHCl3): 1792, 1734; 1600, 1585, 1497 cm$^{-1}$.

MS (EI) m/z: [M]$^+$=337, 292, 183, 167.

Example 12b trans-7-oxo-6-oxa-1-azabicyclo[3.2.1]octane-3-carboxylic acid 320 mg of the compound obtained in Example 12a, 17 ml of acetone and 70 mg of Pd/C catalyst at 20% by weight are mixed together.

Agitation is carried out under a hydrogen atmosphere at normal pressure.

After 2 hours 30 minutes, another 70 mg of catalyst is added and the reaction medium is left to react for another 1 hour 30 minutes, followed by filtering.

The solvent is evaporated off under reduced pressure and in this way 350 mg of the crude product is obtained which is crystallized from pentane.

Filtration is carried out and in this way 158 mg of the sought product of molecular formula C$_7$H$_9$NO$_4$ (M=171.154 g) is recovered in the form of a grey solid. The corresponding yield is 89%.

1H NMR

In DMSO, at 300 MHz, chemical shifts of the peaks in ppm and multiplicity:

2.10 (ddd) and 2.43 (dm): N—C$\underline{H}_2$—CHO—C$\underline{H}_2$; 2.83 (tt): O$_2$C—C$\underline{H}$—; 3.13 (d) and 3.27 (dm): N—C$\underline{H}_2$—CHO; 3.40 (dd) and 3.72 (d): N—C$\underline{H}_2$—CH-CO$_2$H; 4.81 (m): N—CH2—C$\underline{H}$O; 12.54 (broad s): CO$_2$$\underline{H}$.

IR (nujol): 1782, 1692 cm$^{-1}$.

MS (EI) m/z: [M]$^+$=177, 155, 127, 82, 70.

Example 12c trans (4-nitrophenyl)methyl 7-oxo-6-oxa-1-azabicyclo[3.2.1]octane-3-carboxylate 30 mg (0.175 mmole) of the acid obtained in Example 12b and 0.5 ml of dichloromethane are mixed together under an inert atmosphere. Then 26.8 mg of 4-nitrobenzyl alcohol, 2.2 mg of DMAP and 37 mg of EDCI are added.

The reaction medium is left to react whilst agitating for 2 hours at ambient temperature.

The organic phase is then diluted with dichloromethane, washed with a 10% aqueous solution of tartaric acid and with a solution of phosphate buffer at pH 7.

After drying the organic phase over sodium sulphate, and evaporating the solvent under reduced pressure, 57 mg of crude product is obtained which is purified by chromatography on silica eluting with a toluene/ethyl acetate mixture 85/15.

The product is then crystallized from a mixture of ethyl ether and pentane in order to produce 34 mg of white crystals of the sought compound (M=306.277 g). The corresponding yield is 63.5%.

1H NMR

In CDCl3, at 300 MHz, chemical shifts of the peaks in ppm and multiplicity:

2.14 (ddd) and 2.84 (dm): N—C$\underline{H}_2$—CHO—C$\underline{H}$2; 2.90 (tt): O$_2$C—C$\underline{H}$—; 3.10 and 3.49 (dm); N—C$\underline{H}_2$—CHO; 3.43 (dd) and 4.14 (bd): N—C$\underline{H}_2$—CH—CO$_2$; 5.27 [AB]: CO$_2$—C$\underline{H}_2$—C$_6$H$_5$; 7.56 and 8.24 [AA'BB']: C—C$_6$$\underline{H}_5$—NO$_2$.

IR (CHCl$_3$): 1799, 1789, 1741; 1609, 1526, 1495 cm$^{-1}$.

MS (EI) m/z: [M]$^+$: 306, 170, 136, 126, 106, 82.

Example 13

6-(phenylmethyl)-1,6-diazabicyclo[3.2.1]octan-7-one

Stage A:

30.7 ml of TEA is added at about 0-5° C. to a solution of 20.71 g of 3-amino-pyridine in 200 ml of methylene chloride. 25.5 ml of benzoyl chloride is then added dropwise over 15 minutes and the reaction medium is left to return to ambient temperature. Agitation is carried out for 1 hour, followed by washing with water, then with a saturated solution of sodium bicarbonate, the organic phase is dried over sodium sulphate and the solvent is evaporated off under reduced pressure. 42.29 g of expected crystallized product (M=198.226 g) is obtained.

Stage B:

4.3 ml of concentrated hydrochloric acid and 500 mg of rhodium on alumina at 5% by weight are added to a solution of 10 g of the product obtained in Stage A in 200 ml of methanol. The reaction medium is place under a hydrogen atmosphere at a pressure of 60-110 bars for 15 hours.

The reaction mixture is filtered, rinsed with methanol then the filtrate is concentrated under reduced pressure. The hydrochloride of the expected product is obtained in a mixture with 10% of the hydrochloride of the starting product.

The product is taken up in 250 ml of methylene chloride and 1.1 equivalent of 1N soda is added. After agitation for 15 minutes, the methylene chloride is decanted, the organic phase is washed with water, followed by drying and evaporating under reduced pressure. The residue is chromatographed on silica eluting with a methylene chloride—methanol—triethylamine mixture 92/8/3.

7.4 g of expected crystallized product is obtained, i.e. a yield of 72%.

Stage C: N-(phenylmethyl)-3-piperidinamine 20 g of the product obtained as described in Stage B is dissolved in 600 ml of 1,2-dimethoxyethane. 14.86 g of lithium aluminium hydride is added to the solution over 30 minutes, followed by heating under agitation and under an inert gas at 75-80° C. for 16 hours then cooling down to 0° C. and 11 ml of water is added over 45 minutes, without exceeding 12° C. Agitation is carried out for 10 minutes, followed by filtering and washing the precipitate with methylene chloride. The filtrate is concentrated under reduced pressure. 17.8 g of expected product is obtained in the form of an oil which is distilled under reduced pressure (boiling temperature: 114-121° C./0.8 mbar). 16 g of expected product is recovered, i.e. a yield of 86%.

Stage D: 6-(phenylmethyl)-1,6-diazabicyclo[3.2.1]octan-7-one 1.06 g of product obtained in Stage C is dissolved in 28 cm$^3$ of toluene, then the reaction medium is cooled down to 0° C. and 337 µl of diphosgene is added under an inert gas. The temperature is allowed to rise and is maintained at 20° C. for 2 hours. Concentration is carried out under reduced pressure then the residue is chromatographed on silica eluting successively with methylene chloride-acetone 95/5 then 80/20 and finally methylene chloride-methanol, triethylamine 92/8/3 and 362 mg of expected product $C_{13}H_{16}N_2O$ (M=216.85 g) is obtained i.e. a yield of 30%.

VPC/Mass spectrum (EI) m/z: [M]$^+$=216, 125, 91.
IR (CHCl$_3$): 1718; 1498 cm$^{-1}$.

Example 14

6-benzoyl-1,6-diazabicyclo[3.2.1]octan-7-one

Stage A: 3-(benzylamino)-1-piperidinecarboxylic 5 g of product obtained in Stage B of Example 13, is dissolved in 1.25 l of anhydrous toluene under a nitrogen atmosphere then 3.4 ml of TEA is added and 1.47 ml of diphosgene is introduced at 0-5° C. over 3 minutes. After 20 minutes at 0-5° C., the reaction medium is left to heat up to 20° C., is maintained under agitation for 75 minutes, then the solvent is evaporated off under reduced pressure. The residue is chromatographed on silica eluting with a methylene chloride-acetone mixture 8/2. 3.44 g of expected product is obtained (yield of 52.6%).

Stage B 6-benzoyl-1,6-diazabicyclo[3.2.1]octan-7-one 48 mg of sodium hydride at 50% in dispersion in oil and 20 ml of THF are introduced under a nitrogen atmosphere. The reaction medium is cooled down to about 0-5° C., then 266mg of the product obtained in Stage A is added in one go.

The temperature is allowed to rise to ambient temperature, then 60 µl of acetic acid and 10 ml of phosphate buffer at pH 7 are added.

Then a little ethyl acetate is added followed by decanting and reextracting with ethyl acetate. The organic phase is dried over magnesium sulphate, then the solvents are evaporated off under reduced pressure.

The crude product is chromatographed on silica eluting with dichloromethane containing 2% acetone.

In this way 143 mg of the sought product $C_{13}H_{12}N_2O_2$ (M: 228.25 g) is obtained. The corresponding yield is 62%.

1H NMR

In CDCl3, at 250 MHz, chemical shifts of the peaks in ppm and multiplicity:

1.20-2.15 (m) and 2.42 (m): NCH—CH$_2$—CH$_2$—; 2.80 (d) –2.93 (d); 3.11 (m); 3.28 to 3.58 (m): CH$_2$—N; 4.54 (m): CH—N; 7.43 (m); 7.55 (m); 7.69 (m): C$_6$H$_5$ IR (CHCl$_3$): 1758, 1672; 1605, 1586, 1492;
MS (EI) m/z: [M]$^+$=230, 125, 105, 77

Example 15

7-oxo-1,6-diazabicyclo[3.2.1]octan-6-acetic acid

Stage A:

5-[(1,1-dimethylethyl)dimethylsilyl]-1,6-diazabicyclo[3-2-1]octan-7-one]

843 mg of lithium is placed under a nitrogen atmosphere and condensed at –70° C. with 320 ml of ammonia. 7.56 g (34.8 mmoles) of the product obtained in Example 13 in 160 ml of tetrahydrofuran is added at –70° C. over 10 minutes. Agitation is carried out for 5 minutes then the ammonia is distilled under a stream of nitrogen whilst heating slowly to 20° C. 7.9 g of (1,1-dimethylethyl) dimethylsilyl chloride in 10 cm$^3$ of tetrahydrofuran is added slowly to the suspension obtained, at 20° C., then maintained under agitation for 10 minutes. Then 160 cm$^3$ of ethyl acetate then 60 cm$^3$ of a 10% aqueous solution of tartaric acid are added, followed by decanting, reextracting with ethyl acetate washing the organic phase with water, drying it over sodium sulphate and evaporating the solvent under reduced pressure. The oil obtained is chromatographed on silica with 10% water, eluting with methylene chloride then with a methylene chloride—acetone mixture 8/2 and 3.04 g of expected product is obtained (yield: 36.2%).

1H NMR

In CDCl3, at 250 MHz, chemical shifts of the peaks in ppm and multiplicity: 0.21(S) and 0.40(S): SiCH$_3$; 0.97(S): SitBu; 1.5 to 1.8(m) and 2.07(m): N—CH—CH$_2$—CH$_2$; 2.85 (d) and 3.32 (m); —CH—CH$_2$—N: 2.93 (dt) and 3.32 (m): —CH$_2$—CH$_2$—N; 3.65 (m): CH—N.

IR (CHCl$_3$): 1710; 842 cm$^{-1}$.
MS (EI) m/z: [M]$^+$: 240, 225, 183, 100, 83, 57.

Stage B:

phenylmethyl 7-oxo-1,6-diazabicyclo[3-2-1]octan-6-acetate 1.44 g (5.99 mmoles) of the product obtained in Stage A is dissolved under a nitrogen atmosphere in 14.4 ml of tetrahydrofuran then 941 µl of phenylmethyl bromoacetate is added and then, 6 ml of a 1 M solution of tetra-n-butyl ammonium fluoride in tetrahydrofuran is added dropwise. Agitation is carried out for 10 minutes at 20° C. then the reaction medium is diluted with 15 ml of ethyl acetate and 5 ml of an aqueous solution of phosphate buffer at pH=7 is added, followed by decanting, reextracting with ethyl acetate, washing the organic phase with water, drying it over sodium sulphate and the solvent is evaporated off under reduced pressure. The oily residue is chromatographed on silica with 10% water eluting with a methylene chloride-acetone mixture 8/2. 140 mg of the expected product is obtained. The corresponding yield is 9%.

IR (CHCl$_3$): 1746, 1720 cm$^{-1}$.
MS (EI) m/z: [M]$^+$=274, 183, 155, 139, 91, 83.

Stage C: 7-oxo-1,6-diazabicyclo[3.2.1]octane-6-acetic acid 137 mg of the product obtained in Stage B is dissolved in 1.5 ml of ethyl acetate, then 14 mg of 10% palladium on carbon is added to the solution and the reaction medium is placed under a hydrogen atmosphere. After 15 minutes another 15 mg of palladium on carbon is added and the reaction medium is maintained under agitation for 15 minutes. The catalyst is filtered, followed by rinsing with ethyl acetate, then with acetone and with methanol and the solvent is evaporated off under reduced pressure. A total of 68 mg of crude product is obtained which is crystallized from ether. 58 mg of the expected product of molecular formula $C_{15}H_{18}N_2O_3$ (M=274.321 g) is obtained. The corresponding yield is 63%.

1H NMR

In CDCl3, at 400 MHz, chemical shifts of the peaks in ppm and multiplicity:

1.48 (m), 1.63 (m), 1.73 (m) and 1.86 (m): N—CH—CH$_2$—CH$_2$; 2.85 to 3.00 (m), 3.14 (dm) and 3.64 (m): CH$_2$—N—CH$_2$ and CH—N; 3.78 and 4.14 [AB]: CON—CH$_2$—CO.

MS (EI) m/z: [M]$^+$=184, 139, 125, 111, 97, 83.

Example 16

7-oxo-N-phenyl-1,6-diazabicyclo[3.2.1]octane-6-carboxamide 1 ml of tetrahydrofuran and 99 mg (0.41 mmole) of the compound obtained in Stage A of Example 15 are mixed under an inert gas.

50 μl of phenyl isocyanate then 450 μl of a 1M solution of tetrabutylammonium fluoride in THF are added successively.

The reaction medium is left to react for 10 minutes, then diluted with ethyl acetate, followed by washing with water, decanting and drying the organic phase over magnesium sulphate. The solvent is evaporated off under reduced pressure. In this way 140 mg of crude product is obtained which is purified by chromatography on silica eluting with a dichloromethane/ethyl acetate mixture 90/10.

21 mg of the title compound, of molecular formula C$_{13}$H$_{15}$N$_3$O (M=245.283 g) is recovered which corresponds to a yield of 20%.

1H NMR

In CDCl3, at 250 MHz, chemical shifts of the peaks in ppm and multiplicity: 1.78 (m), 2.02 (m) and 2.17 (m): N—CH—CH$_2$—CH$_2$; 2.88 (d), 3.13 (dt) and 3.42 (m): CH$_2$—N—CH$_2$; 4.49 (m): CH—N; 7.11(t); 7.34(t) and 7.54(d): C$_6$H$_5$; 10.05: NH.

IR (CHCl$_3$): 3302, 3266; 1734; 1700; 1602, 1553, 1501 cm$^{-1}$.

MS (EI) m/z: [M]$^+$: 245, 153, 126, 119, 98, 92.

Example 17a

6-[1-(phenylmethyl)-1H-tetrazol-5-yl]-1,6-diazabicyclo[3.2.1]octan-7-one 480 mg (2 mmoles) of the compound obtained in Stage A of Example 15 is placed under an inert gas.

Then a solution of 712 mg of 5-fluoro-1-(phenylmethyl)-1H-tetrazole in 1.5 ml of tetrahydrofuran and then 2 ml of a 1 M solution of tetrabutylammonium fluoride in THF is added. The reaction medium is left to react for 1 minute, followed by diluting with ethyl acetate, washing with water, decanting, drying the organic phase over magnesium sulphate and the solvent is evaporated off under reduced pressure.

1.06 g of an oily product is obtained which is chromatographed on silica in a dichloromethane/ethyl acetate mixture 90/10.

In this way 143 mg of expected compound of molecular formula C$_{14}$H$_{16}$N$_6$O (M=284.324 g) is obtained in the form of an amorphous white product. The corresponding yield is 25%.

1H NMR

In CDCl3, at 250 MHz, chemical shifts of the peaks in ppm and multiplicity: 1.80 (m), 2.04 (m) and 2.67 (m): N—CH—CH$_2$—CH$_2$; 2.83 (d), 2.85 (dm), 3.10 (dd) and 3.44 (dd): CH$_2$—N—CH$_2$; 3.99 (m): CH—N; 5.63 and 5.88 [AB]: C$_6$H$_5$—CH$_2$; 7.18 (m) and 7.32 (m): C$_6$H$_5$.

Example 17b 6-(1H-tetrazol-5-yl)-1,6-diazabicyclo[3.2.1]octan-7-one 120 mg of the product obtained in Example 17a and 2.4 ml of a methanol/ethyl acetate mixture 90/10 are mixed together then 2.4 ml of THF is added until total dissolution is obtained.

Then 24 mg of 10% palladium catalyst on carbon is added then agitation is carried out under a hydrogen atmosphere. After reaction for 3 hours, the catalyst is filtered, followed by rinsing with a tetrahydrofuran/methanol mixture, then the solvent is evaporated off under reduced pressure. Then the product crystallizes from ethyl ether.

In this way 72 mg of the title compound of molecular formula C7H$_{10}$N$_6$O (M=194.198 g) is obtained in the form of a white crystallized product. The corresponding yield is 88%.

1H NMR

In DMSO, at 300 MHz, chemical shifts of the peaks in ppm and multiplicity: 1.63 (m), 1.89 (m) and 2.07 (m): N—CH—CH$_2$—CH$_2$; 3.14 to 3.20 (m) and 3.43 (m): CH$_2$—N—CH$_2$; 4.51 (m): CH—N.

IR (Nujol): 1744; 1594 cm$^{-1}$.

MS (EI) m/z: [M]$^+$=194, 165, 124, 111, 98, 83, 68, 56, 41.

Example 18

6-acetyl-1,6-diazabicyclo[3.2.1]octan-7-one 140 mg (0.582 mmoles) of the compound obtained in Stage A of Example 15 is dissolved in 1.4 ml of THF.

55 μl of acetic anhydride then 0.58 ml of a 1 M solution of tetrabutylammonium fluoride in THF are added successively to the solution obtained, followed by diluting with ethyl acetate, washing with water, decanting, drying the organic phase over magnesium sulphate, then the solvent is evaporated off under reduced pressure.

In this way 116 mg of a crude oil is obtained which is chromatographed on silica with a dichloromethane/acetone mixture 80/20.

In this way 18 mg of expected compound, of molecular formula C$_8$H$_{12}$N$_2$O$_2$ (M=168.196 g) is obtained, which corresponds to a yield of 18%.

1H NMR

In DMSO, at 300 MHz, chemical shifts of the peaks in ppm and multiplicity: 1.65 to 2.20 (m): N—CH—CH$_2$—CH$_2$; 2.54 (s): CH$_3$CO—N; 2.83 (d), 3.33(dm), 3.10 (m) and 3.45 (dd) CH$_2$—N—CH$_2$; 4.55 (m):
O=C—N—CH.

IR (CHCl$_3$): 1758, 1696 cm$^{-1}$.

MS (EI) m/z: [M]$^+$=168, 140, 126, 98, 43.

Example 19a 6-(phenylmethoxy)-1,6-diazabicyclo[3.2.1]octan-7-one 44.02 g (0.22 mole) of 1,1-dimethylethyl 3-oxo-1-piperidinecarboxylate (C$_{10}$H$_{17}$NO$_3$, M=199.251 g) (described in J. Med. Chem. 1986, 29, 224-229) is dissolved in 440 ml of ethanol.

Then 38.79 g of O-benzyl-hydroxylamine hydrochloride is added. 54 ml of pyridine is then introduced dropwise, into the suspension.

The reaction medium is left to react whilst agitating for 4 hours at approximately 25° C., then the solvent is evaporated off under reduced pressure, followed by taking up in a mixture of dichloromethane and ethyl acetate, filtering and rinsing with dichloromethane, then with a mixture of dichloromethane and ethyl acetate. The filtrate is then concentrated to dryness under reduced pressure.

In this way 69.8 g of a light yellow oil is obtained which is purified by chromatography on silica. The eluent used is a cyclohexane/ethyl acetate mixture 80/20.

57.21 g of 1,1-dimethylethyl 3-[(phenylmethoxy) imino]-1-piperidinecarboxylate, of molecular formula $C_{17}H_{24}N_2O_3$ (M=304.39 g) is recovered, in the form of a very pale yellow oil. The corresponding yield is 85%.

24.82 g (0.0815 mmole) of the oxime obtained previously is dissolved in 163 ml of ethanol cooled down to −10° C. under nitrogen. Then 25 ml of a borane-pyridine complex is added then, 204 ml of 2N hydrochloric acid is added dropwise over one hour 15 minutes. The solution is agitated for 1 hour 15 minutes at −5° C., then treated with 100 ml of a saturated solution of sodium hydrogen carbonate, then with 35 g of sodium carbonate, which are add by small portions. The pH is then 7-8.

The reaction medium is extracted with ethyl acetate.

The organic phases are combined, dried over sodium sulphate and the solvent is evaporated off under reduced pressure. In this way 39.0 g of a colourless oily liquid is obtained which is taken up in 400 ml ethyl acetate.

The solution is washed with a 0.05 N aqueous solution of hydrochloric acid, then the phases organic are combined and the solvent is evaporated off under reduced pressure.

35.5 g of a colourless oily liquid is recovered which is purified by chromatography on silica, eluting with a dichloromethane/ethyl acetate mixture 95/5, then with a dichloromethane/ethyl acetate mixture 80/20.

In this way 17.89 of 1,1-dimethylethyl 3-[(phenylmethoxy)amino]-1-piperidinecarboxylate of molecular formula $C_{17}H_{26}N_2O_3$ (M=306.41 g), is recovered in the form of a colourless oil. The corresponding yield is 72%.

6.72 g (21.9 mmoles) of the piperidine obtained previously is dissolved in 22 ml of ethyl acetate cooled down to −10° C. 28 ml of a 4.0 mol/l solution of anhydrous hydrochloric acid in ethyl acetate is added dropwise, over 30 minutes.

After 1 hour at 0° C., 40 ml of ethyl ether is added, the dihydrochloride precipitate is filtered and washed with ethyl ether.

In this way 3.87 g of a white solid is obtained.

By crystallizing the filtrate, 1.80 g of the desired product is also obtained.

The product obtained is taken up in 60 ml of 1 N soda and 120 ml of ethyl acetate. After decanting, the aqueous phase is saturated with sodium chloride, then extracted twice with ethyl acetate. The organic phases are combined and dried over magnesium sulphate then concentrated to dryness under reduced pressure.

In this way 3.67 g of N-(phenylmethoxy)-3-piperidinamine, of molecular formula $C_{12}H_{18}N_2O$ (M=206.29 g) is obtained, which corresponds to a yield of 81%.

518 mg (2.5 mmoles) of the compound obtained previously is dissolved in 5 ml of anhydrous dichloromethane, then 0.5 ml of TEA is added.

The whitish suspension obtained is cooled down to −65° C., then 12.5 ml of a 0.10 mol/l solution of diphosgene in dichloromethane is added over 15 minutes.

After reaction for 45 minutes, the colourless solution is diluted with 15 ml of dichloromethane and treated with 15 ml of water.

The medium is left to settle, then the aqueous phase is extracted with 20 ml of dichloromethane.

The combined organic phases are dried over magnesium sulphate, then concentrated to dryness under reduced pressure. In this way a pale yellow oil is obtained which is purified by chromatography on silica eluting with an ethyl acetate mixture 90/10, then a dichloromethane/ethyl acetate mixture 80/20.

In this way 196 mg of expected compound of molecular formula $C_{13}H_{16}N_2O_2$, (M=232.28 g) is recovered in the form of a colourless oil. The corresponding yield is 34%.

1H NMR In CDCl3, at 300 MHz, chemical shifts of the peaks in ppm and multiplicity: 1.59 (m) and 1.93 to 2.18 (m): N—CH—$\underline{CH_2}$—$\underline{CH_2}$; 2.73 (dt), 2.94 (dt), 3.17(dt) and 3.40 (dd): $\underline{CH_2}$—N—$\underline{CH_2}$; 3.29 (t): N—$\underline{CH}$; 4.89 (d): N—O—C$\underline{H_2}$—$(C_6H_5)$; 7.38: $C_6\underline{H_5}$.

IR (CHCl$_3$): 1747; 1498 cm$^{-1}$.

MS (EI) m/z: [M]$^+$=232, 91.

Example 19b 6-(acetyloxy)-1,6-diazabicyclo[3.2.1]octan-7-one 95 mg (0.41 mmole) of the compound obtained in Example 19a is dissolved in 5 ml of methanol, agitation is carried out with 8 mg of palladium on carbon at 10% by weight, then the suspension is placed under a hydrogen atmosphere under normal pressure for 1 hour at 25° C., then the catalyst is filtered.

After evaporation of the solvent under reduced pressure, 70 mg of white crystals is obtained.

The crystals are taken up in 2 ml of anhydrous dichloromethane. The solution is cooled down to −10° C. under nitrogen. Then 70 μl of pyridine then 40 μl of acetic anhydride are added and agitation is carried out for 20 minutes. Concentration is carried out under reduced pressure and 75 mg of white crystals are obtained which are purified on silica, eluting with a dichloromethane ethyl acetate mixture 80/20.

49 mg of expected compound (M=184.20 g) is recovered in the form of a white solid. The corresponding yield is 65%.

1H NMR

In CDCl3, at 300 MHz, chemical shifts of the peaks in ppm and multiplicity: 1.60 to 2.2: N—CH—$\underline{CH_2}$—$\underline{CH_2}$; 2.24 (s): CH$_3$; 2.95 (d) and 3.54 (dm): N—$\underline{CH_2}$—CH; 3.07 (dt) and 3.54 (bdd): N—$\underline{CH_2}$—CH$_2$; 3.94 (bt): O=C—N—$\underline{CH}$.

IR (CHCl$_3$): 1798; 1764 cm$^{-1}$.

MS (EI) m/z: [M]$^+$=184, 142, 125, 43.

Example 19c 6-(benzoyloxy)-1,6-diazabicyclo[3.2.1]octan-7-one

The operation is carried out in a similar manner to that which has been described in Example 19b starting from 205 mg of the compound prepared in Example 19a and 200 mg of benzoic anhydride.

In this way 64 mg of expected compound of molecular formula $C_{13}H_{14}N_2O_3$ (M=246.27 g) is obtained i.e. a yield 30%.

1H NMR

In CDCl3, at 250 MHz, chemical shifts of the peaks in ppm and multiplicity: 1.64 to 1.95 (m) and 2.10 to 2.35 (m): CH—

CH₂—CH₂; 3.02 (d) and 3.65 (dm): N—CH₂—CH; 3.13 (dt) and 3.55 (bdd): N—CH₂—CH₂; 4.09 (bt): O=C—N—CH; 7.49 (m): 7.65 (tt); 8.12 (m): C₆H5.

IR (CHCl₃): 1774, 1756;1602, 1585, 1495 cm⁻¹.
MS (EI) m/z: [M]⁺=246, 105, 77.

Example 19d 6-(1-oxopropoxy)-1,6-diazabicyclo[3.2.1]octane-7-one

The operation is carried out in a similar manner to that which has been described in Example 19c, starting from 163 mg of the compound prepared in Example 19a and 70 µl of propionyl chloride.

In this way 17 mg of expected compound of molecular formula $C_9H_{14}N_2O_3$ (M=198.23 g) is obtained, i.e. a yield of 12%.

1H NMR

In CDCl3, at 300 MHz, chemical shifts of the peaks in ppm and multiplicity: 1.25 (t): O=C—CH₂—CH₃; 1.65 (m), 1.78 (m) and 2.10 (m): N—CH—CH₂—CH₂; 2.52 (m) O=C—CH₂—CH₃; 2.94 (d) and 3.55 (bd): N—CH₂—CH; 3.07 (dt) and 3.48 (dd): N—CH₂—CH₂; 3.93 (m): N—CH₂—CH.

IR (CHCl₃): 1792; 1763 cm⁻¹.
MS (EI) m/z: [M]⁺=198, 170, 142, 125, 97, 57.

Example 19e

6-[[(4-methylphenyl)sulphonyl]oxy]-1,6-diazabicyclo[3.2.1]octan-7-one

The operation is carried out in a similar manner to that which has been described in Example 19d, starting from 139 mg of the compound prepared in Example 19a and 126 mg of tosyl chloride.

In this way 77 mg of expected compound of molecular formula $C_{13}H_{16}N_2O_4S$ (M=296.35 g) is obtained i.e. a yield of 44%.

1H NMR

In CDCl3, at 250 MHz, chemical shifts of the peaks in ppm and multiplicity:

1.55 and 2.99 (m): N—CH—CH₂—CH₂; 2.45 (s): CH₃; 2.89 (d), 3.00 (dt), 3.29 (dt) and 3.39 (dd): CH₂—N—CH₂; 4.04 (m): N—CH; 7.35 and 7.91 [AA'BB']CH₃—C₆H₄—SO₂.

IR (CHCl₃): 1775; 1599, 1495, 1383; 1193, 1180 cm⁻¹.
MS (EI) m/z: [M]⁺=296, 155, 141, 125, 91.

Example 19f

6-[(methylsulphonyl)oxy]-1,6-diazabicyclo[3.2.1]octan-7-one

The operation is carried out in a similar manner to that which has been described in Example 19e starting from 211 mg of the compound prepared in Stage 19a and 80 µl of mesyl chloride.

In this way 50 mg of expected compound of molecular formula $C_{17}H_{12}N_2O_4S$ (M=220.25 g) is obtained i.e. a yield of 25%.

1H NMR

In CDCl3, at 250 MHz, chemical shifts of the peaks in ppm and multiplicity: 1.56 and 2.38 (m): N—CH—CH₂—CH₂; 3.00 (d), 3.12 (dt) and 3.49 (m): N—(CH₂)₂; 3.26 (s): CH₃; 4.12 (m): N—CH.

IR (CHCl₃): 1775; 1381, 1187 cm⁻¹.
MS (EI) m/z: [M]⁺=220, 141, 125, 97, 79.

Example 19g

6-[(4-nitrophenyl)sulphonyl]oxy]-1,6-diazabicyclo[3.2.1]octan-7-one

The operation is carried out in a similar manner to that which has been described in Example 19f starting from 270 mg of the compound prepared in Example 19a and 283 mg of 4-nitrobenzenesulphonyl chloride.

In this way 205.5 mg of expected compound of molecular formula $C_{12}H_{13}N_3O_6S$ (M=327.32 g) is obtained i.e. a yield of 54%.

1H NMR

In CDCl3, at 250 MHz, chemical shifts of the peaks in ppm and multiplicity: 1.64 (dt), 1.84 (m), 1.99 (m), 2.31 (dm): NCH—CH₂—CH₂; 2.94 (d), 3.30 (dt), 3.04 (dt), 3.40 (bdd): N(CH₂)₂; 4.14: O=C—N—CH; 8.25 and 8.41 [AA'BB']: NO₂—C₆H₄SO₂.

IR (CHCl₃): 1776; 1610, 1590, 1538; 1393, 1191 cm⁻¹.
MS (EI) m/z: [M]⁺=327, 186, 141, 125, 111.

Example 20

6-[[(4-methylphenyl)sulphonyl]amino]-1,6-diazabicyclo[3.2.1]octan-7-one 5 g (25.1 mmole) of 1,1-dimethylethyl 3-oxo-1-piperidinecarboxylate (described in J. Med. Chem. 1986, 29, 224-229) ($C_{10}H_{17}NO_3$, M=199.251 g) is dissolved in 50 ml of dichloromethane.

4.67 of tosylhydrazine is then added to the solution which is left to react for 2 hours under agitation, then the solvent is evaporated off under reduced pressure.

In this way, 9.56 g of 1,1-dimethylethyl 3-[2-[(4-methylphenyl)sulphonyl]hydrazono]-1-piperidinecarboxylate, of molecular formula C17H25N3O4S (M=367.47 g) is obtained with a quantitative yield.

4.5 g of the compound obtained previously (12.2 mmoles), 90 ml of a methanol/tetrahydrofuran mixture 50/50, and a few grains of bromocresol green are mixed together under an inert gas.

Then 1.62 g of NaBH₃CN is added, followed by cooling down to about 0-5° C., and a 0.7 mol/l solution of gaseous hydrogen chloride in methanol is introduced, in such a way so as to maintain the pH of the medium between 3.8 and 5.4.

The reaction medium is left to react whilst agitating for 2 hours and 30 minutes.

2/3 of the solvents are evaporated under reduced pressure, then 200 ml of dichloromethane is added followed by washing with a saturated aqueous solution of sodium bicarbonate.

The organic phase is dried over sodium sulphate and the solvent is evaporated off under reduced pressure.

In this way 4.48 g of 1,1-dimethylethyl 3-[2-[(4-methylphenyl)sulphonyl]hydrazino]-1-piperidinecarboxylate of molecular formula $C_{17}H_{27}N_3O_4S$ (M=369.486 g) is obtained.

The corresponding yield is 99%.

4.48 g of the compound obtained previously and 9 ml of ethyl acetate are mixed under an inert gas at 0° C.,.

30 ml of a 4 mol/l solution of gaseous hydrogen chloride in ethyl acetate is added, agitation is carried out for 15 minutes followed by filtering and washing the hydrochloride with ethyl acetate. After drying under reduced pressure, 3.48 g of the dihydrochloride of 2-(3-piperidinyl)hydrazide of 4-methyl-benzenesulphonic acid, of molecular formula C$_{12}$H$_{19}$N$_3$O$_2$S, 2HCl (M=342.289 g) is obtained. The corresponding yield is 84%.

Then 3.48 g of the compound obtained previously is dissolved in 5 ml of demineralized water. 10.2 ml of a 2N aqueous solution of soda is added under vigorous agitation.

A precipitate forms after 1 to 2 minutes of contact. Agitation is then carried out for 10 minutes, then the precipitate is filtered and washed with water, then with ethyl acetate.

The solid obtained is dried under reduced pressure.

In this way 2.21 g of 2-(3-piperidinyl)hydrazide of 4-methyl-benzenesulphonic acid, of molecular formula C$_{12}$H$_{19}$N$_3$O$_2$S (M=269.328 g) is obtained. The corresponding yield is 81%.

500 mg (1.85 mmole) of the amine obtained previously and 20 ml of tetrahydrofuran are mixed under an inert gas.

112 μl of diphosgene then 517 μl of TEA and 23 mg of DMAP are added, at a temperature comprised between 0 and 5° C., to the suspension obtained.

The reaction medium is left to react whilst agitating and whilst allowing the temperature to rise to 20° C., followed by diluting with ethyl acetate, then washing with a 10% aqueous solution of tartaric acid, then with demineralized water.

The organic phase is dried over magnesium sulphate, then the solvent is evaporated off under reduced pressure.

769 mg of a crude product is obtained which is dissolved in 7 ml of dichloromethane and 517 μl of TEA.

The reaction medium is left to react overnight under agitation, followed by diluting with dichloromethane, washing with water, drying over sodium sulphate and the solvent is evaporated off under reduced pressure.

The foam obtained (395 mg) is purified by chromatography on silica with a dichloromethane/ethyl acetate mixture 80/20.

44 mg of expected compound, of molecular formula C$_{13}$H$_{17}$N$_3$O$_2$S (M=295.362 g) is recovered. The corresponding yield is 8%.

1H NMR

In CDCl3, at 250 MHz, chemical shifts of the peaks in ppm and multiplicity:

1.55 to 1.80 (m) and 2.18 (m): N—CH—CH$_2$—CH$_2$; 2.42 (s): CH$_3$; 2.88 (d) and 2.93 (m); N—CH$_2$—CH; 3.18 to 3.32 (m): N—CH$_2$—CH$_2$; 4.08 (m): N—CH—CH$_2$; 6.98 (bs): NH.

IR (CHCl$_3$): 3264, 1737, 1599, 1490 cm$^{-1}$.

MS (positive electrospray) m/z: [M+Na]$^+$=318, [M+H]$^+$=296

Example 21

6-[(4-methylphenyl)sulphonyl]-1,6-diazabicyclo[3.2.1]octan-7-one 305 mg (1.52 mmole) of 1,1-dimethylethyl 3-amino-1-piperidinecarboxylate (described in J. Med. Chem. 1992, 35, 4334-4343), of molecular formula C$_{10}$H$_{20}$N$_2$O$_2$ (M=200.282 g) is dissolved in 3 ml of anhydrous dichloromethane.

Then, 212 μl of TEA is added, followed by cooling down to 5° C. and 278 mg of tosyl chloride is added. Agitation is carried out whilst allowing the temperature to return to 20° C. and the reaction medium is left to react for 2 hours, followed by diluting with dichloromethane and washing firstly with a 10% aqueous solution of tartaric acid then with a solution of phosphate buffer at pH=7.

After separating, the organic phase is dried over magnesium sulphate, then the solvent is evaporated off under reduced pressure. In this way an oil is obtained which is purified by chromatography on silica eluting with a dichloromethane/ethyl acetate mixture 9/1.

440 mg of 1,1-dimethylethyl 3-[[(4-methylphenyl)sulphonyl]amino]-1-piperidinecarboxylate (described in J. Med. Chem. 1992, 35, 4334-4343) of molecular formula C$_{17}$H$_{26}$N$_2$O$_4$S (M=354.472 g) is recovered. The corresponding yield is 82%.

A mixture of 425 mg of the compound obtained previously and 2.1 ml of a trifluoroacetic acid/dichloromethane mixture 50/50 is cooled down to 0-5°.

The reaction medium is kept under agitation at 5° C. for 30 minutes.

Then the solvent is evaporated off under reduced pressure in order to obtain 403 mg of 4-methyl-N-(3-piperidinyl)-benzenesulphonamide trifluoroacetate of molecular formula C$_{14}$H$_{19}$F$_3$N$_2$O$_4$S (M=368.377 g).

228 mg of the compound obtained previously is suspended in 2 ml of methanol, then treated with an excess of DOWEX 21K 20-50 Mesh resin activated with soda, followed by filtering, rinsing the resin with methanol, then the filtrate is evaporated under reduced pressure.

In this way 123 mg of 4-methyl-N-(3-piperidinyl)-benzenesulphonamide of molecular formula C$_{12}$H$_{18}$N$_2$O$_2$S (M=254.353 g) is recovered.

118 mg of the amine obtained previously is dissolved under an inert gas in 1.2 ml of dichloromethane.

Then 98 μl of TEA and then 28 μl of diphosgene are introduced successively. The reaction medium is left to react whilst agitating for 30 minutes at 0-5° C., followed by diluting with dichloromethane, washing the organic phase with a 10% aqueous solution of tartaric acid, then with water. After drying over sodium sulphate, filtration and evaporation of the solvent under reduced pressure, the crude product is purified by chromatography on silica eluting with a dichloromethane/acetone mixture 95/5.

In this way 112 mg of the chloride of 3-[[(4-methylphenyl)sulphonyl]amino]-1-piperidinecarboxylic acid, of molecular formula C$_{13}$H$_{17}$ClN$_2$O$_3$S (M=316.308 g) is obtained. The corresponding yield is 76%.

10 mg of sodium hydride (in suspension at 55-65% in the oil) and 2 ml of anhydrous tetrahydrofuran are mixed together under an inert atmosphere.

Then 71 mg of the product obtained previously is added.

Agitation is carried out at ambient temperature for 15 minutes, then 12 μl of acetic acid and 2 ml of solution of phosphate buffer at pH=7 are added.

Agitation is carried out for another 5 minutes, then 5 ml ethyl acetate is added, followed by leaving to settle, then reextracting with ethyl acetate. After separating, the organic phase is dried over magnesium sulphate, filtered and the solvent is evaporated off under reduced pressure.

In this way 65 mg of crude product is obtained which is purified by chromatography on silica, eluting with a dichloromethane/acetone mixture 95/5.

In this way 40 mg of expected compound, of molecular formula C$_{13}$H$_{16}$N$_2$O$_3$S (M=280.348 g) is recovered. The corresponding yield is 64%.

1H NMR

In CDCl3, at 250 MHz, chemical shifts of the peaks in ppm and multiplicity (presence of two conformers 90/10):

1.46 (m), 1.76 (m) and 2.08 (dm): NCH—CH$_2$—CH$_2$; 2.44 (s) and 2.45(s): CH$_3$; 2.82 (d) and 2.98 (m) and 3.28 to 3.50 (m): —N—(CH$_2$)$_2$; 4.55 (m) and 4.65(m): CO—N—CH; 7.33 and 7.78, 7.35 and 8.02 [AA'BB']CH$_3$—C$_6$H$_4$—SO$_2$.

IR (CHCl$_3$): 1758, 1598, 1995, 1367, 1169 cm$^{-1}$.
MS (EI) m/z: [M]+: 280, 216, 155, 125, 97, 91.

Example 22

6-oxa-1-azabicyclo[3.2.1]oct-3-en-7-one 5 ml of dichloromethane and 68 mg of 1,2,3,6-tetrahydropyridin-3-ol hydrochloride (M=135.5 g) (described in Chem. Pharm. Bull. 30(10)3617-3623(1982)) are mixed together under an inert gas.

33 µl of diphosgene is added and agitation is carried out for 5 minutes at 0° C. Then 140 µl of TEA and 61 mg of DMAP are added.

The reaction medium is left to react at ambient temperature for 2 hours, followed by diluting with dichloromethane and washing with a 10% aqueous solution of tartaric acid then with water, decanting and drying the organic phase over magnesium sulphate. The solvent is evaporated off under reduced pressure. In this way 5 mg of crude product is obtained which is purified by chromatography on silica, eluting with dichloromethane then a dichloromethane/ethyl acetate mixture 95/5.

In this way 3 mg of expected compound, of molecular formula C$_6$H$_7$NO$_2$ (M=125 g) is recovered. The corresponding yield is 5%.

Example 23 phenylmethyl trans-3-benzoyl-2-oxo-4-oxa-1,3-diazabicyclo[3.2.1]octane-7-carboxylate 5.50 g (13.7 mmoles) of cis 1-(1,1-dimethylethyl) and 2-(phenylmethyl) 4-[(methylsulphonyl)oxy]-1,2-pyrrolidine dicarboxylate (described in J. Org. Chem. 1991, 56, 3009-3016), of molecular formula C$_{18}$H$_{25}$NO$_7$S (M=399.466 g) and 110 ml of dimethylformamide are mixed together under an inert gas then 2.58 g of N-hydroxyphthalimide, then 1.52 g of potassium hydrogen carbonate is added.

The reaction medium is heated under agitation at 100° C. and maintained at this temperature for 4 hours.

The reaction medium is cooled down to 20° C., 220 ml of water and ice are added, then extraction is carried out with isopropyl ether, followed by drying over magnesium sulphate, then evaporating to dryness under reduced pressure.

The residue is chromatographed on silica, eluting with a dichloromethane/ethyl acetate mixture 90/10.

In this way 3.06 g of trans 1-(1,1-dimethylethyl) and 2-(phenylmethyl 4-[(1,3-dihydro-1,3-dioxo-2H-isoindol-2-yl)oxy]-1,2-pyrrolidinedicarboxylate), of molecular formula C$_{25}$H$_{26}$N$_2$O7 (M=466.494 g) is recovered The corresponding yield is 47%.

3.24 g (6.94 mmoles) of the phthalimide obtained previously is dissolved in 33 ml of dichloromethane.

372 µl of hydrazine hydrate is added.

Agitation is again carried out for 2 hours 30 minutes at 20° C.

The precipitate formed is filtered, rinsed with dichloromethane, then the solvent is evaporated off under reduced pressure.

2.91 g of crude product is obtained which is purified by chromatography on silica, eluting with a dichloromethane/ ethyl acetate mixture 90/10, then 80/20 and 50/50.

In this way a total of 942 mg of trans 1-(1,1-dimethylethyl) and 2-(phenylmethyl) 4-(aminooxy)-1,2-pyrrolidinedicarboxylate, of molecular formula C$_{17}$H$_{24}$N$_2$O$_5$ (M=336.39 g) is recovered. The corresponding yield is 40%.

853 mg of the compound obtained previously (2.53 mmoles) and 8.5 ml of anhydrous dichloromethane are mixed together under an inert gas.

The reaction medium is cooled down to about 0-5° C., then 706 µl of TEA and 588 µl of benzoyl chloride are added.

Agitation is carried out for 10 minutes at 0-5° C., then the reaction medium is left to heat up to 20° C. and left again to react for 30 minutes.

The organic phase is washed with a 10% aqueous solution of tartaric acid, then with water, followed by decanting and drying the organic phase over sodium sulphate, the solvent is evaporated off under reduced pressure.

In this way 1.38 g of product is obtained, which is mixed with 25 ml of dichloromethane. The reaction medium is cooled down to about 10-15° C. and 123 µl of hydrazine hydrate is added.

The reaction medium is left to react whilst agitating at 20° C. for two hours and 30 minutes.

The solvent is evaporated off under reduced pressure.

In this way 1.13 g of crude product is obtained which is purified by chromatography on silica, eluting with a dichloromethane/ethyl acetate mixture 80/20.

948 mg of trans 1-(1,1-dimethylethyl) and 2-(phenylmethyl)4-[(benzoylamino)oxy]-1,2-pyrrolidinedicarboxylate, of molecular formula C$_{24}$H$_{28}$N$_2$O$_6$ (M=440.50 g) is recovered.

The overall yield is therefore 85%.

948 mg of the compound obtained previously is dissolved under agitation in 2 ml ethyl acetate.

The reaction medium is cooled down to 0-5° C., then 4.7 ml of an approximately 4.6 M solution of gaseous hydrogen chloride in ethyl acetate is added in one go.

After 1 hour, the solvent is evaporated off under reduced pressure and the product is taken up 3 times in ethyl ether.

The solvent is evaporated off under reduced pressure. In this way 842 mg of the hydrochloride of trans phenylmethyl 4-[(benzoylamino)oxy]-2-pyrrolidine carboxylate, is obtained in the form of a white friable foam of formula C$_{19}$H$_{20}$N$_2$O$_4$,HCl (M=376.84 g).

The yield is quantitative.

47 mg (0.125 mmole) of the hydrochloride obtained previously is dissolved under an inert gas in 0.5 ml of dichloromethane. 25.2 µl of pyridine is added, then the reaction medium is cooled down to 0-5° C. and 9.5 µl of diphosgene is added.

The temperature is allowed to rise to 20° C., followed by diluting with dichloromethane, washing the reaction medium with a 10% aqueous solution of tartaric acid then with water.

The organic phase is decanted and dried over sodium sulphate. Then the solvent is evaporated off under reduced pressure.

In this way 43.8 mg of crude product is obtained which is purified by chromatography on silica eluting with a dichloromethane/ethyl acetate mixture 90/10.

34.9 mg of trans phenylmethyl 4-[(benzoylamino)oxy]-1-(chlorocarbonyl)-2-pyrrolidinecarboxylate, of molecular formula C$_{20}$H$_{19}$ClN$_2$O$_5$ (M=402.83 g) is recovered.

The corresponding yield is 69%.

13 mg (0.032 mmole) of the compound obtained previously is dissolved in 4 ml of toluene.

9 µl of TEA and 7.8 mg of DMAP are added.

The reaction medium is heated to 100° C. overnight.

The solvent is evaporated off under reduced pressure then the residue is purified by chromatography eluting with dichloromethane.

In this way 4.3 mg of the expected compound, of molecular formula $C_{20}H_{18}N_2O_5$ (M=336.37 g) is recovered. The corresponding yield is 40%.

1H NMR

In CDCl3, at 300 MHz, chemical shifts of the peaks in ppm and multiplicity:

1.97 (ddd) and 2.85 (ddd): N—O—CH—C$\underline{H}_2$—CH; 3.80 (dd) and 4.14 (dd): N—O—CH—C$\underline{H}_2$-N; 4.75 (dd): N—C$\underline{H}$—CH$_2$; 4.93 (t): N—O—C$\underline{H}$—CH$_2$; 5.04 and 5.31 [AB]: O—C$\underline{H}_2$-C$_6$H$_5$; 7.77: and 7.25 to 7.50 (m) CH$_2$-C$_6$$\underline{H}_5$ and OC—C$_6$$\underline{H}_5$.

IR (CHCl$_3$): 1735; 1612, 1575, 1496 cm$^{-1}$

Example 24

3-benzoyl-1,3-diazabicyclo[2.2.2]octan-2-one 2.4 g (10 mmoles) of N-(4-piperidinyl)-benzamide hydrochloride (described in J. Med. Chem. EN. 17(1974), 736-739), of molecular formula $C_{12}H_{16}N_2O$ is dissolved under a nitrogen atmosphere in 30 ml of dichloromethane.

The reaction medium is cooled down to 0° C., 2.8 ml of TEA and 0.66 ml of diphosgene are added under agitation.

After a few minutes, dilution is carried out with dichloromethane, followed by washing with a 10% aqueous solution of tartaric acid, then with water, decanting the organic phase, drying over magnesium sulphate and the solvent is evaporated off under reduced pressure. Purification is carried out on silica eluting with a dichloromethane/ethyl acetate mixture 90/10.

1.62 g of the chloride of 4-(benzoylamino)-1-piperidinecarboxylic acid, of molecular formula $C_{13}H_{15}ClN_2O_5$ (M=266.5 g) is obtained. The corresponding yield is 61%.

1.21 g (48 mmoles) of the compound obtained previously is dissolved under a nitrogen atmosphere in 37 ml of tetrahydrofuran.

The solution is cooled down to –78° C., then 5 ml of a 1M solution of lithium bis(trimethylsilyl)amide in tetrahydrofuran is added dropwise.

The reaction medium is maintained at –78° C. for 15 minutes, the temperature is allowed to rise to ambient temperature and the reaction medium is left to react again for one hour.

The solution is cooled down to 0° C., 720 μl of acetic acid is added. A precipitate forms, followed by diluting with ethyl acetate then washing with a 10% aqueous solution of tartaric acid and with a solution of phosphate buffer at pH=7.0.

The organic phase is decanted and dried over magnesium sulphate, followed by filtering, then the solvent is evaporated off under reduced pressure. The crude product is purified by chromatography on silica eluting with a dichloromethane and ethyl acetate mixture 90/10.

In this way 0.214 g of expected compound, of formula $C_{18}H_{14}N_2O_2$ (M=230 g) is obtained crystallized from ethyl ether.

The corresponding yield is 20%.

1H NMR

In the DMSO, at 250 MHz, chemical shifts of the peaks in ppm and multiplicity: 1.71 to 2.02 (m): (C$\underline{H}_2$)$_2$—CHN; 3.14 (t): N—(CH$_2$)$_2$; 4.84 (m): (CH$_2$)$_2$—C$\underline{H}$N; 7.39 to 7.65 (m): C$_6$$\underline{H}_5$.

IR (CHCl$_3$): 1735, 1682; 1618, 1602, 1582; 1488 cm$^{-1}$.

MS (positive electrospray) m/z: [2M+Na]$^+$=483; [M+Na+CH$_3$CN]$^+$=294; [M+Na]$^+$=253

Example 25 trans diphenylmethyl 7-oxo-6-oxa-1-azabicyclo[3.2.1]octane-2-carboxylate 15 ml of dichloromethane and 197 mg (0.633 mmole) of trans diphenylmethyl 5-hydroxy-2-piperidinecarboxylate (described in Rec. Trav. Chim. (1959), 78, 648-658), of molecular formula $C_{19}H_{21}NO_3$ are mixed together under an inert atmosphere.

The reaction medium is cooled down to 0° C., then 42 μl of diphosgene, 177 μl of TEA then 77 mg of DMAP are added successively. The reaction medium is left to react for 4 hours at ambient temperature.

Then the reaction mixture is washed with a 10% aqueous solution of tartaric acid, then with a saturated aqueous solution of sodium chloride .

The organic phases are combined and dried over magnesium sulphate, the solvent is evaporated off under reduced pressure and in this way 195 mg of crude product is obtained which is purified by chromatography on silica, eluting with dichloromethane containing 0.1% water.

An oil is recovered which crystallizes from a pentane/ethyl ether mixture.

In this way 108 mg of expected compound is recovered in the form of white crystals corresponding to the molecular formula $C_{20}H_{19}NO_4$ (M=337.338 g).

The corresponding yield is 51%.

1H NMR

In CDCl3, at 400 MHz, chemical shifts of the peaks in ppm and multiplicity: 1.86 (m) and 2.03 (m): N—CH—CH$_2$—C$\underline{H}_2$—CO; 2.27 (m): N—CH—C$\underline{H}_2$—CH$_2$—CO; 3.07 (d) and 3.29 (m): N—C$\underline{H}_2$—CHO; 4.31 (dd): N—C$\underline{H}$—CH$_2$; 4.73 (m): N—CH$_2$—C$\underline{H}$O; 6.93 (s): CO$_2$—C$\underline{H}$—(C$_6$H$_5$)$_2$; 7.27 to 7.41 (m): CH(C$_6$$\underline{H}_5$)$_2$;

IR (CHCl$_3$): 1788, 1736; 1496 cm$^{-1}$;

MS (SIMS) m/z: [M+Na]$^+$=360, [M+li]$^+$=344; [M]$^+$=337, 167

Example 26a trans (4-nitrophenyl)methyl 7-oxo-6-oxa-1-azabicyclo[3.2.1]octane-2-carboxylate 66 ml of dichloromethane and 1 g (3.56 mmole) of trans (4-nitrophenyl)methyl 5-hydroxy-2-piperidine carboxylate of molecular formula $C_{13}H_{16}N_2O_5$ (M=280.282 g) are mixed together under an inert atmosphere.

The reaction medium is cooled down to 0° C., and 0.24 ml of diphosgene is added. The reaction medium is left to react whilst agitating for 10 minutes at 0° C., then left to heat up to ambient temperature. The solvent is evaporated off under reduced pressure.

The residue is dissolved in 66 ml of toluene and 0.99 ml of TEA is added.

The flask is immersed in an oil bath at 110° C. and maintained there for 15 minutes, followed by leaving to return to ambient temperature, washing with a 10% aqueous solution of tartaric acid, then with an saturated aqueous solution of sodium chloride.

The organic phase is dried over magnesium sulphate then the solvent is evaporated off under reduced pressure.

In this way 0.885 g of crude product is obtained which is purified by chromatography on silica eluting with a toluene/ethyl acetate mixture 85/15.

In this way 0.184 g of expected compound, of molecular formula $C_{14}H_{14}N_2O_6$ (M=306.276 g) is recovered in the form of a yellow oil.

The corresponding yield is 17%.

1H NMR

In CDCl3, at 400 MHz, chemical shifts of the peaks in ppm and multiplicity:

1.92 (m) and 2.07 (m): N—CH—C$\underline{H}_2$—C$\underline{H}_2$—CO; 2.22 (m) and 2.30 (m): N—CH—C$\underline{H}_2$—C$\underline{H}_2$—CO; 3.17 (d) and 3.35 (dm): N—C$\underline{H}_2$—CHO; 4.28 (dd): N—C$\underline{H}$—CH$_2$; 4.79 (m): N—CH$_2$—C$\underline{H}$O; 5.33 [AB]: CO$_2$—C$\underline{H}_2$—C$_6$H$_4$NO$_2$; 7.56 and 8.25 [AA'BB']: CH$_2$—C$_6\underline{H}_4$—NO$_2$ IR (CHCl$_3$): 1791, 1745; 1609, 1526, 1495 cm$^{-1}$;

MS (EI) m/z: [M]$^+$=306, 262, 136, 126, 82, 55

Example 26b trans-7-oxo-6-oxa-1-azabicyclo[3.2.1.]octane-2 carboxylic acid 140 mg (0.457 mmole) of the ester obtained in Example 26a, 7 ml of acetone and 28 mg of Pd/C catalyst at 20% by weight are mixed together.

The reaction medium is left to react whilst agitating for 25 minutes under a hydrogen atmosphere at normal pressure.

The catalyst is filtered and then the solvent is evaporated off under reduced pressure.

In this way 137 mg of expected compound, of molecular formula $C_7H_9NO_4$ (M=171.152 g) is obtained, in the form of an oil, in mixture with one mole of p-toluidine.

The corresponding yield is 97%.

1H NMR

In DMSO, at 400 MHz, chemical shifts of the peaks in ppm and multiplicity:

1.84 (m) and 1.95 to 2.05 (m): N—CH—C$\underline{H}_2$—C$\underline{H}_2$-CO; 3.13 (d) and 3.24 (dd): N—C$\underline{H}_2$—CHO; 4.02 (dd): N—C$\underline{H}$—CH2; 4.81 (dm): N—CH2-C$\underline{H}$O.

Example 26c trans methyl 7-oxo-6-oxa-1-azabicyclo[3.2.1]octane-2-carboxylate 17.25 mg (0.1 mmole) of the acid obtained in Example 26b is dissolved in 3 ml of dichloromethane.

The reaction medium is treated with an excess of diazomethane in solution in dichloromethane, then the solvent is evaporated off under reduced pressure.

In this way 30 mg of crude product is obtained which is purified by chromatography on silica, eluting with a toluene/ethyl acetate mixture 90/10.

6.7 mg of expected compound (M=485.187 g) is recovered.

The corresponding yield is 36%.

Example 27 cis (4-nitrophenyl)methyl 7-oxo-6-oxa-1-azabicyclo [3.2.1]octane-2-carboxylate 0.802 g (2.034 mmoles) of the trifluoroacetate of cis(4-nitrophenyl)methyl 5-hydroxy-2-piperidinecarboxylate (described in Rec. Trav. Chim. (1959), 78, 648-658), of molecular formula $C_{13}H_{16}N_2O_5,CF_3CO_2H$ (M=394.303 g) is introduced under a nitrogen atmosphere, into 40 ml of dichloromethane and the reaction medium is cooled down to 0° C. 0.135 ml of diphosgene is added. Agitation is carried out for 15 minutes at 0° C., the temperature is left to rise to ambient temperature and agitation is continued for 35 minutes.

The solvent is evaporated off under reduced pressure.

This product is dissolved in 40 ml of toluene and 1.1 ml of triethylamine. The reaction mixture is taken to 100° C. for 35 minutes, then left to cool down to ambient temperature, followed by washing with water then with a solution of phosphate buffer at pH=7.

The organic phase is dried over sodium sulphate and the solvent is evaporated off under reduced pressure.

In this way 0.56 g of a crude product is obtained which is purified by chromatography on silica, eluting with a dichloromethane/acetone mixture 95/5.

In this way 110 mg of the expected compound, of molecular formula $C_{14}H_{14}N_2O_6$, (M=306.275 g) is recovered, in the form of an oil.

The corresponding yield is 17%.

1H NMR

In CDCl3, at 300 MHz, chemical shifts of the peaks in ppm and multiplicity: 1.80 to 1.94 and 2.10 to 2.45: N—CH—C$\underline{H}_2$—C$\underline{H}_2$—CO; 3.07 (d), 3.04 (dm) and 3.86 (dd): C$\underline{H}$—N—C$\underline{H}_2$; 4.80 (t): O=C—O—CH; 5.28 and 5.43 [AB]: O=C—O—C$\underline{H}_2$—C$_6$H$_5$; 7.61 and 8.24 [AA'BB']C$_6\underline{H}_4$NO$_2$.

IR (CHCl$_3$): 1801, 1794, 1745, 1704; 1609, 1525, 1498 cm$^{-1}$.

MS (EI) m/z: [M]$^+$=306, 262, 136, 126, 83, 55

Example 28a 1-propenyltriphenylphosphonium salt of trans phenylmethyl 7-oxo-6-(sulphooxy)-1,6-diazabicyclo [3.2.1]octane-2-carboxylate Stage A cis phenylmethyl 5-hydroxy-1-(trifluoroacetyl-2-piperidinecarboxylate 6.19 g (22.77 mmoles) of the hydrochloride of phenylmethyl 5-hydroxy-2-piperidinecarboxylate, of molecular formula $C_{13}H_{18}ClNO_3$ (M=271.746 g) (described in Rec. Trav. Chim. (1959), 78, 648-658) is dissolved under an inert atmosphere in 80 ml of anhydrous dichloromethane.

The reaction medium is cooled down to 5° C. and 9.5 ml of TEA is added then, 6.46 ml of trifluoroacetic anhydride is added dropwise.

The reaction medium is left to react under agitation at 5° C. for one hour, then diluted with dichloromethane, followed by washing successively with a 10% solution of tartaric acid, an aqueous solution of phosphate buffer at pH=7 and an aqueous solution of sodium chloride.

The organic phase is decanted and dried over magnesium sulphate. Then the solvent is evaporated off under reduced pressure.

In this way 10 g of a red oil is obtained which is dissolved in 100 ml of methanol. The reaction medium is cooled down to about 10° C., and 6.8 g (78 mmoles) of sodium hydrogen carbonate in solution in 100 ml of water is added slowly, at 20° C. maximum,.

The reaction medium is left to react under agitation at 20° C. for 30 minutes, then extracted with dichloromethane.

The organic phase is decanted, washed with an saturated aqueous solution of sodium chloride and dried over magnesium sulphate.

The solvent is evaporated off under reduced pressure and in this way 7.6 g of an oil orange oil is collected which is purified by chromatography on silica, eluting with a dichloromethane/ethyl acetate mixture 95/5.

In this way 6 g of expected compound of molecular formula $C_{15}H_{16}F_3NO_4$ (M=331.294 g) is recovered. The corresponding yield is 68%.

Stage B trans phenylmethyl -5-[(2-propenyloxy)amino]-1-(trifluoroacetyl)-2-piperidinecarboxylate, 1.74 g (5.26 mmoles) of the alcohol obtained previously is introduced into 29 ml of acetonitrile. The reaction medium is cooled down to −40° C. and 0.61 ml of 2,6-lutidine ($C_5H_3N(CH_3)_2$) then 0.91 ml of trifluoro methanesulphonic anhydride is added at this temperature.

The reaction medium is left to react under agitation for 30 minutes at −40° C. 0.7 ml (10.52 mmoles) of O-allyl-hydroxylamine is then added, still at −40° C., over one minute.

The reaction medium is left to return to 0° C. then 0.61 ml of 2.6 lutidine is added and the medium is left to react overnight (15 hours), at approximately 5° C., then again for 2 hours at 20° C., followed by diluting with dichloromethane, washing with an aqueous solution of sodium hydrogen carbonate, then with a 10% aqueous solution of tartaric acid and with a saturated aqueous solution of sodium chloride.

The organic phase is decanted, dried over magnesium sulphate and the solvent is evaporated off under reduced pressure.

In this way 2.1 g of a yellow oil is obtained which is purified by chromatography on silica, eluting with a toluene/ethyl acetate mixture 90/10.

1.23 g of expected compound of molecular formula $C_{18}H_{21}F_3N_2O_4$ (M=386.374 g) is recovered.

The corresponding yield is 61%.

Stage C trans phenylmethyl 5-[(2-propenyloxy)amino]-2-piperidinecarboxylate 1.41 g (3.65 mmoles) of the compound obtained previously is dissolved under an inert atmosphere in 25 of anhydrous methanol.

The reaction medium is cooled down to 0-5° C., then 3 additions of 145 mg of NaBH4 are carried out spaced 45 minutes apart.

The reaction medium is then acidified to pH=2 with a 1N aqueous solution of hydrochloric acid cooled down to 5° C. beforehand.

Extraction is carried out with ethyl acetate.

The aqueous phase is cooled down to 5° C., 100 ml ethyl acetate is added, followed by treating with a saturated solution of sodium carbonate until a pH of 8.5 to 9 is obtained and extracting the amine with ethyl acetate. The organic phase is washed with a saturated aqueous solution of sodium chloride, then dried over of magnesium sulphate and concentrated by evaporation of the solvent under reduced pressure.

In this way 0.628 g of expected product of molecular formula $C_{16}H_{22}N_2O_3$ (M=290.364 g) is obtained.

The corresponding yield is 59%.

Stage D trans phenylmethyl 7-oxo-6-(2-propenyloxy)-1,6-diazabicyclo[3.2.1]octane-2-carboxylate 103 mg (0.35 mmoles) of the amine obtained previously is dissolved under an inert atmosphere in 35 ml of anhydrous dichloromethane.

The solution is cooled down to about 0-5° C., and 0.1 ml of TEA, then 21 µl of diphosgene are added dropwise, at this temperature.

The reaction medium is left to react under agitation for 15 minutes at 0-5° C., then the temperature is allowed to rise to 20° C., and 42 mg of DMAP is added. Agitation is continued at 20° C. for approximately 5 hours, followed by diluting with dichloromethane, washing with a 10% aqueous solution of tartaric acid, then with water.

The organic phase is dried over magnesium sulphate and concentrated by evaporation of the solvent under reduced pressure.

In this way 70 mg of crude product is obtained which is purified by chromatography on 5 g of silica, eluting with a dichloromethane/methanol mixture 98/2.

48 mg of expected product of formula $C_{17}H_{20}N_2O_4$ (M=316.36 g) is recovered.

The corresponding yield is 43%.

IR (CHCl$_3$): 1750; 1642; 1600, 1496 cm$^{-1}$.

MS (positive electrospray) m/z: [M+Na+CH3CN]$^+$=380; [M+Na]$^+$=339; [M+H]$^+$=317.

Stage E 1-propenyltriphenylphosphonium salt of trans phenylmethyl 7-oxo-6-(sulphooxy)-1,6-diazabicyclo[3.2.1]octane-2-carboxylate 202 mg (0.638 mmoles) of the compound obtained in Stage D is dissolved under an inert atmosphere in 5.5 ml of anhydrous dichloromethane.

73 µl of acetic acid, 369 mg of Pd(P($C_6H_5$)$_3$)$_4$A are then added at 20° C. to the solution obtained.

After agitation for 30 minutes at ambient temperature, the N-hydroxy-urea formed is treated with 5.5 ml of pyridine and 358 mg of SO$_3$-pyridine complex.

The reaction medium is left to react under agitation for 18 hours at 20° C., followed by concentrating by evaporation of the solvent under reduced pressure, taking up in 50 ml of dichloromethane and washing with water. The organic phase is dried over magnesium sulphate and the dichloromethane is evaporated off under reduced pressure.

In this way 650 mg of crude product is obtained which is purified by chromatography on silica, eluting with a dichloromethane/acetone mixture 60/40 containing 0.1% by volume of TEA.

In this way 280 mg of the phosphonium salt of the expected compound, of molecular formula $C_{35}H_{35}N_2O_7PS$ (M=646.705 g) is recovered.

The corresponding yield is 68%.

1H NMR

In CDCl3, at 300 MHz, chemical shifts of the peaks in ppm and multiplicity:

2.05 (m), 2.22 (dm) and 2.33 (m): N—CH—C$\underline{H}_2$—C$\underline{H}_2$; 2.95 (d) and 3.30 (dt); O=C—N—C$\underline{H}_2$; 4.10 (m) and 4.32 (m): O=C—N—C$\underline{H}$ and O=C—N—C$\underline{H}_2$—C$\underline{H}$; 5.12 (s): COO—C$\underline{H}_2$—$C_6H_5$; 7.36: $C_6\underline{H}_5$ and 2.30 (m): C$\underline{H}_3$—CH=CH; 6.65 and 7.20 CH$_3$—C$\underline{H}$=C$\underline{H}$; 7,65-7.85 P($C_6\underline{H}_5$)$_3$.

IR (CHCl$_3$): 1746; 1638, 1605, 1587, 1495 cm$^{-1}$.

MS (negative and positive electrospray) m/z: [Manion]$^-$=355; [Mcation]$^+$=303.

Example 28b

Sodium salt of trans phenylmethyl 7-oxo-6-(sulphooxy)-1,6-diazabicyclo[3.2.1]octane-2-carboxylate 236 mg (0.364 mmoles) of the phosphonium salt obtained in Stage E of Example 28a is dissolved in 0.8 ml of tetrahydrofuran and 4 drops of water.

The solution obtained is passed through a column of DOWEX 50WX8 resin in Na+ form, eluting with water.

After lyophilization, 127 mg of the expected sodium salt, of molecular formula $C_{14}H_{15}N_2O_7SNa$ (M=378.339 g). is obtained The corresponding yield is 92%.

1H NMR

In DMSO, at 300 MHz, chemical shifts of the peaks in ppm and multiplicity:

1.65 to 2.02: N—CH—C$\underline{H}_2$—C$\underline{H}_2$; 2.91 (d) and 3.04 (dt): O=C—N—C$\underline{H}_2$; 4.00 to 4.05: O=C—N—C$\underline{H}$ and O=C—N—C$\underline{H}_2$—C$\underline{H}$;5.20 [AB]: COO—C$\underline{H}_2$—C$_6$H$_5$; 7.39 (m): C$_6$$\underline{H}_5$.

IR (Nujol): 1744; 1495 cm$^{-1}$.

MS (negative electrospray)_m/z; [M]$^-$=355.

Example 28c trans phenylmethyl 7-oxo-6-[(phenylsulphonyl)oxy]-1,6-diazabicyclo[3.2.1]octane-2-carboxylate 48 mg (0.152 mmoles) of the derivative obtained in Stage D of Example 28a is dissolved in 1.2 ml of dichloromethane.

26 µl of acetic acid then 88 mg of Pd (PPh$_3$)$_4$ are added to it at 20° C., and the reaction medium is left to react for 2 hours at 20° under agitation, followed by diluting by the addition of toluene and the solvents are evaporated off under reduced pressure.

1.5 ml of dichloromethane, 25 µl of pyridine and 24 µl of benzenesulphonyl chloride are added to the crude product obtained.

The reaction medium is left to react at 20° C. under agitation for 1 hour then 12.5 µl of pyridine and 10 µl of benzenesulphonyl chloride are added.

Agitation is carried out for 15 minutes at 20° C., followed by diluting with dichloromethane, washing successively with a 10% aqueous solution of tartaric acid, a solution of phosphate buffer at pH=7 and with a saturated aqueous solution of sodium chloride.

The aqueous phase is dried over magnesium sulphate, and the solvent is evaporated off under reduced pressure. 180 mg of a yellow oil is obtained which is purified by chromatography on silica, eluting with a dichloromethane/ methyl and t-butyl ether mixture 95/5.

In this way 20 mg of expected compound, of molecular formula $C_{20}H_{20}N_2O_6S$ (M=416.456 g) is recovered. The corresponding yield is 31%.

1H NMR

In CDCl3, at 300 MHz, chemical shifts of the peaks in ppm and multiplicity: 1.83 (m) and 2.00 to 2.25 (m): N—CH—C$\underline{H}_2$—C$\underline{H}_2$; 3.02 (d) and 3.16 (dm): O=C—N—C$\underline{H}_2$; 4.04 (m) and 4.11 (dd): O=C—N—C$\underline{H}$ and O=C—N—C$\underline{H}_2$—C$\underline{H}$; 5.21 (s): COO—C$\underline{H}_2$—C$_6$H$_5$; 7.34 (m): C$_6$$\underline{H}_5$; 7.56 (m), 7.70 (m) and 8.03 (m): O$_2$S—C$_6$$\underline{H}_5$.

IR (CHCl$_3$): 1780, 1738; 1600, 1585, 1498; 1386, 1193 cm$^{-1}$.

MS (positive electrospray) m/z: [2M+Na]$^+$=855; [M+Na+CH$_3$CH]$^+$=480; [M+Na]$^+$=439; [MH]$^+$=417.

Example 28d trans pheylmethyl 7-oxo-6-[(2-thienylsulphonyl)oxy]-1,6-diazabicyclo[3.2.1]octane-2-carboxylate Starting from 100 mg (0.316 mmoles) of the compound obtained in Stage D of Example 28a, the operation is carried out in a similar manner to that which has just been described, except that instead of using benzenesulphonyl chloride, 2 thienyl sulphonyl chloride is used.

In this way 8 mg of expected compound, of molecular formula $C_{18}H_{18}N2O_6S_2$ (M=422.481 g) is recovered. The corresponding yield is 30%.

1H NMR

In CDCl3, at 300 MHz, chemical shifts of the peaks in ppm and multiplicity: 1.84 (m) and 2.10 to 2.25: N—CH—C$\underline{H}_2$—C$\underline{H}_2$; 3.02 (d) and 3.24 (dt): O=C—N—C$\underline{H}_2$; 4.06 (m): O=C—N—C$\underline{H}_2$—C$\underline{H}$; 4.14 (dd): O=C—N—C$\underline{H}$; 5.22 (s): COO—C$\underline{H}_2$—C$_6$H$_5$; 7.17 (dd): SO$_3$—C—S—CH=C$\underline{H}$; 7.35 (bs): C$_6$$\underline{H}_5$; 7.80 (dd): SO$_3$—C=C$\underline{H}$; 7.87 (m): SO$_3$—C—S—C$\underline{H}$.

IR (CHCl$_3$): 1780, 1739; 1600, 1503, 1495 cm$^{-1}$.

MS (positive electrospray) m/z: [M+Na+CH$_3$CN]$^+$=867; [2M+Na]$^+$=445; 339, 298, 91.

Example 28e trans phenylmethyl 6-(2-hydroxy-2-oxoethoxy)-7-oxo-1,6-diazabicyclo[3.2.1]octane-2-carboxylate Stage A trans phenylmethyl 7-oxo-6-[2-oxo-2-(2-propenyloxy)ethoxy]-1,6-diazabicyclo[3.2.1]octane-2-carboxylate 48 mg (0.15 mmoles) of the compound obtained in Stage D of Example 28a is dissolved under an inert atmosphere in 1.5 ml of anhydrous dichloromethane.

18 µl of acetic acid then 88 mg of Pd(P(C$_6$H$_5$)3)4 are added at 20° C. and the reaction medium is left under agitation for 1 hour at 20° C., followed by filtering on silica, eluting with a dichloromethane/t-butyl and methyl ether of mixture 7/3.

The solvent is evaporated off under reduced pressure and 70 mg of hydroxy urea is obtained which is taken up in 2 ml of dichloromethane, then 85 µl of TEA and 64 µl of allyl bromoacetate are added.

Agitation is carried out to 20° C. for 3 hours and 30 minutes, followed by washing successively with a 10% aqueous solution of tartaric acid, with an aqueous solution of phosphate buffer at pH=7 and with water.

The organic phase is dried and the solvent is evaporated off under reduced pressure.

In this way 60 mg of crude product is obtained which is chromatographed on silica eluting with a dichloromethane/t-butyl and methyl ether mixture 90/10 containing 0.1% TEA.

22 mg of molecular formula $C_{19}H_{22}N_2O_6$, (M=374.396 g) is recovered. The corresponding yield is 39%.

Stage B trans phenylmethyl 6-(2-hydroxy-2-oxoethoxy)-7-oxo-1,6-diazabicyclo[3.2.1]octane-2-carboxylate 22 mg (0.0587 mmoles) of the compound obtained previously is dissolved under an inert atmosphere in 1 ml of anhydrous dichloromethane.

10 µl of acetic acid and 34 mg of Pd(P(C$_6$H$_5$)$_3$)$_4$ are added at 20° C. and the reaction medium is left to react under agitation at 20° C. for 30 minutes.

The reaction medium is concentrated and taken up in toluene in order to eliminate the acetic acid.

In this way 49 mg of crude product is obtained to which 2 ml of phosphate buffer of pH 7 is added, then it is washed twice with 1 ml of dichloromethane.

The solvent is evaporated off and 46 mg of crude product is obtained which is purified by chromatography on silica, eluting firstly with a dichloromethane/t-butyl and methyl ether mixture 90/10 then with a dichloromethane/ethanol mixture 60/40.

In this way 4.5 mg of expected compound, of molecular formula $C_{37}H_{37}N_2O_6P$ (M=636.691 g) is obtained. The corresponding yield is 12%.

Example 29a trans (4-nitrophenyl) methyl 6-benzoyl-7-oxo-1,6-diazabicyclo[3.2.1]octane-2-carboxylate Stage A cis 1-(1,1-dimethylethyl) and 2-[(4-nitrophenyl)methyl]5-(methylsulphonyl)oxy-1,2-piperidinedicarboxylate 11.25 g (29.5 mmoles) of cis 1-(1,1-dimethylethyl) and 2-[(4-nitrophenyl)methyl]5-hydroxy-1,2-piperidinedicarboxylate (described in Rec. Trav. Chim. (1959), 78, 648-658), of molecular formula $C_{18}H_{24}N_2O_7$ (M=380.398 g) is dissolved under an inert atmosphere in 112 ml of dichloromethane.

The reaction medium is cooled down to 0-5° C., then 5 ml of TEA then 2.44 ml of methanesulphonyl chloride are introduced successively.

The temperature is allowed to return to 20° C. under agitation and the medium is left to react for 1 hour, followed by diluting with dichloromethane, washing twice with water, drying over sodium sulphate, and the solvent is evaporated off under reduced pressure.

In this way 16 g of a crude oil is obtained which is purified by chromatography on silica, eluting with dichloromethane containing 2% ethyl acetate.

9.14 g of expected product of molecular formula $C_{19}H_{26}N_2O_9S$ (M=458.491 g) is recovered. The corresponding yield is 67%.

Stage B trans 1-(1,1-dimethylethyl) and 2-[(4-nitrophenyl)methyl]5-azido-1,2-piperidinedicarboxylate 11.1 g (24.2 mmoles) of the mesylate obtained previously is dissolved under an inert atmosphere in 111 ml of dimethylformamide.

Then 1.73 g of sodium nitride $NaN_3$ is added.

The reaction medium is heated under agitation at 80° C. and is maintained at this temperature for 18 hours, then left to return to 20° C. The dimethylformamide is evaporated off under reduced pressure until a small volume is obtained, then dilution is carried out with ethyl acetate, followed by washing with a 2N solution of soda, then with water, drying over magnesium sulphate, then the solvents are evaporated off under reduced pressure.

The crude oil obtained is purified by chromatography on silica eluting with dichloromethane containing 2% ethyl acetate.

In this way 7.34 g of expected compound, of molecular formula $C_{18}H_{23}N_5O_6$ (M=405:413 g) is obtained in the form of a yellow oil which crystallizes.

The corresponding yield is 75%.

Stage C trans 1-(1,1-dimethyl-ethyl) and 2-[(4-nitrophenyl)methyl]5-amino-1,2-piperidinedicarboxylate 7.34 g (18.1 mmoles) of the azide obtained previously is introduced into 150 ml of tetrahydrofuran and 30 ml of water.

7.2 g of triphenylphosphine is added, then the reaction medium is left to react overnight under agitation at 20° C.

Then the solvent is evaporated off under reduced pressure and two entrainments are carried out with ethyl acetate.

In this way a dry extract is obtained which is purified by chromatography on silica, eluting with dichloromethane containing 5% methanol.

5.62 g of expected compound, of molecular formula $C_{18}H_{25}N_3O_6$ (M=379.416 g) is recovered. The corresponding yield is 82%.

Stage D trans 1-(1,1-dimethylethyl) and 2-[(4-nitrophenyl)methyl]5-(benzoylamino)-1,2-piperidinedicarboxylate 700 mg (1.84 mmole) of the amine obtained previously is dissolved in 8 ml of dichloromethane.

The reaction medium is cooled down to 0° C., then 257 µl of TEA then 214 µl of benzoyl chloride are introduced.

The temperature is allowed to return to 20° C.

After reaction for 40 minutes, dilution is carried out with dichloromethane, followed by washing with a saturated solution of sodium hydrogen carbonate, then with water, drying over sodium sulphate and the solvent is evaporated off under reduced pressure.

In this way 867 mg of expected compound, of molecular formula $C_{25}H_{29}N_3O_7$ (M=483.525 g) is obtained. The corresponding yield is 97%.

Stage E hydrochloride of trans (4-nitrophenyl) methyl 5-(benzoylamino)-2-piperidine carboxylate 861 mg (8 mmole) of the amide obtained previously, 9 ml of methanol, and 2.3 ml of a solution of gaseous hydrogen chloride at 8 mol/l in methanol are mixed together.

The temperature is allowed to return to 20° C. and the reaction medium is left to react for 3 hours. Then 1.15 ml of a solution of hydrogen chloride in methanol is added.

Agitation is carried out for 20 minutes at 20° C., then the solvent is evaporated off under reduced pressure.

Then two entrainments are carried out with dichloromethane, then two entrainments with ethyl ether.

The product crystallizes from ethyl ether.

In this way 715 mg of expected compound of molecular formula $C_{20}H_{22}ClN_3O_5$ (M=419.967 g) is obtained.

The corresponding yield is 96%.

Stage F trans (4-nitrophenyl)methyl 5-(benzoylamino)-1-(chlorocarbonyl)-2-piperidine carboxylate 1.08 g (2.58 mmole) of the hydrochloride obtained as previously and 11 ml of dichloromethane are mixed together.

The suspension obtained is cooled down to about 0-5° C. and 791 µl of TEA is added, then 161 µl of diphosgene is added to the solution obtained.

Agitation is carried out for 5 minutes at 0-5° C., then the reaction medium is left to return to 20° C., and left under agitation for another 30 minutes, followed by diluting with dichloromethane, washing with a 10% aqueous solution of tartaric acid, then with water, drying over sodium sulphate and the solvent is evaporated off under reduced pressure.

The crude product is purified by chromatography on silica eluting with dichloromethane containing 5% acetone.

969 mg of expected compound of molecular formula $C_{21}H_{20}ClN_3O_6$ (M=445.862 g) is recovered.

The corresponding yield is 84%.

Stage G trans (4-nitro-phenyl) methyl 6-benzoyl-7-oxo-1,6-diazabicyclo[3.2.1]octane-2-carboxylate 928 mg (2.08 mmoles) of the compound obtained previously and 27 ml of tetrahydrofuran are mixed together under an inert gas.

The solution obtained is cooled down to −78° C. under agitation, then 2.1 ml of a 1M solution of lithium bis(trimethylsilyl)amide in tetrahydrofuran is introduced.

The reaction medium is left under agitation for 10 minutes at −78° C. then 130 μl of acetic acid is added and agitation is carried out whilst allowing the temperature to rise to 15° C., followed by diluting with ethyl acetate then washing successively with a 10% aqueous solution of tartaric acid, with a solution of phosphate buffer at pH=7 and with water, drying over magnesium sulphate and the solvent is evaporated off under reduced pressure.

In this way 1.6 g of a dry extract is obtained which is purified by chromatography on silica eluting with a dichloromethane/acetone mixture 98/2.

The product is then crystallized from ethyl ether in order to produce 204 mg of expected compound, of molecular formula $C_{21}H_{19}N_3O_6$ (M=409.441 g) The corresponding yield is 24%.

1H NMR

In CDCl3, at 250 MHz, chemical shifts of the peaks in ppm and multiplicity:

1.98 (m), 2.22 (m) and 2.40 (m): N—CH—C$\underline{H}_2$—C$\underline{H}_2$; 3.08 (d) and 3.42 (dt): O=C—N—C$\underline{H}_2$; 4.23 (dd): O=C—N—C$\underline{H}$; 4.53 (m): O=C—N—C$\underline{H}_2$—C$\underline{H}$; 5.34 [AB]: COO—C$\underline{H}_2$—C$_6$H$_5$; 7.69 (m): 8.25 (m): 7.44 (m) and 7.56 (m): C$_6\underline{H}_5$ and C$_6\underline{H}_4$NO$_2$.

IR (CHCl$_3$): 1763, 1744, 1676; 1609, 1603, 1583, 1526, 1492 cm$^{-1}$.

MS (EI) m/z: [M]$^+$=409, 304, 273, 201, 105, 77.

Example 29b trans-6-benzoyl-7-oxo-1,6-iazabicyclo[3.2.1]octane-2-carboxylic acid 89 mg of the ester obtained in Example 29a, 4 ml of acetone and 6 mg of 10% Pd/C catalyst are mixed together.

The reaction medium is left to react under agitation, at 20° C. and under a hydrogen atmosphere for 2 hours 45 minutes, then the catalyst is filtered and the filtrate evaporated under reduced pressure.

In this way 88 mg of a resin is obtained which is crystallized from 0.5 ml of ethyl ether.

In this way 54 mg of expected compound, of molecular formula $C_{14}H_{14}N_2O_4$ (M=274.278 g) is obtained. The corresponding yield is 91%.

1H NMR

In CDCl3, at 250 MHz, chemical shifts of the peaks in ppm and multiplicity:

1.96 (m), 2.10 (m) and 2.37 (m): N—CH—C$\underline{H}_2$—C$\underline{H}_2$; 3.13 (d) and 3.41 (dm): O=C—N—C$\underline{H}_2$; 4.10 (bd): O=C—N—CH; 4.52 (m): O=C—N—C$\underline{H}_2$—C$\underline{H}$; 7.44 (m): 7.56 (tt) and 7.69 (dd) C$_6\underline{H}_5$.

MS (EI) m/z: M$^+$=274, 229, 169, 105, 77.

Example 29c trans methyl 6-benzoyl-7-oxo-1,6-diazabicyclo[3.2.1]octane-2-carboxylate 2 ml of a solution of diazomethane at 12.7 g/l in dichloromethane is added under agitation to 28 mg (0.102 mmole) the acid obtained in Example 29b.

The solvent is evaporated off under reduced pressure and the residue is purified by chromatography on silica eluting with a dichloromethane/ethyl acetate mixture 98/2.

18.4 mg of expected compound, of molecular formula $C_{15}H_{16}N_2O_4$ (M=288.305 g) is recovered. The corresponding yield is 63%.

1H NMR

In CDCl3, at 300 MHz, chemical shifts of the peaks in ppm and multiplicity:

1.90 to 2.42: N—CH—C$\underline{H}_2$—C$\underline{H}_2$; 3.12 (d) and 3.44 (dt): O=C—N—C$\underline{H}_2$; 3.83 (s): C$\underline{H}_3$; 4.17 (bd): O=C—N—CH; 4.54 (m): O=C—N—C$\underline{H}_2$—C$\underline{H}$; 7.44 (t), 7.56 (t) and 7.69 (d): C$_6\underline{H}_5$.

MS (EI) m/z: [M]$^+$=288, 229, 183, 155, 105, 77.

Example 29d trans-6-benzoyl-7-oxo-N-(phenylmethyl)-1,6-diazabicyclo[3.2.1]octane-2-carboxamide 30 mg (0.109 mmole) of trans-6-benzoyl-7-oxo-1,6-diazabicyclo[3.2.1]octane-2-carboxylic acid obtained in Example 29b, 0.5 ml of dichloromethane, 23 mg of EDCI and 13 μl of benzylamine are mixed together.

The reaction medium is left to react for 30 minutes under agitation followed by diluting with dichloromethane, washing with a 10% aqueous solution of tartaric acid, decanting and drying the organic phase over sodium sulphate.

The solvent is evaporated off under reduced pressure in order to obtain a crude product which is purified by chromatography on silica eluting with a dichloromethane/acetone mixture 98/2.

In this way 19.5 mg of expected compound, of molecular formula $C_{21}H_{21}N_3O_3$ (M=363.419 g) is obtained. The corresponding yield is 49%.

1H NMR

In CDCl3, at 300 MHz, chemical shifts of the peaks in ppm and multiplicity:

1.97 (m), 2.34 (m) and 2.59 (m): N—CH—C$\underline{H}_2$—C$\underline{H}_2$; 2.90 (d), 3.33 (m), 3.99 (bd) and 4.50 (m): O=C—N—C$\underline{H}$, O=C—N—C$\underline{H}_2$—C$\underline{H}$, O=C—N—C$\underline{H}_2$, CO—NH—C$\underline{H}_2$—C$_6$H$_5$; 6.94 (bt): NH; 7.24 to 7.58 (m) and 7.68 (m): C$_6\underline{H}_5$—CO and C$_6\underline{H}_5$—CH$_2$.

IR (CHCl$_3$): 3411, 1763, 1680; 1603, 1583, 1519, 1498 cm$^{-1}$.

Example 29e 6-benzoyl—N—[methyl(phenylmethyl)]-7-oxo-1,6-diazabicyclo[3.2.1]octane-2-carboxamide The operation is carried out in a similar manner to Example 29d starting from 50 mg (0.182 mmole) of the acid obtained in Example 29b and 45 μl of N-methyl-benzylamine.

In this way 12 mg of expected compound, of molecular formula $C_{22}H_{23}N_3O_3$ (M=377.45 g) is recovered. The corresponding yield is 17%.

MS (EI) m/z: [M]$^+$=377, 272, 105.

Example 29f

6-benzoyl-2-(hydroxymethyl)-1,6-diazabicyclo[3.2.1]octan-7-one 100 mg (364 mmole) of trans-6-benzoyl-7-oxo-1,6-diazabicyclo[3.2.1]octane-2--carboxylic acid obtained in Example 29b is dissolved, under an inert atmosphere, in 3 ml of tetrahydrofuran.

The reaction medium is cooled down to −10° C. and 40 μl of methylmorpholine, then 38 μl of ethyl chloroformate are added.

The reaction medium is left to react for 15 minutes at −10° C., then the temperature is allowed to rise to 0° C. and 27 mg of $NaBH_4$, then, dropwise, 1.5 ml of methanol are added.

The reaction medium is left under agitation at 0° C. for 2 hours then left to return to ambient temperature.

3 ml of water is added, the reaction medium is left under agitation for 15 minutes, then a few drops of ammonium chloride are added. Extraction is carried out with ethyl acetate, followed by drying over magnesium sulphate, filtering and the solvent is evaporated off under reduced pressure.

In this way 85 mg of a crude product is obtained which is purified by chromatography on silica, eluting with a dichloromethane/methanol mixture 98/2.

In this way 25 mg of expected compound, of molecular formula $C_{14}H_{16}N_2O_3$ (M=260.3 g) is recovered. The corresponding yield is 26%.

1H NMR

In CDCl3, at 300 MHz, chemical shifts of the peaks in ppm and multiplicity:

1.61 (m, 1H), 2.00 (m, 2H) 2.30 (m, 1H): CH—C$\underline{H}_2$—C$\underline{H}_2$—CH; 2.19: 3.23 (d) and 3.26 (dt): N—C$\underline{H}_2$; 3.60 (m): N—C$\underline{H}$—CH$_2$—OH; 3.70 (m) and 3.77 (dd): CH—C$\underline{H}_2$—O; 4.56 (m): N—C$\underline{H}$—CH$_2$ 13 N.

MS (SIMS) m/z: [M+Na]$^+$=283, [M+H]$^+$=261, [M]$^+$=260, 229, 105.

Example 30 trans (4-nitrophenyl)methyl 6-acetyl-7-oxo-1,6-diazabicyclo[3.2.1]octane-2-carboxylate 1 g (2.63 mmoles) of the product prepared in Stage C of Example 29 is dissolved in 12 ml of dichloromethane. 250 μl of acetic anhydride is added, the reaction medium is left to react for 10 minutes under agitation, then diluted with dichloromethane and washed with a saturated aqueous solution of sodium hydrogen carbonate.

The organic phase is dried over sodium sulphate, followed by evaporating to dryness under reduced pressure in order to obtain 1.2 g of trans 1-(1,1-dimethylethyl) and 2-[(4-nitrophenyl)methyl]5-(acetylamino)-1,2-piperidinedicarboxylate, of molecular formula $C_{20}H_{27}N_3O_7$ (M=421.453 g).

This product is used without purification in stages similar to Stages E to G of Example 29 and in this way 14 mg of expected compound, of molecular formula $C_{16}H_{17}N_3O_6$ (M=347.330 g) is collected. The corresponding yield is 17%.

1H NMR

In CDCl3, at 300 MHz, chemical shifts of the peaks in ppm and multiplicity:

1.87 (m), 2.00 to 2.30 (m): N—CH—C$\underline{H}_2$—C$\underline{H}_2$; 2.54 (s): N—CO—C$\underline{H}_3$; 2.95 (d) and 3.21 (m): O═C—N—C$\underline{H}_2$; 4.26 (bd): O═C—N—C$\underline{H}$; 4.55 (m): O═C—N—CH$_2$—C$\underline{H}$; 5.34 [AB]: CO$_2$—C$\underline{H}_2$—C$_6$H$_4$; 7.57 and 8.25 [AA'BB']: C$_6$$\underline{H}_4$—NO$_2$.

MS (EI) m/z: [M]$^+$=347, 304, 211, 169, 125, 43.

Example 31 trans (4-nitrophenyl)methyl and 2-propenyl 7-oxo-1,6-diazabicyclo[3.2.1]octane-2,6-dicarboxylate 1.24 g (3.278 mmoles) of the product prepared in Stage C of Example 29a is dissolved, under a nitrogen atmosphere, in 8 ml of dichloromethane.

The solution is cooled down to 0° C., then 0.45 ml of TEA then 0.35 ml of allyl chloroformate are added dropwise.

The reaction medium is maintained at 0° C. for 15 minutes, then is left to react under agitation for 1 hour at ambient temperature, followed by diluting with 20 ml of dichloromethane, washing with an aqueous solution of sodium bicarbonate, and twice with water, drying over magnesium sulphate, and the solvent is evaporated off under reduced pressure.

In this way 1.5 g of trans 1-(1,1-dimethylethyl) and 2-[(4-nitrophenyl)methyl]5-[[(2-propenyloxy)carbonyl]amino]-1,2--piperidinedicarboxylate of molecular formula $C_{22}H_{28}N_3O_8$, (M=462.486 g) is obtained.

The corresponding yield is 99%.

This product is used in stages similar to Stages E to G of Example 29a and in this way 30.6 mg of expected compound, of molecular formula $C_{18}H_{19}N_3O_7$, (M=389.368 g) is obtained in the form of a white solid. The corresponding yield is 40%.

1H NMR

In CDCl3, at 300 MHz, chemical shifts of the peaks in ppm and multiplicity:

1.91 (m), 2.00 to 2.29 (m): N—CH—C$\underline{H}_2$—C$\underline{H}_2$; 2.98 (d) and 3.25 (bd): O═C—N—C$\underline{H}_2$; 4.27 (t) O═C—N—C$\underline{H}$; 4.37 (bs): O═C—N—CH$_2$—C$\underline{H}$; 4.77 (bd): COO—C$\underline{H}_2$—CH═; 5.33 (s): COO—C$\underline{H}_2$—C$_6$H$_4$; 5.29 to 5.46: C$\underline{H}_2$═CH; 5.98 (m): CH$_2$═C$\underline{H}$; 7.96 and 8.29 [AA'BB']: C$_6$$\underline{H}_4$—NO$_2$.

IR (CHCl$_3$): 1801, 1775, 1738, 1724; 1649; 1608, 1595, 1526 cm$^{-1}$.

MS (positive electrospray) m/z: [2M+Na]$^+$=801, [M+Na+CH$_3$CN]$^+$=453, [M+Na]$^+$=412

Example 31a trans phenylmethyl 6-benzoyl-7-oxo-1,6-diazabicyclo[3.2.1]octane-2-carboxylate 200 mg of trans phenylmethyl 5-(benzoylamino)-1-(chlorocarbonyl)-2-piperidinecarboxylate, of molecular formula $C_{21}H_{21}ClN_2O_4$ (M=400.87 g), prepared in a similar manner to Stages A to F of Example 29a and 6 ml of anhydrous tetrahydrofuran are mixed together under an inert atmosphere and the reaction medium is cooled down to −78° C.

0.55 ml of a 1M solution of lithium bis (trimethylsilyl) amide in tetrahydrofuran is added dropwise.

The reaction medium is left to react under agitation at −78° C. for 10 minutes then 25 μl of acetic acid is added.

The temperature is allowed to rise to ambient temperature, then the reaction medium is poured into 10 ml of a 10% aqueous solution of tartaric acid, followed by extracting with ethyl acetate, washing with an aqueous solution of phosphate buffer at pH=7, then with water, drying over magnesium sulphate and bringing to dryness by evaporation of the solvent under reduced pressure.

In this way 158 mg of a crude product is obtained which is purified by chromatography on silica, eluting with a dichloromethane/acetone mixture 98/2.

In this way 70 mg of expected compound, of molecular formula $C_{21}H_{20}N_2O_4$ (M=364.40 g) is recovered. The corresponding yield is 39%.

1H NMR

In CDCl3, at 400 MHz, chemical shifts of the peaks in ppm and multiplicity:

2.15 (m) and 2.25 (m): NCH—$CH_2$—$CH_2$—CH—$CO_2$; 1.94 (m) and 2.36 (m): NCH—$CH_2$—$CH_2$—CH—$CO_2$; 4.20 (d) N—$CH$—$CO_2$; 4.50 (q): NC$H$—$CH_2$—$CH_2$—CH—$CO_2$; 3.08 (d) and 3.40 (dt): N—C$H_2$; 5.25 [AB]: $CO_2$—$CH_2$—$C_6H_5$; 7.38 (bs): $CH_2$—$C_6H_5$; 7.43 (bt) and 7.55 (bt) and 7.69 (bd) $C_6H_5$—CO.

IR (CHCl$_3$): 1764, 1744, 1675; 1602, 1584, 1498 cm$^1$.

MS (SIMS) m/z: [M+Na]$^+$=387, [M+H]$^+$=365, 259, 257, 229, 105, 91.

Example 31b phenylmethyl 6-benzoyl-7-oxo-1,6-diazabicyclo [3.2.1]oct-2-ene-2-carboxylate 46 mg (0.126 mmoles) of the product obtained in Example 31a and 0.5 ml of anhydrous tetrahydrofuran are mixed together, under a nitrogen atmosphere.

The reaction medium is cooled down to −70° C. and 0.31 ml of 1M lithium bis (trimethylsilyl) amide in tetrahydrofuran is added.

The reaction medium is left to react for 2 hours at −70° C., then the temperature is allowed to rise to −15° C. and 0.41 ml of a solution of $C_6H_5$—SeCl at 0.7 mol/l in THF is added at this temperature.

The reaction medium is left under agitation at −15° C. for 15 minutes, then left to return to ambient temperature over 15 minutes and poured into a mixture of water and ice containing a few drops of a saturated aqueous solution of sodium bicarbonate.

Extraction is carried out with ethyl acetate, followed by washing with water, drying and the solvent is evaporated off under reduced pressure.

The residue is purified by chromatography on silica eluting with a dichloromethane/acetone mixture 98/2 and in this way 15 mg of phenylmethyl 6-benzoyl-7-oxo-2-(phenylselenyl)-1,6-diazabicyclo[3.2.1]octane-2-carboxylate, of molecular formula $C_{27}H_{24}N_2O_4Se$ (M=519.46 g) is collected. The corresponding yield is 23%.

15 mg (0.029 mmole) of the compound obtained previously and 0.3 ml of dichloromethane are mixed together.

The reaction medium is cooled down to 0° C. and 15 mg of meta-chloroperbenzoic acid in solution in 0.15 ml of dichloromethane is added.

The reaction medium is left under agitation at 0° C. for 15 minutes, then left to return to ambient temperature, followed by pouring into approximately 20 ml of water, extracting with dichloromethane and washing the organic phase with an aqueous solution of phosphate buffer at pH=7, drying over magnesium sulphate, filtering and the solvent is evaporated off under reduced pressure.

In this way 15 mg of crude product is obtained which is purified on silica eluting with a dichloromethane/acetone mixture 98/2.

In this way 5 mg of expected compound, of molecular formula $C_{21}H_{18}N_2O_4$ (M=362.39 g) is recovered. The corresponding yield is 48%.

1H NMR

In CDCl3, at 300 MHz, chemical shifts of the peaks in ppm and multiplicity: 2.66 (td) and 2.99 (tdd): N—CH—$CH_2$; 3.03 (d) and 3.77 (ddd): N—$CH_2$; 4.76 (tt): N—$CH$; 5.23 [AB]: CO2-$CH_2$—$C_6H_5$; 7.02 (dt): N—C=CH; 7.30 to 7.38 (m): $CH_2$—$C_6H_5$; 7.42 (tm), 7.54 (tm) and 7.62 (dm); $C_6H_5$—CO;

Example 31c 6-benzoyl-7-oxo-1,6-diazabicyclo[3.2.1]oct-2-ene-2-carboxylic acid 20 mg (0.055 mmole) of the product obtained in Example 31b is mixed, 0.4 ml of acetone and 4 mg of 10% Pd/C catalyst are added.

The reaction medium is placed under a hydrogen atmosphere and left to react for 3 hours under vigorous agitation.

Filtration is carried out and the catalyst is washed with acetone then with methanol. The filtrate is evaporated under reduced pressure.

In this way 14 mg of expected compound, of molecular formula $C_{14}H_{12}N_2O_4$ (M=272.4 g) is obtained. The corresponding yield is 93%.

MS (EI) m/z: [M]$^+$: 272, 105.

Example 32a trans 2-propenyl 7-oxo-6-(2-phenylmethoxy)-1,6-diazabicyclo[3.2.1]octane-2-carboxylate Stage A cis 2-propenyl 5-hydoxy-1-[(trifluoroacetyl)-2-piperidinecarboxylate 17 g (0.059 mole) of cis 1-(1,1-dimethylethyl) and 2-(2-propenyl) 5-hydroxy-1,2-piperidinedicarboxylate (described in Rec. Trav. Chim. (1959), 78, 648-658), of molecular formula $C_{14}H_{23}NO_5$ (M=285.3431 g) is dissolved in 17 ml ethyl acetate.

A solution of 51 ml of hydrogen chloride in ethyl acetate at 150 g/l is added at 0° C.

The reaction medium is left to return to ambient temperature and left to react under agitation for 1 hour 30 minutes.

The ethyl acetate is evaporated under reduced pressure, followed by taking up in ethyl ether, which is in turn eliminated under reduced pressure.

In this way 12 g of a pale yellow solid is obtained which is mixed with 200 ml of tetrahydrofuran. The reaction medium is cooled down to 0° C., then 37.6 ml of TEA is added.

The temperature is maintained at 0° C., then 16.8 ml of trifluoroacetic anhydride is added slowly.

The temperature is allowed to rise to 20° C. and the reaction medium is left to react for another 20 minutes under agitation.

Then 20 ml of water is added.

The solution obtained is agitated for 1 hour at ambient temperature and poured into 300 ml of water, followed by extracting with ethyl acetate, washing with water, drying over sodium sulphate, and the solvent is evaporated off under reduced pressure.

15.7 g of crude product is obtained which is purified by chromatography on silica eluting with a dichloromethane/ ethyl acetate mixture 90/10.

In this way 12.3 g of expected compound, of molecular formula $C_{11}H_{14}F_3NO_4$ (M=281.23 g), is obtained in the form of a yellow oil. The corresponding yield is 73%.

Stage B trans 2-propenyl 5-[(phenylmethoxy)amino]-1-(trifluoroacetyl) 2-piperidinecarboxylate 10.9 g (38.7 mmoles) of the compound obtained in Stage A and 150 ml of acetonitrile are mixed together.

The pale yellow solution obtained is cooled down to −30° C., then, 4.94 ml of 2,6-lutidine and 6.7 ml of trifluoromethanesulphonic anhydride are added. Agitation is carried out for 15 minutes, then, still at −30° C., 9.57 g of O-benzylhydroxylamine is added.

At end of the addition, the temperature is left to rise to 0° C. and the reaction medium is left to react for 1 hour at this temperature. Then 4.9 ml of 2,6-lutidine is added and the reaction medium is left in contact for 3 days at 0° C., followed by pouring into 500 ml of water, extracting with ethyl acetate, washing successively with water, with an aqueous solution of phosphate buffer at pH=7.0, with a saturated aqueous solution of sodium chloride, then again with water.

After drying over sulphate sodium, the solvent is evaporated off under reduced pressure.

In this way 23 g of crude product is obtained which is dissolved in 150 ml of dichloromethane, followed by washing with a 10% aqueous solution of tartaric acid, drying over sodium sulphate and the solvent is evaporated off under reduced pressure.

In this way 16.1 g of a yellow oil is recovered which is purified by chromatography on silica.

12.1 g of expected compound, of molecular formula $C_{18}H_{21}F_3N_2O_4$ (M=386.37 g) is recovered in crystallized form. The corresponding yield is 72%.

Stage C trans 2-propenyl 5-[(phenylmethoxy)amino]-2-piperidine carboxylate 80 ml of methanol is cooled down to −10° C., then 4.15 g (37.8 mmoles) of $NaBH_4$ is added.

A solution of 10.6 g (27.4 mmoles) of the compound obtained previously in 80 ml of methanol is added slowly, under agitation, over 30 minutes, to this mixture whilst maintaining the temperature at −10° C.,.

Then the temperature is allowed to rise to 0° C., then this temperature is maintained for 3 hours.

The reaction mixture is poured into 450 ml of ice and water and 150 ml ethyl acetate, followed by decanting, washing with water, drying the organic phase over sodium sulphate and then the solvent is evaporated off under reduced pressure.

In this way 8.2 g of a yellow oil is obtained which is dissolved in 80 ml of tetrahydrofuran, a solution of 2.43 g of oxalic acid in 25 ml of THF is added. The oxalate which crystallizes is filtered and washed with a little THF then dried under reduced pressure and dissolved in a saturated solution of sodium bicarbonate. Extraction is carried out with ethyl acetate, followed by washing the organic phase with water, drying over sodium sulphate and the solvent is evaporated off under reduced pressure.

In this way 4.39 g of expected compound, of molecular formula $C_{16}H_{22}N_2O_3$ (M=290.36 g), is obtained in the form of an oil which crystallizes when the temperature is below 20° C. The corresponding yield is 55%.

Stage D trans 2-propenyl 7-oxo-6-(2-phenylmethoxy)-1,6-diazabicyclo[3.2.1]-octane-2-carboxylate 3.2 g (11 mmoles) of the oil obtained previously is dissolved under a nitrogen atmosphere in 500 ml of acetonitrile.

The solution obtained is cooled down to 0° C. using an ice bath and 3.37 ml of TEA, then 0.796 ml of diphosgene, and 1.48 g of DMAP are added.

The temperature is allowed to rise to 20° C. and the reaction medium is left to react for 2 hours under agitation.

Then the reaction mixture is poured into 200 ml of a 0.1 N aqueous solution of hydrochloric acid, 400 ml of water is added, followed by extracting with dichloromethane, washing with water and drying over sodium sulphate.

Then the solvent is evaporated off under reduced pressure so as to obtain 3.1 g of expected compound, of molecular formula $C_{17}H_{20}N_2O_4$ (M=316.36 g), in the form of crystals. The corresponding yield is 89%.

1H NMR 1.66 (m) and 2.00 to 2.16 (m) O=C—CH—C$\underline{H}_2$—C$\underline{H}_2$; 2.94 (d) and 3.07 (dt) N—C$\underline{H}_2$; 3.31 (m) N—CH$_2$—C$\underline{H}$; 4.14 (dd) O=C—C$\underline{H}$, 4.68 (dt) C$\underline{H}_2$—CH=CH$_2$; 4.90 and 5.06 [AB]C$\underline{H}_2$—C$_6$H$_5$; 5.26 (dq) and 5.34 (dq) CH$_2$—CH=C$\underline{H}_2$; 5.92 (m) CH$_2$—C$\underline{H}$=CH$_2$; 7.37 to 7.42 (m) C$_6\underline{H}_5$.

IR (CHCl$_3$): 1748; 1646; 1496 cm$^{-1}$.

MS (positive electrospray) m/z: [2M+Na]$^+$=655, [M+Na+CH$_3$CN]$^+$=380, [M+Na]$^+$=339, [M+H]$^+$=317, 289, 91.

Example 32b trans-7-oxo-6-(phenylmethoxy)-1,6-diazabicyclo [3.2.1]octane-2-carboxylic acid and its cyclohexylamine salt.

2.21 g (6.98 mmoles) of the compound obtained in Example 32a is dissolved under a nitrogen atmosphere in 44 ml of dichloromethane.

A 0.5M solution of sodium ethyl-hexanoate in ethyl acetate is added.

Then 242 mg of tetrakistriphenylphosphine palladium is added in one go, then the reaction medium is maintained under agitation for 1 hour, followed by diluting with 22 ml ethyl acetate, pouring into 75 ml of a saturated solution of NaH$_2$PO$_4$, extracting with ethyl acetate and drying the organic phase over sodium sulphate. The solvent is evaporated off under reduced pressure in order to obtain 3.5 g of a yellow residue which is dissolved in a mixture of 11 ml of ethyl acetate and 0.8 ml of cyclohexylamine.

The crystallized cyclohexylamine salt is separated by filtration and washed with ethyl ether, then the solvent is evaporated off under reduced pressure. In this way a total 2.51 g of crystallized salt is obtained which is dissolved in 25 ml of a saturated aqueous solution of NaH$_2$PO$_4$. After extraction with ethyl acetate, the organic phases are combined and dried over sodium sulphate, then the solvent is evaporated off under reduced pressure.

In this way 1.82 g of expected compound of molecular formula $C_{14}H_{16}N_2O_4$ (M=276.29 g), is recovered in crystallized form. The corresponding yield is 94%.

1H NMR

In CDCl3, at 300 MHz, chemical shifts of the peaks in ppm and multiplicity:

1.68 (m) and of 2.20 to 2.22 (m): CH—C$\underline{H}_2$—C$\underline{H}_2$—CH; 2.89 (d) and 3.11 (ddd): N—C$\underline{H}_2$; 3.34 (dd) N—C$\underline{H}_2$—CH, 4.13 (bd): N—C$\underline{H}$—C=O; 4.90 and 5.05 [AB]: C$\underline{H}_2$—O; 7.32 to 7.43: C$_6\underline{H}_5$.

MS (SIMS) m/z: [M+Na]$^+$=299, [M+H]$^+$=277.91.

Example 33a pyridinium salt of trans-7-oxo-6-(sulphooxy)-1,6-diazabicyclo[3.2.1]octane-2-carboxamide Stage A trans-7-oxo-6-(phenylmethoxy)-1,6-diazabicyclo[3.2.1]octane-2-carboxamide 1.1 g (4 mmole) of the compound obtained in Example 32b is dissolved in 30 ml of dichloromethane.

0.67 ml of TEA is added to this solution.

The solution is cooled down to 5° C. and 0.57 ml of isobutyl chloroformate is added quite quickly.

The reaction medium is maintained under agitation for 20 minutes at 5° C., then 3 ml of concentrated ammonia is added slowly, under vigorous agitation,.

Agitation is maintained for one hour at ambient temperature, the reaction medium is diluted with 30 ml of water, followed by extracting with dichloromethane, washing with water, drying over sodium sulphate and concentrating under reduced pressure.

In this way 1.1 g of expected product of molecular formula $C_{14}H_{17}N_3O_3$ (M=275.31 g) is obtained. The yield is quantitative.

Stage B trans-6-hydroxy-7-oxo-1,6-diazabicyclo[3.2.1]octane-2-carboxamide 1.1 g of the compound obtained in Stage A, 30 ml of methanol and 300 mg of 10% Pd/C are mixed together.

The reaction medium is placed under a hydrogen atmosphere then the mixture is agitated vigorously for 45 minutes.

The catalyst is then filtered, followed by washing with methanol then with a dichloromethane/methanol mixture.

The filtrate is evaporated under reduced pressure.

In this way 800 mg of expected product of molecular formula $C_7H_{11}N_3O_3$ (M=185.18 g) is obtained in the form of a colourless foam.

Stage C

Pyridinium salt of trans-7-oxo-6-(sulphooxy)-1,6-diazabicyclo[3.2.1]octane-2-carboxamide 800 mg of the compound obtained previously and 20 ml of anhydrous pyridine are mixed together under a nitrogen atmosphere.

Then 1.91 g of SO$_3$-pyridine complex is added.

The mixture is agitated for 20 hours at ambient temperature.

The reaction medium is then filtered and the solvent evaporated off under reduced pressure.

In this way the expected product of molecular formula C12H$_{16}$N$_4$O$_6$S, C$_5$H$_5$N (M=344.35 g) is obtained in the form of a yellow product.

Example 33b

Tetrabutylammonium salt of trans-7-oxo-6-(sulphooxy)-1,6-diazabicyclo[3.2.1]octane-2-carboxamide The product obtained previously is introduced into 40 ml of a concentrated aqueous solution of NaH$_2$PO$_4$ so as to obtain a pH of 4.

Extraction is carried out with ethyl acetate then 1.01 g of tetrabutyl ammonium hydrogen sulphate is added to the aqueous phase Agitation is carried out for 10 minutes at ambient temperature, followed by extracting with 4 times 300 ml ethyl acetate, drying the organic phase over sodium sulphate and concentrating under reduced pressure.

In this way 1.530 g of a colourless foam is obtained which is purified by chromatography on silica, eluting with an acetone/dichloromethane/TEA solvent 50/48/2.

In this way 1.02 g of expected product of molecular formula $C_{23}H_{46}N_4O_6S$ (M=506.71 g), is recovered in the form of a colourless foam. The corresponding overall yield is 50%.

Example 33c

Sodium salt of trans-7-oxo-6-(sulphooxy)-1,6-diazabicyclo[3.2.1]octane-2-carboxamide The product obtained in Example 33b is dissolved in 7 ml of an acetone/water mixture 1/1 then deposited on a column of 180 g of DOWEX 50WX8 resin in Na$^+$ form and eluted with water. After evaporation of the water under reduced pressure, the product crystallizes.

In this way 542 mg of expected compound, of formula $C_7H_{10}N_3NaO_6S$ (M=287.23 g) is obtained. The corresponding yield is 94%.

1H NMR

In DMSO, at 300 MHz, chemical shifts of the peaks in ppm and multiplicity:

1.55 to 2.10 (3H): CH—C$\underline{H}_2$—C$\underline{H}_2$—CH; 2.91 (d) and 3.02 (bd): N—C$\underline{H}_2$; 3.38 (bs): N—C$\underline{H}_2$—C$\underline{H}$; 3.68 (d): N—C$\underline{H}$—C=O; 7.23 and 7.44: N$\underline{H}_2$.

MS (negative electrospray) m/z: [M]$^-$=264

Examples 34 to 47

The following carboxamides were prepared following an operating method similar to that which is used in Example 33 starting from 110 mg of the acid obtained in Example 32b.

The only difference is that in Stage 1, the reagent used, i.e. the ammonia solution, is replaced by a solution of the corresponding amine.

Thus, only the Rl group as defined for formula I varies.

Example 34

Starting from 49 μl of benzylamine, 64 mg of the sodium salt of trans-7-oxo-N-(phenylmethyl)-6-(sulphooxy)-1,6-diazabicyclo[3.2.1]octane-2-carboxamide is obtained i.e. an overall yield of 38%.

MS (positive electrospray) m/z: [M+Na]$^+$=400, [M+H]$^+$=378

Example 35

Starting from 43 µl of 2-pyridinemethanamine, 37 mg the sodium salt of trans-7-oxo-N-(2-pyridinylmethyl)-6-(sulphooxy)-1,6-diazabicyclo[3.2.1]octane-2-carboxamide is obtained i.e. an overall yield of 14%.

MS (positive electrospray) m/z: $[M+H]^+=379$

Example 36

Starting from 51.3 mg of 3-pyridineethanamine, 42 mg of the sodium salt of trans-7-oxo-N-[2-(3-pyridinyl)ethyl]-6-(sulphooxy)-1,6-diazabicyclo[3.2.1]octane-2-carboxamide is obtained i.e. an overall yield of 20%.

MS (positive electrospray) m/z: $[M+H]^+=393$

Example 37

Starting from of 51.3 mg of 4-pyridineethanamine, 40 mg of the sodium salt of trans-7-oxo-N-[2-(4-pyridinyl)ethyl]-6-(sulphooxy)-1,6-diazabicyclo[3.2.1]octane-2-carboxamide is obtained i.e. a yield of 20%.

MS (positive electrospray) m/z: $[M+Na]^+=415$, $[M+H]^+=393$

Example 38

Starting from 50.2 mg of 2-pyridineethanamine, 45 mg of the sodium salt of trans-7-oxo-N-[2-(2-pyridinyl)ethyl]-6-(sulphooxy)-1,6-diazabicyclo[3.2.1]octane-2-carboxamide is obtained i.e. a yield of 23%.

MS (positive electrospray) m/z: $[M+H]^+=393$

Example 39

Starting from 58.3 mg of 3-amino-benzamide, 43 mg of the sodium salt of trans-N-[3-(aminocarbonyl)phenyl]-7-oxo-6-(sulphooxy)-1,6-diazabicyclo[3.2.1]octane-2-carboxamide is obtained i.e. a yield of 22%.

MS (negative electrospray) m/z: $[M]^-=383$

Example 40

Starting from 58.3 mg of 4-dimethylamino-benzenamine, 65.3 mg of the sodium salt of trans-N-[4-(dimethylamino)phenyl]-7-oxo-6-(sulphooxy)-1,6-diazabicyclo[3.2.1]octane-2-carboxamide is obtained i.e. a yield of 40%.

MS (negative electrospray) m/z: $[M]^-=383$

Example 41

Starting from 58.3 mg of 3-dimethylamino-benzenamine, 91 mg of the sodium salt of trans-N-[3-(dimethylamino)phenyl]-7-oxo-6-(sulphooxy)-1,6-diazabicyclo[3.2.1]octane-2-carboxamide is obtained i.e. a yield of 54%.

MS (negative electrospray) m/z: $[M]^-=383$

Example 42

Starting from 43 µl of 4-pyridinemethanamine, 24.6 mg of the sodium salt of trans-7-oxo-N-[(4-pyridinyl)methyl]-6-(sulphooxy)-1,6-diazabicyclo[3.2.1]octane-2-carboxamide is obtained i.e. a yield of 15%.

MS (negative electrospray) m/z: $[M]^-=355$

Example 43

Starting from 44 µl of 3-pyridinemethanamine, 44.7 mg of the sodium salt of trans-7-oxo-N-(3-pyridinylmethyl)-6-(sulphooxy)-1, 6-diazabicyclo[3.2.1]octane-2-carboxamide is obtained i.e. a yield of 26%.

MS (negative electrospray) m/z: $[M]^-=355$

Example 44

Starting from 84 mg (+−)-alpha-amino-benzenepropanamide, 55 mg of the sodium salt of trans-N-(1-amino-1-oxo-3-phenyl-2-propyl)-7-oxo-6-(sulphooxy)-1,6-diazabicyclo[3.2.1]octane-2-carboxamide is obtained i.e. a yield of 27%.

MS (negative electrospray) m/z: $[M]^-=411, 321$

Example 45

Starting from 46 mg of hydrochloride of 2-amino-acetamide and 61 µl of TEA, 25 mg of the sodium salt of trans-N-(2-amino-2-oxoethyl)-7-oxo-6-(sulphooxy)-1,6-diazabicyclo[3.2.1]octane-2-carboxamide is obtained i.e. a yield of 13%.

MS (negative electrospray) m/z: $[M]^-=321, 249$

Example 46

Starting from 64 mg of (3-aminophenyl)-urea, 43 mg of the sodium salt of trans-N-[3-[(aminocarbonyl)amino]phenyl]-7-oxo-6-(sulphooxy)-1,6-diazabicyclo[3.2.1]octane-2-carboxamide is obtained i.e. a yield of 24%.

MS (negative electrospray) m/z: $[M]^-=398, 153, 111$

Example 47

Starting from 63 mg of (+−)-alpha-amino-benzeneacetamide, 64 mg of the sodium salt of trans-N-(2-amino-2-oxo-1-phenylethyl)-7-oxo-6-(sulphooxy)-1,6-diazabicyclo[3.2.1]octane-2-carboxamide is obtained i.e. a yield of 38%

MS (negative electrospray) m/z: $[M]^-=397$

Examples 48 to 51

The following compounds were prepared from 110 mg of the compound obtained in Stage E of Example 32, which is esterified each time with the appropriate alcohol in order to obtain the final product.

Then, the operation is carried out in a similar manner to that described in Stages B to E of Example 33.

Example 48

Starting from 31.5 mg of 2-hydroxy-acetamide, 54 mg of the sodium salt of trans 2-amino-2-oxoethyl 7-oxo-6-(sulphooxy)-1,6-diazabicyclo[3.2.1]octane-2-carboxylate is obtained i.e. a yield of 32%.

MS (negative electrospray) m/z: $[M]^-=322$

Example 49

Starting from 51.7 mg of 4-pyridineethanol, 20 mg of the sodium salt of trans 2-(4-pyridinyl)ethyl 7-oxo-6-(sulphooxy)-1,6-diazabicyclo[3.2.1]octane-2-carboxylate is obtained i.e. a yield of 8.5%.

MS (negative electrospray) m/z: $[M]^-=370$

Example 50

Starting from 47.3 mg of 2-pyridineethanol, 47 mg of the sodium salt of trans 2-(2-pyridinyl)ethyl 7-oxo-6-(sulphooxy)-1,6-diazabicyclo[3.2.1]octane-2-carboxylate is obtained i.e. a yield of 23.4%.

MS (negative electrospray) m/z: [M]$^-$=370

Example 51

Starting from 57.7 mg of 3-pyridineethanol, 50 mg of the sodium salt of trans 2-(3-pyridinyl)ethyl 7-oxo-6-(sulphooxy)-1,6-diazabicyclo[3.2.1]octane-2-carboxylate is obtained i.e. a yield of 26%.

MS (negative electrospray) m/z: [M]$^-$=370

Example 52

Sodium salt of 3-methoxy-6-(sulphooxy)-1,6-diazabicyclo[3.2.1]oct-3-in-7-one

Stage A 10 g (50 mmoles) of 1,1-dimethylethyl 3,5-dioxo-1-piperidinecarboxylate is dissolved in 10 ml of methanol, then 6 g (54 mmoles) of O-allylhydroxylamineamine hydrochloride is added.

The reaction medium is left under agitation for 3 hours, then the solvent is evaporated off under reduced pressure.

The residue is taken up in water, followed by extracting with dichloromethane, washing the organic phase with water, then drying it over sodium sulphate.

After filtration and evaporation of the solvent under reduced pressure, 10.6 g of 1,1-dimethylethyl 5-methoxy-3-[(2-propenyloxy)imino]-3,6-dihydro-1(2H)-pyridinecarboxylate of molecular formula $C_{14}H_{22}N_2O_4$ (M=282.342 g) is obtained. The corresponding yield is 75%.

Stage B 10.6 g (37.6 mmoles) of the product obtained in Stage A and 212 ml of methanol are placed in a flask.

The solution is cooled down to −5° C., 37.8 g sodium cyanoborohydide, then 58.2 ml of boron fluoride etherate are added, followed by diluting with dichloromethane, pouring onto a mixture of water and 2N soda, extracting with dichloromethane, washing the organic phase with water, drying over sodium sulphate, filtering and the solvent is evaporated off under reduced pressure.

The product obtained is purified by chromatography on silica eluting with an AcOEt/dichloromethane mixture 10/90.

In this way 5.5 g of 1,1-dimethylethyl 5-methoxy-3-[(2-propenyloxy)amino]-3,6-dihydro-1(2H)-pyridinecarboxylate of molecular formula $C_{14}H_{24}N_2O_2$ (M=284.36 g) is obtained.

The corresponding yield is 51%.

Stage C 5.5 g (19.3 mmoles) of the product obtained in Stage B, 27.5 ml of dichloromethane and 4.2 ml of anisole are introduced into a flask.

Then 27.5 ml of trifluoroacetic acid is added.

The TFA and dichloromethane are eliminated under reduced pressure.

The residue is taken up in water and extraction is carried out 3 times with AcOEt. The aqueous phase is rendered basic by the addition of ammonium hydroxide, then extracted with AcOEt.

The organic phases are washed with water, followed by drying over sodium sulphate, filtering, then the solvent is evaporated off under reduced pressure.

In this way 2.45 g of 5-methoxy-N-(2-propenyloxy)-1,2,3,6-tetrahydro-3-pyridinamine of molecular formula $C_9H_{16}N_2O_2$ (M=184.24 g) is obtained.

The corresponding yield is 69%.

Stage D 2.45 g (0.0133 mmole) of the product obtained in Stage C is dissolved under an inert atmosphere in 826 ml of acetonitrile and the solution is cooled down to 0° C.

0.778 ml of diphosgene is added.

The temperature is allowed to rise to ambient temperature, then 5.56 ml of TEA is added.

Agitation is carried out overnight at ambient temperature, then the solvent is evaporated off under reduced pressure.

The residue is taken up in water, followed by extracting with AcOEt, washing the organic phase with water, drying over sodium sulphate, filtering, then the solvent is evaporated off under reduced pressure.

The residue is purified by chromatography on silica eluting with an AcOEt/dichloromethane mixture 1/9.

In this way 1.13 g of 3-methoxy-6-(2-propenyloxy)-1,6-diazabicyclo[3.2.1]oct-3-in-7-one of molecular formula $C_{10}H_{14}N_2O_3$ (M=210.23 g) is recovered.

The corresponding yield is 40.3%.

Stage E

In a flask placed under an inert atmosphere, 105 mg (0.5 mmole) of the product obtained in Stage D is dissolved in 1.1 ml of dichloromethane, 57 μl of acetic acid, then 317 mg of Pd[P($C_6H_5$)$_3$]$_4$ are added.

After reaction for 1 hour, 1.1 ml of pyridine, then 238 mg of $SO_3$-pyridine complex are added.

The reaction medium is left under agitation overnight, then the solvent is evaporated off under reduced pressure.

The residue is taken up in water, followed by extracting with dichloromethane, washing with water, drying the organic phase over sodium sulphate, filtering and the solvent is evaporated off under reduced pressure.

The residue is purified by chromatography on silica, eluting with a trichloromethane/acetonitrile mixture 50/50.

In this way 148 mg of the 1-propenyltriphenylphosphonium salt of 3-methoxy-6-(sulphooxy)-1,6-diazabicyclo[3.2.1]oct-3-in-7-one of molecular formula $C_{28}H_{29}N_2O_6PS$ is recovered.

The corresponding yield is 53%.

Stage F 148 mg of the product obtained in Stage E is dissolved in water containing 10% THF.

The solution obtained is passed through a column of DOWEX 50WX8 resin in Na$^+$ form, eluting with water containing 10% THF.

The product collected is lyophilized in order to obtain 51 mg of the expected sodium salt, of molecular formula $C_7H_9N_2O_6SNa$ (M=272.21 g).

The corresponding yield is 70%.

1H NMR 3.04 (d) and 3.25 (dd): C=CH—CH—C$\underline{H}_2$—N; 3.41 (d) and 3.71 (dd): N—C$\underline{H}_2$—C=CH; 3.47 (s): CH$_3$—O; 4.20 (dd): C=CH—C$\underline{H}$—CH$_2$—N; 5.19 (bd): C=C$\underline{H}$—CH—CH$_2$—N MS (negative electrospray) m/z: [M]$^-$=249, [M—CH$_3$]$^-$=235

Example 53

Sodium salt of 6-(sulphooxy)-1,6-diazabicyclo[3.2.1]oct-3-in-7-one.

Stage A 1.03 g (5.2 mmoles) of 1,1-dimethylethyl 3,6-dihydro-3-oxo-1(2H)-pyridinecarboxylate of molecular formula $C_{10}H_{15}NO_3$ is dissolved in 15 ml of ethanol. 572 mg (5.2 mmoles) of O-allylhydroxylamineamine, then 1.3 ml of pyridine are added.

The reaction medium is left under agitation for 15 minutes, then 100 ml of dichloromethane is added, followed by washing with a 10% aqueous solution of tartaric acid, drying the organic phase over magnesium sulphate, filtering and the solvent is evaporated off under reduced pressure.

In this way 1.36 g of 1,1-dimethylethyl 3,6-dihydro-3-[(2-propenyloxy)imino]-1(2H)-pyridinecarboxylate of molecular formula $C_{13}H_{20}N_2O_3$ (M=252.32 g) is obtained.

The corresponding yield is quantitative.

Stage B

The operation is carried out as indicated in Stage A of Example 52 starting from 1.38 g of the product obtained in Stage A, 15.1 g of sodium cyanoborohydide and 8.3 ml of boron trifluoride etherate.

In this way 0.99 g of a mixture of 2/3 of 1,1-dimethylethyl 3-[(2-propenyloxy)amino]-1-piperidinecarboxylate and 1/3 of 1,1-dimethylethyl 3,6-dihydro-3-[(2-propenyloxy)amino]-1(2H)-pyridine carboxylate of molecular formula $C_{13}H_{22}N_2O_3$ (M=254.33 g) is recovered after purification.

The corresponding yield is 71%.

Stage C 1.07 g (4.26 mmoles) of a mixture obtained in Stage B is dissolved in 2 ml of AcOEt. The reaction medium is cooled down to 0° C., then 5.8 ml of a 7.3 M solution of hydrogen chloride in AcOEt is added and the medium is left to react for 2 hours 30 minutes at 0° C.

The solvent is evaporated off under reduced pressure, followed by taking up in ether, filtering the precipitate and drying under reduced pressure.

In this way 560 mg of N-(2-propenyloxy)-1.2,3,6-tetrahydro-3-pyridinamine dihydrochloride of molecular formula $C_8H_{16}Cl_2N_2O$ (M=227.14 g) is obtained.

The corresponding yield is 57%.

Stage D 560 mg (2.46 mmoles) of the product obtained in Stage C is dissolved in 6 ml of dichloromethane, then 2.5 ml of 2N soda is added.

After decanting, the aqueous phase is extracted with AcOEt.

The organic phases are combined, followed by drying over magnesium sulphate and filtering, then the solvent is evaporated off under reduced pressure.

In this way 278 mg of N-(2-propenyloxy)-1.2,3,6-tetrahydro-3-pyridinamine of molecular formula $C_8H_{14}N_2O$ (M=154.21 g) is obtained.

The corresponding yield is 73%.

Stage E 270 mg (1.75 mmoles) of the product obtained in Stage D is dissolved under an argon atmosphere in 45 ml of acetonitrile, 760 µl of TEA and 105 µl of diphosgene are added.

The reaction medium is left to react for 15 minutes at 0° C., then left to return to ambient temperature and left to react for another 2 hours.

Then 213 mg of DMAP is added and the medium is left to react overnight.

AcOEt is added, followed by washing with a 10% aqueous solution of tartaric acid and with water.

The organic phase is dried over magnesium sulphate, filtered and the solvent is evaporated off under reduced pressure.

The crude product obtained is purified on silica, eluting with a dichloromethane/acetone mixture 95/5 containing 0.1% TEA.

In this way 36 mg of 6-(2-propenyloxy)-1,6-diazabicyclo[3.2.1]oct-3-in-7-one of molecular formula $C_9H_{12}N_2O_2$ (M=180.21 g) is recovered.

The corresponding yield is 11%.

Stage F

The operation is carried out in a similar manner to that described in Stage E of Example 52 starting from 51 mg (0.27 mmole) of the product obtained in Stage E, 33 µl of acetic acid, 165 mg of $Pd[P(C_6H_5)_3]_4$ and 132 mg of $SO_3$-pyridine complex.

In this way 29.6 mg of the 1-propenyltriphenylphosphonium salt of 6-(sulphooxy)-1,6-diazabicyclo[3.2.1]oct-3-in-7-one is recovered.

This salt is passed through a column of DOWEX 50WX8 resin in $Na^+$ form, followed by eluting with water containing 10% THF.

The product collected is lyophilized in order to obtain 13 mg of the expected sodium salt, of molecular formula $C_6H_7N_2O_5SNa$ (M=242.19 g).

The corresponding yield is 20%.

MS (negative electrospray) m/z: $[M]^-=219$

Example 54

Sodium salt of 6-(sulphooxy)-1,6-diazabicyclo[3.2.1]octan-7-one

The operation is carried out as indicated in Stage A of Example 53 starting from 12 g (0.061 mole) of 1,1-dimethylethyl 3,6-dihydro-3-oxo-1(2H)-pyridinecarboxylate of molecular formula $C_{10}H_{15}NO_3$, 9.7 g of O-benzylhydroxylamine hydrochloride and 15 ml of pyridine.

In this way 19.4 g of 1,1-dimethylethyl 3,6-dihydro-3-[(phenylmethoxy)imino]-1(2H)-pyridinecarboxylate of molecular formula $C_{17}H_{22}N_2O_3$ (M=302.38 g) is obtained.

The corresponding yield is quantitative.

Stage B

The operation is carried out as indicated in Stage B of Example 53 starting from 14.9 g (0.0496 mole) of the product obtained in Stage A, 12 g of sodium cyanoborohydide and 30 ml of boron trifluoride etherate.

In this way 8.2 g of a mixture of 2/3 of 1,1-dimethylethyl 3,6-dihydro-3-[(phenylmethoxy)amino]-1(2H)-pyridinecarboxylate and 1/3 of 1,1-dimethylethyl 3-[(phenylmethoxy)amino]-1-piperidinecarboxylate of molecular formula $C_{17}H_{24}N_2O_3$ (M=304.39 g) is obtained after purification.

The corresponding yield is 55%.

Stage C

The operation is carried out as indicated in Stage C of Example 53 starting from 9.3 g (0.0306 mole) of a mixture obtained in Stage B and 106 ml of a solution of hydrogen chloride in AcOEt at 7 mol/l.

In this way 8.39 g of a mixture of 2/3 of N-(phenylmethoxy)-1.2,3,6-tetrahydro-3-pyridinamine dihydrochloride and 1/3 of N-(phenylmethoxy)-3-piperidinamine dihydrochloride of molecular formula $C_{12}H_{18}Cl_2N_2O$ (M=277.20 g) is obtained.

The corresponding yield is 98%.

Stage D

The operation is carried out as indicated in Stage D of Example 53 starting from 8.30 g (0.0299 mole) of the mixture obtained in Stage C and 30 ml of 2N soda.

In this way 5.95 g of mixture of 2/3 of N-(phenylmethoxy)-1.2,3,6-tetrahydro-3-pyridinamine and 1/3 of N-(phenylmethoxy)-3-piperidinamine of molecular formula $C_{12}H_{16}N_2O$ (M=204.27 g) is obtained.

The corresponding yield is 98%.

Stage E

The operation is carried out as indicated in Stage E of Example 53 starting from 5.02 g (0.0246 mole) of a mixture obtained in Stage D, 2.43 ml of diphosgene, 7.4 ml of TEA and 3 g of DMAP.

In a flask equipped of a magnetic stirrer, 5.020 g (0.0246 mole) of the product obtained in Stage D and 1.2 ml of 1,2-dichloroethane are introduced at 0° C. and under argon.

2.43 g of diphosgene is added.

In this way 2.4 g of 6-(phenylmethoxy)-1,6-diazabicyclo[3.2.1]oct-3-in-7-one of molecular formula $C_{13}H_{14}N_2O_2$ (M=230.27 g) is recovered after purification.

The corresponding yield is 42%.

512 mg of 6-(phenylmethoxy)-1,6-diazabicyclo[3.2.1]octan-7-one of molecular formula $C_{13}H_{16}N_2O_2$ (M=232.27 g) is also recovered.

The corresponding yield is 9%.

Stage F 0.128 g (0.551 mmole) of 6-(phenylmethoxy)-1,6-diazabicyclo[3.2.1]octan-7-one obtained in Stage E is dissolved in 1 ml of methanol.

0.035 g of Pd/C catalyst is added and the reaction medium is placed under a hydrogen atmosphere at normal pressure. At the end of the reaction, the reaction medium is filtered, rinsed with methanol and the solvent is evaporated off under reduced pressure.

In this way 76 mg of 6-hydroxy-1,6-diazabicyclo[3.2.1]octan-7-one of molecular formula $C_6H_{10}N_2O_2$ (M=142.16 g) is obtained.

The corresponding yield is quantitative.

Stage G

In a flask placed under an inert atmosphere, 75 mg (0.528 mmole) of the product obtained in Stage F is introduced into 2 ml of pyridine.

235 mg of $SO_3$-pyridine complex is added and the reaction medium is left to react for 2 hours.

Then a few drops of water are added and the solvent is evaporated off under reduced pressure.

In this way 361 mg of crude product is obtained which is purified by chromatography on silica eluting with a dichloromethane/ethanol mixture 6/4 containing 0.1% by weight of TEA.

In this way 32 mg of the purified triethylammonium salt of 6-(sulphooxy)-1,6-diazabicyclo[3.2.1]octan-7-one, of molecular formula $C_{11}H_{15}N_3O_5S$ (M=301.32 g) is recovered.

The corresponding yield is 17%.

Stage H 31 mg of the product obtained in Stage G is dissolved in 0.5 ml of water containing 10% THF.

The solution obtained is passed through a column of DOWEX 50WX8 resin in $Na^+$ form, eluting with water containing 10% THF.

The product collected is lyophilized in order to obtain 20 mg of the expected sodium salt, of molecular formula $C_9H_9N_2O_5SNa$ (M=221 g).

The corresponding yield is 77%.

MS (negative electrospray) m/z: $[M-H]^-=221$

Pharmacological Study of the Products of the Invention

I/ The compounds of formula (I) and their pharmaceutically acceptable salts show marked inhibitory activities against the β-lactamases of various bacterial strains and these useful therapeutic properties can be determined in vitro on isolated β-lactamases:

A. Preparation of the β-lactamases Tem-1 and P99

The β-lactamases are isolated from bacterial strains which are resistant to penicillins and cephalosporins (Tem1 and P99 are produced by *E.coli* 250HT21 and *E.Cloacae* 293HT6 respectively).

The bacteria are cultured at 37° C. in heart-brain culture at 37 g/l (DIFCO). They are harvested at the end of the exponential phase, cooled down and centrifuged. The bacterial pellets are taken up in sodium phosphate buffer 50 mM, pH 7.0 and centrifuged again. The bacteria are taken up in two volumes of the same buffer and lyzed using a French-Press maintained at 4° C. After centrifugation for 1 hour at 100,000 g, at 4° C., the supernatants containing the soluble fraction of the bacterial extracts are recovered and frozen at −80° C.

B. Determination of the β-lactamases Activity

The method uses Nitrocefin (OXOID), cephalosporin chromogene as substrate, of which the product hydrolyzed by the B-lactamases is red and absorbs at 485 nm. Beta-lactamase activity is determined kinetically by measurement of the absorbance variation at 485 nm resulting from the hydrolysis of the substrate using a plate spectrophotometer (Spectra Max More Molecular Devices). The experiments are carried out at 37° C. The quantity of enzyme was normalized and the measurements are carried out at initial speed.

C. Determination of Compound Inhibitory Activity on β-lactamases

Two measurements were carried out, without preincubation and with preincubation of the enzyme and inhibitor (5 mn), in order to test the irreversibility of the reaction. The products are tested at 6 or 8 concentrations in duplicate. The reaction mixture contains 100 μM of Nitrocefin and 50 mM sodium phosphate buffer pH7.0.

D. Calculations of the IC50

The hydrolysis speeds are measured with and without inhibitor. The concentration of inhibitor which inhibits by 50% the hydrolysis reaction of Nitrocefin by the enzyme (CI50) is determined. The data is processed using GraFit software (Erathycus Software).

| EXAMPLE n° | IC$_{50}$ nM/TEM1 | IC$_{50}$ nM/P99 |
|---|---|---|
| 1a | 700 | (>10 000) |
| 2 | 462 | — |
| 2a | 6730 | — |
| 3 | 590 | 9800 |
| 3a | 4400 | — |
| 3b | 2010 | — |
| 4 | 2710 | — |
| 5 | 1010 | — |
| 7 | 650 | 250 |
| 7a | 55 | 17 |
| 8 | 1400 | 62 |
| 9 | 8500 | 630 |
| 10 | 0.26 | 1.50 |
| 14 | 6400 | — |
| 19$^e$ | 11 | — |
| 19f | 110 | — |
| 19g | 29 | — |
| 22 | 5100 | — |
| 25 | 28 | 600 |
| 26a | 115 | 1850 |
| 26b | 4900 | — |
| 26c | 1100 | 7000 |
| 28b | 9.5 | 12 |
| 28c | 29 | 1100 |
| 28d | 1.3 | 390 |
| 28$^e$ | 52 | — |
| 29b | 460 | 4200 |
| 29c | 450 | — |
| 29d | 9500 | 2000 |
| 29$^e$ | 4200 | 6300 |
| 29f | 5200 | — |
| 30 | 3500 | — |
| 31 | 5700 | — |
| 33 | 17 | 330 |
| 34 | 27 | 32 |
| 35 | 53 | 56 |
| 36 | 23 | 110 |
| 37 | 29 | 160 |
| 38 | 35 | 77 |
| 39 | 31 | 50 |
| 40 | 51 | 96 |
| 41 | 14 | 120 |
| 42 | 25 | 70 |
| 43 | 31 | 76 |
| 44 | 59 | 100 |
| 45 | 12 | 60 |
| 46 | 26 | 70 |
| 47 | 18 | 43 |
| 48 | 15 | 120 |
| 49 | 8.2 | 98 |
| 50 | 18 | 150 |
| 52 | 11 | 4600 |
| 53 | 15 | 5900 |
| 54 | 3100 | — |

II/ Inhibition of the β-lactamases shown above potentiates the antibiotic activity of β-lactamine type antibiotics, thus leading to a synergic effect, as the following results also show, which express the minimal inhibitory concentration in vitro (MIC in μg/ml), vis-à-vis a certain number of pathogenic microorganisms, of combinations of cefotaxime and piperacillin with compounds of formula (I) at a concentration of 5 mg/l. The operation is carried out as follows, using the so-called micro-dilution in liquid medium method.

A series of concentrations of the β-lactamine is prepared in the presence of a constant concentration (5 mg/l) of the product to be studied, each is then seeded with various bacterial strains.

After incubation for 24 hours in a heating chamber at 37° C., the growth inhibition is evaluated by the absence of any bacterial development, which allows the minimal inhibitory concentrations (MIC) for each strain to be determined, expressed in milligrams/l.

The following results were obtained:

| Trial N° | Strain | Phenotype | Cefotaxime | Wt. | Ex. 35 | Ex. 33 |
|---|---|---|---|---|---|---|
| 1 | 011GO66 | S. aureus | PeniR | 1.2 | 1.2 | 2.5 |
| 2 | 250HT21 | E. coli | Tem1 | <=0.04 | <=0.04 | <=0.04 |
| 3 | 250HT22 | E. coli | Tem2 | <=0.04 | <=0.04 | <=0.04 |
| 4 | 250CF1 | E. coli | Tem3 | >40 | 0.15 | <=0.04 |
| 5 | 250SJ1 | E. coli | Tem7 | 0.08 | <=0.04 | <=0.04 |
| 6 | 250HT26 | E. coli | SHV1 | 0.6 | <=0.04 | <=0.04 |
| 7 | 250BE1 | E. coli | SHV4 | 40 | 0.08 | <=0.04 |
| 8 | 250HT23 | E. coli | Class D | 0.08 | <=0.04 | <=0.04 |
| 9 | 293HT6 | E. cloacae | Class C | >40 | 0.6 | <=0.04 |
| 10 | 301HT6 | Serratia | Serratia | 0.3 | <=0.04 | 0.08 |
| 11 | 391HT7 | P. aeruginosa | PSE | 40 | 20 | 20 |
| 12 | 391HT8 | P. aeruginosa | PSE | 40 | 20 | 20 |

| Trial N° | Ex. 34 | Ex. 36 | Ex. 37 | Ex. 38 | Ex. 39 | Ex. 40 | Ex. 41 |
|---|---|---|---|---|---|---|---|
| 1 | 1.2 | 1.2 | 1.2 | 1.2 | 2.5 | 2.5 | 2.5 |
| 2 | <=0.04 | <=0.04 | <=0.04 | <=0.04 | <=0.04 | <=0.04 | <=0.04 |
| 3 | <=0.04 | <=0.04 | <=0.04 | <=0.04 | <=0.04 | <=0.04 | <=0.04 |
| 4 | 0.15 | 0.3 | 0.3 | 0.3 | 0.08 | 0.6 | 2.5 |
| 5 | <=0.04 | <=0.04 | 0.08 | <=0.04 | <=0.04 | 0.15 | 0.6 |
| 6 | <=0.04 | <=0.04 | <=0.04 | <=0.04 | <=0.04 | <=0.04 | <=0.04 |
| 7 | 0.08 | 0.3 | 0.6 | 0.3 | 0.08 | 1.2 | >40 |
| 8 | <=0.04 | <=0.04 | <=0.04 | <=0.04 | <=0.04 | <=0.04 | 0.08 |
| 9 | 0.6 | 20 | >40 | 20 | 1.2 | >40 | >40 |
| 10 | <=0.04 | 0.08 | 0.08 | 0.08 | <=0.04 | 0.08 | 0.08 |
| 11 | 20 | 40 | 20 | 40 | 20 | >40 | >40 |
| 12 | 20 | 40 | 20 | 40 | 20 | >40 | >40 |

| Trial N° | Ex. 42 | Ex. 43 | Ex. 44 | Ex. 48 | Ex. 49 |
|---|---|---|---|---|---|
| 1 | 2.5 | 2.5 | 2.5 | 2.5 | 2.5 |
| 2 | <=0.04 | <=0.04 | <=0.04 | <=0.04 | <=0.04 |
| 3 | <=0.04 | <=0.04 | 0.15 | <=0.04 | <=0.04 |
| 4 | <=0.04 | 0.08 | 0.3 | <=0.04 | 0.08 |
| 5 | <=0.04 | <=0.04 | 0.08 | <=0.04 | <=0.04 |
| 6 | <=0.04 | <=0.04 | 0.08 | <=0.04 | <=0.04 |
| 7 | <=0.04 | <=0.04 | 0.6 | 0.08 | <=0.04 |
| 8 | <=0.04 | <=0.04 | <=0.04 | <=0.04 | <=0.04 |
| 9 | 0.3 | 0.08 | >40 | 0.15 | Nd |
| 10 | <=0.04 | <=0.04 | 10 | <=0.04 | Nd |
| 11 | 20 | 20 | >40 | 40 | Nd |
| 12 | 20 | 20 | >40 | >40 | nd |

| Trial N° | Strain | Phenotype | Piperacillin | Wt. | Ex. 35 | Ex. 33 | Ex. 34 |
|---|---|---|---|---|---|---|---|
| 1 | 011GO66 | peniR | 10 | 1.2 | 1.2 | 0.6 |
| 2 | 250HT21 | Tem1 | >40 | 2.5 | 0.3 | 5 |
| 3 | 250HT22 | Tem2 | >40 | 20 | 0.6 | >40 |
| 4 | 250CF1 | Tem3 | >40 | 10 | 1.2 | >40 |
| 5 | 250SJ1 | Tem7 | >40 | 5 | 0.6 | >40 |

-continued

| Trial N° | Strain | Phenotype | Piperacillin | Wt. Ex. 35 | Ex. 33 | Ex. 34 |
|---|---|---|---|---|---|---|
| 6 | 250HT26 | SHV1 | >40 | 5 | 1.2 | 20 |
| 7 | 250BE1 | SHV4 | >40 | 20 | 1.2 | >40 |
| 8 | 250HT23 | Class D | >40 | 10 | 2.5 | 40 |
| 9 | 293HT6 | Class | >40 | 5 | 0.6 | 10 |
| 10 | 301HT6 | *Serratia* | 5 | 1.2 | 0.6 | 1.2 |
| 11 | 391HT7 | PSE | >40 | >40 | >40 | >40 |
| 12 | 391HT8 | PSE | >40 | >40 | 10 | >40 |

| Trial N° | Ex. 36 | Ex. 37 | Ex. 38 | Ex. 39 | Ex. 40 | Ex. 41 | Ex. 42 |
|---|---|---|---|---|---|---|---|
| 1 | 1.2 | 0.6 | 0.6 | 1.2 | 0.6 | 1.2 | 1.2 |
| 2 | 5 | 2.5 | 5 | 2.5 | 10 | 40 | 1.2 |
| 3 | 40 | >40 | >40 | 20 | >40 | >40 | 2.5 |
| 4 | 40 | 40 | 20 | 40 | >40 | >40 | 2.5 |
| 5 | 20 | >40 | >40 | >40 | >40 | >40 | 2.5 |
| 6 | 20 | 20 | 40 | 40 | >40 | >40 | 5 |
| 7 | >40 | >40 | >40 | 20 | >40 | >40 | 5 |
| 8 | 20 | 40 | >40 | 10 | 20 | 40 | 5 |
| 9 | 20 | 40 | 40 | 20 | >40 | >40 | 1.2 |
| 10 | 1.2 | 2.5 | 1.2 | 0.6 | 1.2 | 1.2 | 0.6 |
| 11 | >40 | >40 | >40 | >40 | >40 | >40 | >40 |
| 12 | >40 | >40 | >40 | >40 | >40 | >40 | >40 |

| Trial N° | Ex. 43 | Ex. 44 | Ex. 45 | Ex. 46 | Ex. 47 | Ex. 48 | Ex. 49 | Ex. 50 |
|---|---|---|---|---|---|---|---|---|
| 1 | 1.2 | 2.5 | 1.2 | 0.6 | 0.6 | 1.2 | 1.2 | 1.2 |
| 2 | 1.2 | 5 | 1.2 | 5 | 2.5 | 0.6 | 1.2 | 2.5 |
| 3 | 1.2 | >40 | 2.5 | >40 | 20 | 2.5 | 2.5 | 40 |
| 4 | 2.5 | 40 | 2.5 | 2.5 | 5 | 1.2 | 1.2 | 5 |
| 5 | 5 | >40 | 2.5 | >40 | 40 | 1.2 | 5 | 40 |
| 6 | 5 | >40 | 2.5 | >40 | 2.5 | 1.2 | 20 | 40 |
| 7 | 10 | >40 | 5 | 40 | 5 | 2.5 | 20 | 40 |
| 8 | 2.5 | 40 | 10 | 10 | 10 | 5 | 10 | 40 |
| 9 | 2.5 | >40 | 1.2 | >40 | >40 | 2.5 | 10 | >40 |
| 10 | 0.6 | >40 | 0.6 | 1.2 | 1.2 | 0.6 | nd | 0.6 |
| 11 | >40 | >40 | >40 | >40 | >40 | >40 | nd | >40 |
| 12 | >40 | >40 | >40 | >40 | >40 | >40 | nd | >40 |

Example of a Pharmaceutical Composition:

1/ A pharmaceutical composition (lyophilisates) for injection was prepared containing

| on the one hand: compound of Example 35 | 500 mg |
| on the other hand: Cefotaxime | 1 g |
| Sterile aqueous excipient s.q.f. | 5 cm³ |

The two active ingredients can, if desired, be introduced separately into two distinct ampoules or flasks.

2/ A pharmaceutical composition (lyophilisates) for injection was prepared containing

| on the one hand: compound of Example 33 | 250 mg |
| on the other hand: Cefpirone | 1 g |
| Excipient sterile aqueous s.q.f. | 5 cm³ |

The two active ingredients can, if desired, be introduced separately into two distinct ampoules or flasks.

What is claimed is:

1. A pharmaceutical composition comprising a bacterial β-lactamase inhibitory amount of a compound, or a pharmaceutically acceptable salt thereof, of formula (I):

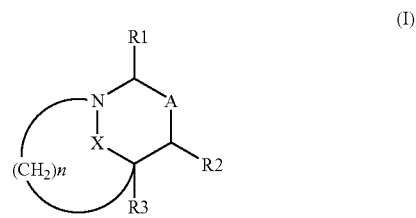

wherein $R_1$ is hydrogen, COOH, CN, COOR, CONR$_6$R$_7$, $(CH_2)_n R_5$ or $C(=NR_6)NHR_7$;

R is selected from the group consisting of alkyl containing 1 to 6 carbon atoms optionally substituted by a pyridyl or carbamoyl radical, —CH$_2$-alkenyl containing 3 to 9 carbon atoms, aryl containing 6 to 10 carbon atoms and aralkyl containing 7 to 11 carbon atoms, wherein the nucleus of said aryl or aralkyl is optionally substituted by OH, NH$_2$, NO$_2$, alkyl containing 1 to 6 carbon atoms, alkoxy containing 1 to 6 carbon atoms or by one or more halogen atoms;

$R_6$ and $R_7$ are identical or different and are independently selected from the group consisting of hydrogen, alkyl containing 1 to 6 carbon atoms, aryl containing 6 to 10 carbon atoms and aralkyl containing 7 to 11 carbon atoms optionally substituted by a carbamoyl, ureido or dimethylamino radical, and alkyl containing 1 to 6 carbon atoms substituted by a pyridyl radical;

n' is 1 or 2;

$R_5$ is selected from the group consisting of COOH, CN, OH, NH$_2$, CO-NR$_6$R$_7$, COOR, OR, OCHO, OCOR, OCOOR, OCONHR, OCONH$_2$, NHR, NHCOH, NHCOR, NHSO$_2$R, NH—COOR, NH—CO—NHR and NHCONH$_2$ wherein R, $R_6$ and $R_7$ are as defined above;

$R_2$ is hydrogen or $(CH_2)_{n'_1} R_5$ wherein $n'_1$ is 0, 1 or 2, and $R_5$ is as defined above;

$R_3$ is hydrogen or alkyl containing 1 to 6 carbon atoms;

A is a

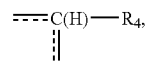

group wherein $R_4$ is hydrogen or $(CH_2)_{n'_1} R_5$ and $n'_1$ and $R_5$ are as defined above, and the dotted line is an optional bond with one of the two carbons which carry $R_1$ and $R_2$;

n is 1;

X is a divalent —C(O)—B— group linked to the nitrogen atom by the carbon atom wherein B is a divalent —O—$(CH_2)_{n''}$— group linked to the carbonyl by the oxygen atom, a divalent —NR$_8$—(CH$_2$)$_{n''}$— or —NR$_8$—O— group linked to the carbonyl by the nitrogen atom, n" is 0, and wherein B is —NR$_8$—(CH$_2$)$_{n''}$—, $R_8$ is selected from the group consisting of hydrogen, OH, R, OR, Y, OY, Y$_1$, OY$_1$, Y$_2$, OY$_2$, Y$_3$, OCH$_2$CH$_2$SO$_m$R, OSiR$_a$R$_b$R$_c$ and SiR$_a$R$_b$R$_c$ and wherein B is —NR$_8$—O—, $R_8$ is selected from the group consisting of hydrogen, R, Y, Y$_1$, Y$_2$, Y$_3$ and SiR$_a$R$_b$R$_c$, wherein R$_a$, R$_b$ and R$_c$ is each independently a linear or branched alkyl containing 1 to 6 carbon atoms or aryl containing 6 to 10 carbon atoms, R is as defined above and m is 0, 1 or 2;

Y is selected from the group consisting of COH, COR, COOR, $CONH_2$, CONHR, CONHOH, $CONHSO_2R$, $CH_2COOH$, $CH_2COOR$, $CH_2CONHOH$, $CH_2CONHCN$, $CH_2$tetrazole, protected $CH_2$tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$;

$Y_1$ is selected from the group consisting of $SO_2R$, $SO_2NHCOH$, $SO_2NHCOR$, $SO_2NHCOOR$, $SO_2NHCONHR$, $SO_2NHCONH_2$ and $SO_3H$;

$Y_2$ is selected from the group consisting of $PO(OH)_2$, $PO(OR)_2$, PO(OH)(OR) and PO(OH)(R);

$Y_3$ is selected from the group consisting of tetrazole, tetrazole substituted by R, squarate, NH or NR-tetrazole, NH or NR-tetrazole substituted by R, $NHSO_2R$ and $NRSO_2R$ wherein R is as defined above; and $R_1$, $R_2$ and $R_3$ are not simultaneously hydrogen when n is 1, $R_4$ is hydrogen and X is —C(O)—O—$(CH_2)_{n''}$ wherein n" is 0, or
, or
X is —CO—$NR_8$—$(CH_2)_{n''}$ wherein n" is 0 and $R_8$ is hydrogen or phenyl; and a therapeutically effective amount of a β-lactamine antibiotic.

2. The pharmaceutical composition of claim 1, wherein said β-lactamine antibiotic is selected from the group consisting of: penams, penems, carbapenems, cephems, carbacephems, oxacephems, cephamycims, monobactams, combinations and pharmaceutically acceptable salts thereof.

3. The pharmaceutical composition of claim 1, wherein said compound of Formula (I) comprises trans-7-oxo-6-(sulphooxy)-1,6-diazabicyclo-[3.2.1]-octane-2-carboxamide or a pharmaceutically acceptable salt thereof.

4. The pharmaceutical composition of claim 1, wherein said compound of Formula (I) comprises trans-7-oxo-6-(sulphooxy)- 1,6-diazabicyclo-[3.2.1 ]-octane-2-carboxamide or a pharmaceutically acceptable salt thereof and said β-lactamine antibiotic comprises ceftazidime.

5. A pharmaceutical composition according to claim 1, wherein said β-lactamine antibiotic comprises a cephalosporin antibiotic selected from the group consisting of: cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, latamoxef, combinations and pharmaceutically acceptable salts thereof.

6. A pharmaceutical composition according to claim 1, wherein said β-lactamine antibiotic comprises ceftazidime.

7. The pharmaceutical composition according to claim 1 wherein n is 1, $R_3$ is hydrogen, $R_1$ is hydrogen, COOR or $CONR_6R_7$ wherein R, $R_6$ and $R_7$ are as defined in claim 1, and X is —C(O)—B—herein B is —O—$(CH_2)_{n''}$—or —$NR_8$—$(CH_2)_{n''}$— wherein n" is 0 and $R_8$ is as defined in claim 1.

8. The pharmaceutical composition according to claim 1 wherein $R_8$ is Y, $Y_1$ or $OY_1$, and Y and $Y_1$ are as defined in claim 1.

9. The pharmaceutical composition according to claim 1 wherein $R_2$ and $R_4$ are each hydrogen, and B is —$NR_8$—$(CH_2)_{n''}$— wherein n" is 0 and $R_8$ is $OY_1$.

10. The pharmaceutical composition according to claim 9 wherein $R_3$ is hydrogen, and $R_1$ is hydrogen, COOR or $CONR_6R_7$.

11. The pharmaceutical composition according to claim 1 wherein the compound of Formula (I) is selected from the group consisting of:

cis-7-oxo-6-oxa-1-azabicyclo[3.2.1]octane-4-propanoic acid, trans diphenylmethyl 7-oxo-6-oxa-1-azabicyclo[3.2.1]octan-4-acetate, cis diphenylmethyl 7-oxo-6-oxa-1-azabicyclo[3.2.1 ]octan-4-acetate, trans phenylmethyl 3-benzoyl-2-oxo-1,3-diazabicyclo[2.2.1 ]heptane-6-carboxylate, trans phenylmethyl 2-oxo-3-(sulphooxy)-1,3-diazabicyclo[2.2.1 ]heptane-6-carboxylate, 6-[[(4-methylphenyl)sulphonyl]oxy]-1,6-diazabicyclo[3.2.1]octan-7-one, 6-[(methylsulphonyl)oxy]-1,6-diazabicyclo[3.2.1]octan-7-one, 6-[(4-nitrophenyl)sulphonyl]oxy]-1,6-diazabicyclo[3.2.1]octan-7-one, trans diphenylmethyl 7-oxo-6-oxa-1-azabicyclo[3.2.1 ]octane-2-carboxylate, trans (4-nitrophenyl)methyl 7-oxo-6-oxa-1-azabicyclo[3.2.1 ]octane-2-carboxylate, trans-7-oxo-6-oxa-1-azabicyclo[3.2.1]octane-2 carboxylic acid, trans phenylmethyl 7-oxo-6-(sulphooxy)-1,6-diazabicyclo[3.2.1]octane-2-carboxylate, trans phenylmethyl 7-oxo-6-(sulphooxy)-1,6-diazabicyclo[3.2.1]octane-2-carboxylate, trans phenylmethyl 7-oxo-6-[(phenylsulphonyl)oxy]-1,6-diazabicyclo[3.2.1]octane-2-carboxylate, trans phenylmethyl 7-oxo-6-[(2-thienylsulphonyl)oxy]-1,6-diazabicyclo[3-.2.1]octane-2-carboxylat trans-6-benzoyl-7-oxo-1,6-diazabicyclo[3.2.1]octane-2-carboxylic acid, trans methyl 6-benzoyl-7-oxo-1,6-diazabicyclo[3.2.1]octane-2-carboxylate, trans-7-oxo-6-(sulphooxy)-1,6-diazabicyclo[3.2.1]octane-2-carboxamide, trans-7-oxo-N-(phenylmethyl)-6-(sulphooxy)-1,6-diazabicyclo[3.2.1]octane-2-carboxamide, trans-7-oxo-N-(2-pyridinylmethyl)-6-(sulphooxy)-1,6-diazabicyclo[3.2.1]octane-2-carboxamide, trans-7-oxo-N-[2-(3-pyridinyl)ethyl]-6-(sulphooxy)-1,6-diazabicyclo[3.2.1]octane-2-carboxamide, trans-7-oxo-N-[2-(4-pyridinyl)ethyl]-6-(sulphooxy)-1,6-diazabicyclo[3.2.1]octane-2-carboxamide, trans-7-oxo-N-[2-(2-pyridinyl)ethyl]-6-(sulphooxy)-1,6-diazabicyclo[3.2.1]octane-2-carboxamide, trans-N-[3-(aminocarbonyl)phenyl]-7-oxo-6-(sulphooxy)-1,6-diazabicyclo[3-.2.1]octane-2-carboxamide, trans-N-[4-(dimethylamino)phenyl]-7-oxo-6-(sulphooxy)-1,6-diazabicyclo [3.2.1 ]octane-2-carboxamide, trans-N-[3-(dimethylamino)phenyl]-7-oxo-6-(sulphooxy)-1,6-diazabicyclo [3.2.1 ]octane-2-carboxamide, trans-7-oxo-N-[(4-pyridinyl)methyl]-6-(sulphooxy)-1,6-diazabicyclo[3.2.1]octane-2-carboxamide, trans-7-oxo-N-(3-pyridinyimethyl)-6-(sulphooxy)-1,6-diazabicyclo[3.2.1]octane-2-carboxamide, trans-N-(1-amino-1-oxo-3-phenyl-2-propyl)-7-oxo-6-(sulphooxy)-1,6-diazabicyclo[3.2.1]octane-2-carboxamide, trans-N-(2-amino-2-oxoethyl)-7-oxo-6-(sulphooxy)-1,6-diazabicyclo[3.2.1]octane-2-carboxamide, trans-N-[3-[(aminocarbonyl)amino]phenyl]-7-oxo-6-(sulphooxy)-1,6-diazabicyclo[3.2.1]octane-2-carboxamide, trans-N-(2-amino-2-oxo-1-phenylethyl)-7-oxo-6-(sulphooxy)-1,6-diazabicyclo[3.2.1]octane-2-carboxamide, trans-7-oxo-6-(sulphooxy)-1,6-diazabicyclo[3.2.1]octane-2-carboxylate of 2-amino-2-oxoethyl, trans 2-(4-pyridinyl)ethyl 7-oxo-6-(sulphooxy)-1,6-diazabicyclo[3.2.1]octane-2-carboxylate, trans 2-(2-pyridinyl)ethyl 7-oxo-6-(sulphooxy)-1,6-diazabicyclo[3.2.1]octane-2-carboxylate, 6-(sulphooxy)-1,6-diazabicyclo[3.2.1]oct-3-in-7-one, and 3-methoxy-6-(sulphooxy)-1,6-diazabicyclo[3.2.1]oct-3-in-7-one.

12. The pharmaceutical composition of claim 11 comprising said compounds and pharmaceutically acceptable salts of Formula (I) and further comprising said β-lactamine antibiotic selected from the group consisting of: penams, penems, carbapenems, cephems, carbacephems, oxacephems, cephamycims, monobactams, combinations and pharmaceutically acceptable salts thereof.

13. The pharmaceutical composition of claim 11 comprising said compounds and pharmaceutically acceptable salts of Formula I and further comprising said β-lactamine antibiotic selected from the group consisting of: amoxicillin, ampicillin, azlocillin, mezlocillin, apalcillin, hetacillin, bacampicillin, carbenicillin, sulbenicillin, ticarcillin, piperacillin, azlocillin, mecillinam, pivmecillinam, methicillin, ciclacillin, talampicillin, aspoxicillin, oxacillin, cloxacillin, dicloxacillin, flucloxacillin, nafcillin or pivampicillin, the cephalosporins such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, latamoxef, the carbapenems such as imipenem, meropenem, biapenem or panipenem and the monobactams such as aztreonam and carumonam, combinations and pharmaceutically acceptable salts thereof.

14. The pharmaceutical composition of claim 11 comprising said compounds and pharmaceutically acceptable salts of Formula I and further comprising said β-lactamine antibiotic selected from the group consisting of: cephalothin, cephaloridine, cefaclor, cefadroxil, cefamandole, cefazolin, cephalexin, cephradine, ceftizoxime, cefoxitin, cephacetrile, cefotiam cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, latamoxef, combinations and pharmaceutically acceptable salts thereof.

15. The pharmaceutical composition according to claim 1 wherein said compound of Formula (I) comprises a sodium salt of trans-7-oxo-6-(sulphooxy)-1,6-diazabicyclo-[3.2.1]-octane-2-carboxamide.

16. The pharmaceutical composition of claim 1, wherein said compound of Formula (I) comprises a sodium salt of trans-7-oxo-6-(sulphooxy)-1,6-diazabicyclo-[3.2.1]-octane-2-carboxamide and said Δ-lactamine antibiotic comprises ceftazidime.

* * * * *

UNITED STATES PATENT AND TRADEMARK OFFICE
CERTIFICATE OF CORRECTION

PATENT NO. : 7,612,087 B2 Page 1 of 1
APPLICATION NO. : 10/898754
DATED : November 3, 2009
INVENTOR(S) : Aszodi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1385 days.

Signed and Sealed this

Nineteenth Day of October, 2010

David J. Kappos
*Director of the United States Patent and Trademark Office*